United States Patent
Chilkoti et al.

(10) Patent No.: US 12,257,308 B2
(45) Date of Patent: Mar. 25, 2025

(54) STIMULI-RESPONSIVE PEG-LIKE POLYMER-BASED DRUG DELIVERY PLATFORM

(71) Applicant: Duke University, Durham, NC (US)

(72) Inventors: Ashutosh Chilkoti, Durham, NC (US); Imran Ozer, Durham, NC (US)

(73) Assignee: Duke University, Durham, NC (US)

( * ) Notice: Subject to any disclaimer, the term of this patent is extended or adjusted under 35 U.S.C. 154(b) by 678 days.

(21) Appl. No.: 17/051,202

(22) PCT Filed: Apr. 30, 2019

(86) PCT No.: PCT/US2019/030022
§ 371 (c)(1),
(2) Date: Oct. 28, 2020

(87) PCT Pub. No.: WO2019/213150
PCT Pub. Date: Nov. 7, 2019

(65) Prior Publication Data
US 2021/0128734 A1    May 6, 2021

Related U.S. Application Data

(60) Provisional application No. 62/664,512, filed on Apr. 30, 2018.

(51) Int. Cl.
*A61K 47/58* (2017.01)
*A61K 38/22* (2006.01)
*A61P 3/10* (2006.01)

(52) U.S. Cl.
CPC .......... *A61K 47/58* (2017.08); *A61K 38/2278* (2013.01); *A61P 3/10* (2018.01)

(58) Field of Classification Search
CPC ..................................................... A61K 47/58
See application file for complete search history.

(56) References Cited

U.S. PATENT DOCUMENTS

| | | | |
|---|---|---|---|
| 4,415,732 | A | 11/1983 | Caruthers et al. |
| 4,458,066 | A | 7/1984 | Caruthers et al. |
| 4,500,707 | A | 2/1985 | Caruthers et al. |
| 4,554,101 | A | 11/1985 | Hopp |
| 4,668,777 | A | 5/1987 | Caruthers et al. |
| 4,973,679 | A | 11/1990 | Caruthers et al. |
| 4,976,734 | A | 12/1990 | Urry et al. |

(Continued)

FOREIGN PATENT DOCUMENTS

| | | |
|---|---|---|
| AU | 2007265628 B2 | 12/2012 |
| CA | 2327325 A1 | 11/1999 |

(Continued)

OTHER PUBLICATIONS

Liu et al (Bioconjugate Chem. 2016, 27, 54-58). (Year: 2016).*

(Continued)

*Primary Examiner* — Benjamin J Packard
(74) *Attorney, Agent, or Firm* — Michael Best & Friedrich LLP

(57) ABSTRACT

Described herein are thermally responsive polymer-therapeutic molecule conjugates comprising a therapeutic molecule conjugated to a thermally responsive polymer with an acrylate, methacrylate, acrylamide, and/or methacrylamide backbone and a plurality of oligoethylene glycol side chains.

18 Claims, 28 Drawing Sheets

(56) References Cited

U.S. PATENT DOCUMENTS

| | | |
|---|---|---|
| 5,153,319 A | 10/1992 | Caruthers et al. |
| 5,250,516 A | 10/1993 | Urry |
| 5,278,302 A | 1/1994 | Caruthers et al. |
| 5,336,256 A | 8/1994 | Urry |
| 5,453,496 A | 9/1995 | Caruthers et al. |
| 5,534,408 A | 7/1996 | Green et al. |
| 5,578,577 A | 11/1996 | Ching et al. |
| 5,580,859 A | 12/1996 | Felgner et al. |
| 5,602,244 A | 2/1997 | Caruthers et al. |
| 5,676,646 A | 10/1997 | Hofmann et al. |
| 5,679,647 A | 10/1997 | Carson et al. |
| 5,702,359 A | 12/1997 | Hofmann et al. |
| 5,703,055 A | 12/1997 | Felgner et al. |
| 5,935,776 A | 8/1999 | Green et al. |
| 6,068,650 A | 5/2000 | Hofmann et al. |
| 6,096,020 A | 8/2000 | Hofmann |
| 6,120,493 A | 9/2000 | Hofmann |
| 6,150,148 A | 11/2000 | Nanda et al. |
| 6,181,964 B1 | 1/2001 | Hofmann et al. |
| 6,192,270 B1 | 2/2001 | Hofmann et al. |
| 6,207,749 B1 | 3/2001 | Mayes et al. |
| 6,208,893 B1 | 3/2001 | Hofmann |
| 6,216,034 B1 | 4/2001 | Hofmann et al. |
| 6,233,482 B1 | 5/2001 | Hofmann et al. |
| 6,241,701 B1 | 6/2001 | Hofmann |
| 6,245,515 B1 | 6/2001 | Vogelstein et al. |
| 6,296,831 B1 | 10/2001 | Weller et al. |
| 6,302,874 B1 | 10/2001 | Zhang et al. |
| 6,413,587 B1 | 7/2002 | Hawker et al. |
| 6,512,060 B1 | 1/2003 | Matyjaszewski et al. |
| 6,541,580 B1 | 4/2003 | Matyjaszewski et al. |
| 6,623,950 B1 | 9/2003 | Osten et al. |
| 6,649,138 B2 | 11/2003 | Adams et al. |
| 6,660,247 B1 | 12/2003 | Gutowska et al. |
| 6,841,617 B2 | 1/2005 | Jeong et al. |
| 6,852,834 B2 | 2/2005 | Chilkoti |
| 6,869,588 B2 | 3/2005 | Weller et al. |
| 7,033,571 B2 | 4/2006 | Gutowska et al. |
| 7,087,244 B2 | 8/2006 | Jeong et al. |
| 7,300,922 B2 | 11/2007 | Sullenger et al. |
| 7,429,458 B2 | 9/2008 | Chilkoti |
| 7,531,524 B2 | 5/2009 | Rusconi |
| 7,664,545 B2 | 2/2010 | Westersten et al. |
| 7,674,882 B2 | 3/2010 | Kaplan et al. |
| 8,129,330 B2 | 3/2012 | Martinez et al. |
| 8,283,125 B2 | 10/2012 | Cebolla Ramirez et al. |
| 8,470,967 B2 | 6/2013 | Chilkoti et al. |
| 8,497,356 B2 | 7/2013 | Chilkoti et al. |
| 8,506,963 B2 | 8/2013 | Li et al. |
| 8,586,347 B2 | 11/2013 | Lochhead et al. |
| 8,841,414 B1 | 9/2014 | Raucher et al. |
| 8,912,310 B2 | 12/2014 | Chilkoti et al. |
| 8,937,153 B2 | 1/2015 | Abrahmsén et al. |
| 9,127,047 B2 | 9/2015 | Chilkoti |
| 9,132,178 B2 | 9/2015 | Philip |
| 9,138,743 B2 | 9/2015 | Yager et al. |
| 9,482,664 B2 | 11/2016 | Chilkoti et al. |
| 9,592,303 B2 | 3/2017 | Chilkoti et al. |
| 9,771,396 B2 | 9/2017 | Chilkoti et al. |
| 9,804,170 B2 | 10/2017 | Krishna et al. |
| 9,890,420 B2 | 2/2018 | Chilkoti et al. |
| 10,064,954 B2 | 9/2018 | Wu |
| 10,131,690 B2 | 11/2018 | Bonny et al. |
| 10,302,636 B2 | 5/2019 | Chilkoti et al. |
| 10,364,451 B2 | 7/2019 | Chilkoti et al. |
| 10,385,115 B2 | 8/2019 | Chilkoti et al. |
| 10,434,182 B2 | 10/2019 | Weng et al. |
| 2001/0034050 A1 | 10/2001 | Chilkoti |
| 2002/0052443 A1 | 5/2002 | Greenwald et al. |
| 2002/0146794 A1 | 10/2002 | Tomycz |
| 2003/0008308 A1 | 1/2003 | Enzelberger et al. |
| 2003/0138829 A1 | 1/2003 | Unger et al. |
| 2003/0175290 A1 | 9/2003 | Renner et al. |
| 2003/0185741 A1 | 10/2003 | Matyjaszewski et al. |
| 2003/0225251 A1 | 12/2003 | Sallberg et al. |
| 2003/0233675 A1 | 12/2003 | Cao et al. |
| 2004/0053976 A1 | 3/2004 | Martinez et al. |
| 2004/0101852 A1 | 5/2004 | Bennett et al. |
| 2004/0192072 A1 | 9/2004 | Snow et al. |
| 2005/0186214 A1 | 8/2005 | Liu et al. |
| 2005/0255554 A1 | 11/2005 | Chilkoti |
| 2005/0288229 A1 | 12/2005 | Sindrey et al. |
| 2006/0025524 A1 | 2/2006 | Schneider et al. |
| 2006/0034796 A1 | 2/2006 | Ashwell et al. |
| 2006/0051798 A1 | 3/2006 | Mirkin et al. |
| 2007/0087114 A1 | 4/2007 | Chilkoti et al. |
| 2007/0117173 A1 | 5/2007 | Levison et al. |
| 2008/0181861 A1 | 7/2008 | Jiang et al. |
| 2009/0098652 A1 | 4/2009 | Stupp et al. |
| 2009/0215194 A1 | 8/2009 | Magni et al. |
| 2009/0247424 A1 | 10/2009 | Chilkoti et al. |
| 2010/0015070 A1 | 1/2010 | Bollschweiler et al. |
| 2010/0022455 A1 | 1/2010 | Chilkoti |
| 2010/0048473 A1 | 2/2010 | Chaikof et al. |
| 2010/0120018 A1 | 5/2010 | Quake et al. |
| 2010/0241054 A1 | 9/2010 | Dacey et al. |
| 2010/0311059 A1 | 12/2010 | Didion et al. |
| 2010/0311669 A1 | 12/2010 | Greene et al. |
| 2010/0325765 P1 | 12/2010 | Pait et al. |
| 2011/0082283 A1 | 4/2011 | Dagher et al. |
| 2011/0110866 A1 | 5/2011 | Chilkoti et al. |
| 2011/0119778 A1 | 5/2011 | Liss |
| 2011/0165557 A1 | 7/2011 | Ah et al. |
| 2011/0207673 A1 | 8/2011 | Chilkoti et al. |
| 2011/0294189 A1 | 12/2011 | Chilkoti et al. |
| 2011/0303303 A1 | 12/2011 | Proper et al. |
| 2011/0305718 A1 | 12/2011 | Mugica et al. |
| 2012/0172298 A1 | 7/2012 | Andersen et al. |
| 2012/0208742 A1 | 8/2012 | Primiano et al. |
| 2013/0039927 A1 | 2/2013 | Dewhurst et al. |
| 2013/0079277 A1 | 3/2013 | Chilkoti |
| 2013/0079280 A1 | 3/2013 | Baca et al. |
| 2013/0096058 A1 | 4/2013 | Baca et al. |
| 2013/0102993 A1 | 4/2013 | Kim et al. |
| 2013/0130384 A1 | 5/2013 | Okamoto et al. |
| 2013/0157889 A1 | 6/2013 | Chilkoti et al. |
| 2013/0165389 A1 | 6/2013 | Schellenberger et al. |
| 2013/0172274 A1 | 7/2013 | Chilkoti |
| 2013/0197359 A1 | 8/2013 | Park et al. |
| 2013/0315823 A1 | 11/2013 | Trieu |
| 2013/0330335 A1 | 12/2013 | Bremel et al. |
| 2014/0024600 A1 | 1/2014 | Chilkoti et al. |
| 2014/0163201 A1 | 6/2014 | Winter et al. |
| 2014/0275227 A1 | 9/2014 | Hoge et al. |
| 2014/0294932 A1 | 10/2014 | Kim et al. |
| 2015/0094270 A1 | 4/2015 | Harris et al. |
| 2015/0099707 A1 | 4/2015 | Pastan et al. |
| 2015/0112022 A1 | 4/2015 | Chilkoti et al. |
| 2016/0017278 A1 | 1/2016 | Montclare et al. |
| 2016/0114053 A1 | 4/2016 | Chilkoti |
| 2016/0120952 A1 | 5/2016 | Chilkoti |
| 2016/0200787 A1 | 7/2016 | Matern et al. |
| 2016/0209356 A1 | 7/2016 | Herget et al. |
| 2016/0220727 A1 | 8/2016 | Lu et al. |
| 2016/0250165 A1 | 9/2016 | Sullenger et al. |
| 2016/0271262 A1 | 9/2016 | Lopez et al. |
| 2016/0303091 A1 | 10/2016 | Wang |
| 2016/0348147 A1 | 12/2016 | Lopez et al. |
| 2016/0355802 A1 | 12/2016 | Isaacs et al. |
| 2017/0088670 A1 | 3/2017 | Rowan et al. |
| 2017/0166621 A1 | 6/2017 | Boettcher et al. |
| 2017/0170142 A1 | 6/2017 | Edelstein et al. |
| 2017/0189545 A1 | 7/2017 | Lee et al. |
| 2017/0233714 A1 | 8/2017 | Chilkoti et al. |
| 2017/0239363 A1 | 8/2017 | Chilkoti et al. |
| 2017/0369651 A1 | 12/2017 | Cheng et al. |
| 2018/0135060 A1 | 5/2018 | Romero Ramos et al. |
| 2018/0161772 A1 | 6/2018 | Rammohan et al. |
| 2018/0171337 A1 | 6/2018 | O'Neill et al. |
| 2018/0200196 A1 | 7/2018 | Fahmy et al. |
| 2018/0217136 A1 | 8/2018 | Chilkoti et al. |
| 2018/0231469 A1 | 8/2018 | Gibbons et al. |
| 2018/0238864 A1 | 8/2018 | Burd et al. |
| 2018/0258157 A1 | 9/2018 | Chilkoti et al. |

(56) References Cited

U.S. PATENT DOCUMENTS

| | | |
|---|---|---|
| 2018/0326044 A1 | 11/2018 | Carter |
| 2018/0327752 A1 | 11/2018 | Pillay et al. |
| 2018/0369399 A1 | 12/2018 | Hershfield et al. |
| 2019/0016763 A1 | 1/2019 | Kitazawa et al. |
| 2019/0204309 A1 | 7/2019 | Gibbs |
| 2019/0285623 A1 | 9/2019 | Chilkoti et al. |
| 2019/0292549 A1 | 9/2019 | Zhang et al. |
| 2019/0345228 A1 | 11/2019 | Chilkoti et al. |
| 2020/0030496 A1 | 1/2020 | Reddy et al. |
| 2020/0078313 A1 | 3/2020 | Roy et al. |
| 2020/0121809 A1 | 4/2020 | Hope et al. |
| 2020/0148724 A1 | 5/2020 | Chilkoti et al. |
| 2020/0163878 A1 | 5/2020 | Baumhof et al. |
| 2020/0181555 A1 | 6/2020 | Hinojosa et al. |
| 2021/0128734 A1 | 5/2021 | Chilkoti et al. |
| 2021/0154143 A1 | 5/2021 | Chilkoti et al. |
| 2023/0225998 A1 | 7/2023 | Mansour et al. |

FOREIGN PATENT DOCUMENTS

| | | |
|---|---|---|
| CA | 2423488 A1 | 4/2002 |
| CN | 102575229 A | 7/2012 |
| CN | 104725628 B | 4/2018 |
| CN | 112961065 A | 6/2021 |
| EP | 1670315 B1 | 4/2017 |
| EP | 2664340 B1 | 2/2020 |
| JP | 2014-156428 A | 8/2014 |
| JP | 2014-534265 A | 12/2014 |
| WO | WO1991/019813 A1 | 12/1991 |
| WO | WO2003/040165 A2 | 10/2002 |
| WO | WO2004/096124 A2 | 11/2004 |
| WO | WO2006/004778 A2 | 1/2006 |
| WO | 2006/110292 A2 | 10/2006 |
| WO | WO2007/073486 A2 | 6/2007 |
| WO | WO2007/108013 A2 | 9/2007 |
| WO | WO2007/134245 A2 | 11/2007 |
| WO | WO2008/012543 A1 | 1/2008 |
| WO | WO2008/030968 A2 | 3/2008 |
| WO | WO2009/067584 A1 | 5/2009 |
| WO | WO2010/054699 A1 | 5/2010 |
| WO | WO2010/057154 A1 | 5/2010 |
| WO | WO2010/096422 A1 | 8/2010 |
| WO | WO2011/025572 A1 | 3/2011 |
| WO | WO2011/123813 A2 | 10/2011 |
| WO | 2012/156058 A1 | 11/2012 |
| WO | 2012/162426 A1 | 11/2012 |
| WO | WO2013/049234 A2 | 4/2013 |
| WO | WO2013/065009 A1 | 5/2013 |
| WO | 2013/106715 A1 | 7/2013 |
| WO | WO2014/037373 A1 | 3/2014 |
| WO | WO2014/194244 A1 | 12/2014 |
| WO | 2015/011231 A1 | 1/2015 |
| WO | WO2015/130846 A2 | 9/2015 |
| WO | 2016/065300 A1 | 4/2016 |
| WO | WO2016/065273 A1 | 4/2016 |
| WO | WO2016/090103 A1 | 6/2016 |
| WO | WO2016/154530 A1 | 9/2016 |
| WO | WO2017/015132 A1 | 1/2017 |
| WO | WO2017/024182 A1 | 2/2017 |
| WO | WO2017/112825 A2 | 6/2017 |
| WO | WO2017/112826 A2 | 6/2017 |
| WO | WO2017/192449 A1 | 11/2017 |
| WO | WO2018/115401 A1 | 6/2018 |
| WO | WO2018/144854 A1 | 8/2018 |
| WO | 2019/103744 A1 | 5/2019 |
| WO | WO2019/147954 A1 | 8/2019 |
| WO | 2020/037100 A1 | 2/2020 |
| WO | 2020/037214 A1 | 2/2020 |
| WO | 2020/051223 A1 | 3/2020 |
| WO | 2020/160472 A1 | 8/2020 |
| WO | 2021/178898 A1 | 9/2021 |
| WO | 2022/016089 A2 | 1/2022 |
| WO | 2022/178438 A1 | 8/2022 |
| WO | 2022/066635 A1 | 3/2023 |

OTHER PUBLICATIONS

AACR, "AACR Cancer Progress Report 2016," Clin Cancer Res, Oct. 2016, vol. 22, Issue 19, 143 pages.

Aaron et al., "Elastin as a Random-Network Elastomer—a Mechanical and Optical Analysis of Single Elastin Fibers," Biopolymers, 1981, 20(6):1247-1260.

Abbruzzese et al., "A phase I clinical, plasma, and cellular pharmacology study of gemcitabine," J. Clin. Oncol. 1991, 3, 491-498.

Adams et al., "Safety and utilization of blood components as therapeutic delivery systems," Curr Pharm Biotechnol, 2003, 4(5): 275-82.

Adams et al., "Sustained release of antibiotics from injectable and thermally responsive polypeptide depots," J Biomed Mater Res B Appl Biomater, Jul. 2009, vol. 90B, Issue 1, pp. 67-74.

Adamska et al., "Pancreatic ductal adenocarcinoma: Current and evolving therapies," J Mol Sci, Jun. 2017, vol. 18, Issue 7, pp. 1338-1380.

Adiseshaiah et al., "Nanomedicine strategies to overcome the pathophysiological barriers of pancreatic cancer," Nat Rev Clin Oncol, Dec. 2016, vol. 13, Issue 12, pp. 750-765.

Aladini et al., "Chemical Synthesis and Characterization of Elastin-Like Polypeptides (ELPs) With Variable Guest Residues," J Pept Sci, May 2016, vol. 22, Issue 5, pp. 334-342.

Alarcon et al., "Exendin 4 controls insulin production in rat islet beta cells predominantly by potentiation of glucose-stimulated proinsulin biosynthesis at the translational level," Diabetologia, 2006, 49(12):2920-2929.

Albanese et al., "The effect of nanoparticle size, shape, and surface chemistry on biological systems," Annu. Rev. Biomed. Eng., Aug. 2012, vol. 14, pp. 1-16.

Alconcel et al., "FDA-approved poly(ethylene glycol)-protein conjugate drugs," Polym. Chem., vol. 2, Apr. 2011, Issue 7, pp. 1442-1448.

Allen et al., "Liposomal drug delivery systems: from concept to clinical applications," Adv Drug Deliv Rev, Elsevier, Jan. 2013, 65(1):36-48.

Alley et al., "Feasibility of drug screening with panels of human tumor cell lines using a microculture tetrazolium assay," Cancer Res., 1988, 48, 589-601.

Aluri et al., "Elastin-like peptide amphiphiles Form nanofibers with tunable length," Biomacromolecules, Sep. 2012, vol. 13, Issue 9, pp. 2645-2654.

American Diabetes Association, Standards of medical care in diabetes—2018. Diabetes Care, Jan. 2018, vol. 41, Supplement 1, pp. S1-S159.

Amiram et al., "A depot-forming glucagon-like peptide-1 fusion protein reduces blood glucose for five days with a single injection," J. Control. Release, Nov. 2013, vol. 172, Issue, pp. 144-151.

Amiram et al., "Injectable protease-operated depots of glucagon-like peptide-1 provide extended and tunable glucose control," Proc. Natl. Acad. Sci., Feb. 2013, vol. 110, Issue 8, pp. 2792-2797.

Andersen et al., "Extending Half-life by Indirect Targeting of the Neonatal Fc Receptor (FcRn) Using a Minimal Albumin Binding Domain," Journal of Biological Chemistry, Feb. 2011, vol. 286, Issue 7, pp. 5234-5241.

Anselmo et al., "Nanoparticles in the clinic," Bioeng Transl Med, Jun. 2016, 1(1):10-29.

Antos et al., "Lipid Modification of Proteins through Sortase-Catalyzed Transpeptidation," J. Am. Chem. Soc., Dec. 2008, vol. 130, Issue 48, pp. 16338-16343.

Antos et al., "Site-Specific N- and C-Terminal Labeling of a Single Polypeptide Using Sortases of Different Specificity," J. Am. Chem. Soc., Aug. 2009, vol. 131, Issue 31, pp. 10800-10801.

Arami et al., "In vivo delivery, pharmacokinetics, biodistribution and toxicity of iron oxide nanoparticles," Chem Soc Rev, Dec. 2015, 44(23):8576-8607.

Arias et al., "Superior preclinical efficacy of gemcitabine developed as chitosan nanoparticulate system," Biomacromolecules, Jan. 2011, vol. 12, Issue 1, pp. 97-104.

Armstrong et al., "Antibody against poly(ethylene glycol) adversely affects PEG-asparaginase therapy in acute lymphoblastic leukemia patients," Cancer, Jul. 2007, vol. 110, Issue 1, pp. 103-111.

(56) References Cited

OTHER PUBLICATIONS

Armstrong et al., "The Hydrodynamic Radii of Macromolecules and Their Effect on Red Blood Cell Aggregation," Biophys. J., 2004, 87, 4259-4270.
Arner et al., "FGF21 attenuates lipolysis in human adipocytes—a possible link to improved insulin sensitivity," FEBS Lett, May 2008, vol. 582, Issue 12, pp. 1725-1730.
Arnida et al., "Geometry and surface characteristics of gold nanoparticles influence their biodistribution and uptake by macrophages," Eur J Pharm Biopharm, Apr. 2011, vol. 77, Issue 3, pp. 417-423.
Asai et al., "Protein polymer hydrogels by in situ, rapid and reversible self-gelation," Biomaterials, Jul. 2012, vol. 33, Issue 21, pp. 5451-5458.
Astete et al., "Synthesis and characterization of PLGA nanoparticles," Journal of Biomaterials Science, Polymer Edition 2006, 17(3):247-289.
Atun et al., "Expanding global access to radiotherapy," Lancet Oncol, Sep. 2015, vol. 16, Issue 10, pp. 1153-1186.
Averick et al., "ATRP under biologically relevant conditions: grafting from a protein," ACS Macro. Lett., Jan. 2012, vol. 1, Issue 1, pp. 6-10.
Averick et al., "Protein-polymer hybrids: conducting ARGET ATRP from a genetically encoded cleavable ATRP initiator," Eur. Polym. J., Oct. 2013, vol. 49, Issue 10, pp. 2919-2924.
Awai et al., "Studies of the metabolism of I-131-labeled human transferrin," J. Lab. Clin. Med. 61, 1963, 363-396.
Awasthi et al., "Comparative benefits of Nab-paclitaxel over gemcitabine or polysorbate-based docetaxel in experimental pancreatic cancer," Carcinogenesis, Oct. 2013, vol. 34, Issue 10, pp. 2361-2369.
Awasthi et al., "Evaluation of combination treatment benefits of nab-paclitaxel in experimental pancreatic cancer," Journal of Clinical Oncology, 2012, 30, 170.
Axup et al., "Synthesis of site-specific antibody-drug conjugates using unnatural amino acids," Proc Natl Acad Sci USA, Feb. 2012, vol. 109, Issue 40, pp. 16101-16106.
Azhdarinia et al., "Regional radiochemotherapy using in situ hydrogel," Pharm Res., 2005, 22, 776-783.
Babu, "The contribution of intrinsically disordered regions to protein function, cellular complexity, and human disease," Biochem Soc Trans, Oct. 2016, 44(5):1185-1200.
Bache et al., "Investigating the accuracy of microstereotactic-body-radiotherapy utilizing anatomically accurate 3D printed rodent-morphic dosimeters," Medical Physics, Feb. 2015, vol. 42, Issue 2, pp. 846-855.
Badi, "Non-linear PEG-based thermoresponsive polymer systems," Progress in Polymer Science, Mar. 2017, vol. 66, pp. 54-79.
Bae et al., "Targeted drug delivery to tumors: myths, reality and possibility," J Control Release, Elsevier, Aug. 2011, 153(3):198-205.
Baggio et al., "A recombinant human glucagon-like peptide (GLP)-1-albumin protein (Albugon) mimics peptidergic activation of GLP-1 receptor-dependent pathways coupled with satiety, gastrointestinal motility, and glucose homeostasis," Diabetes 53, 2004, 2492-2500.
Baggio et al., "Biology of Incretins: GLP-1 and GIP," Gastroenterology, May 2007, vol. 132, Issue 6, pp. 2131-2157.
Bailey et al., "Genomic analyses identify molecular subtypes of pancreatic cancer," Nature, Mar. 2016, vol. 531, Issue 7592, pp. 47-52.
Balu et al., "An16-resilin: an advanced multi-stimuli-responsive resilin-mimetic protein polymer," Acta Biomater, Nov. 2014, 10:4768-4777.
Bamford et al., "The COSMIC (Catalogue of Somatic Mutations in Cancer) database and website," British Journal of Cancer, 2004, 91, 355-358.
Banani et al., "Biomolecular condensates: organizers of cellular biochemistry," Nat Rev Mol Cell Biol, May 2017, 18(5):285-298.
Banerjee et al., "Nanoparticles in cancer chemotherapy," Prog Mol Biol Transl Sci, Elsevier, Nov. 2011, 104:489-507.
Banga et al., "Parenteral controlled delivery and parmacokinetics of therapeutic peptides and proteins," (CRC Press, Boca Raton, FL, 2005).
Banjade et al., "Phase transitions of multivalent proteins can promote clustering of membrane receptors," Elife, Oct. 2014, 3:e04123.
Bansal et al., "PEGylation improves pharmacokinetic profile, liver uptake and efficacy of Interferon gamma in liver fibrosis," J. Control. Release, Sep. 2011, vol. 154, Issue 3, pp. 233-240.
Banskota et al., "Genetically encoded stealth nanoparticles of a zwitterionic polypeptide-paclitaxel conjugate have wider therapeutic window than Abraxane in multiple tumor models," Nano Lett, Mar. 2020, 20(4):2396-2409.
Barbuti et al., "Paclitaxel through the ages of anticancer therapy: Exploring its role in chemoresistance and radiation therapy," Cancers, Dec. 2015, vol. 7, Issue 4, pp. 2360-2371.
Barnett et al., "Normal tissue reactions to radiotherapy: towards tailoring treatment dose by genotype," Nat Rev Cancer, Feb. 2009, vol. 9, Issue 2, pp. 134-142.
Barton et al., "Estimating the demand for radiotherapy form the evidence: A review of changes from 2003 to 2012," Radiother Oncol, Jul. 2014, vol. 112, Issue 1, pp. 140-144.
Baskar et al., "Cancer and Radiation Therapy: Current Advances and Future Directions," Int. J. Med. Sci., Feb. 2012, vol. 9, Issue 3, pp. 193-199.
Bates et al., "Block copolymer thermodynamics: theory and experiment," Annu Rev. Phys. Chem., 1990, 41:525-57.
Bedford et al., "WW domain-mediated interactions reveal a spliceosome-associated protein that binds a third class of proline-rich motif: The proline glycine and methionine-rich motif," PNAS, 1998, 95: 10602-10607.
Beenken et al., "The FGF family: biology, pathophysiology and therapy," Nat Rev Drug Discov, Mar. 2009, vol. 8, Issue 3, pp. 235-253.
Begg et al., "Strategies to improve radiotherapy with targeted drugs," Nat Rev Cancer, Apr. 2011, vol. 11, Issue 4, pp. 239-253.
Bellucci et al., "A noncanonical function of sortase enables site-specific conjugation of small molecules to lysine residues in proteins," Angew. Chem. Int. Ed. 54, Jan. 2015, vol. 54, Issue 2, pp. 441-445.
Bellucci et al., "Three-in-One Chromatography-Free Purification, Tag Removal, and Site-Specific Modification of Recombinant Fusion Proteins Using Sortase A and Elastin-like Polypeptides," Angewandte Chemie International Edition, Mar. 2013, vol. 52, Issue 13, pp. 3703-3708.
Bender et al., "Synthesis, Crystallization, and Biological Evaluation of an Orally Active Prodrug of Gemcitabine," J. Med. Chem., Nov. 2009, vol. 52, Issue 22, pp. 6958-6961.
Berisio et al., "Imino Acids and Collagen Triple Helix Stability: Characterization of Collagen-like Polypeptides Containing Hyp-Hyp-Gly Seqeucne Repeats," JACS, 2004, 126: 11402-11403.
Bernacki et al., "Length-dependent aggregation of uninterrupted polyalanine peptides," Biochemistry, Sep. 2011, vol. 50, Issue 43, pp. 9200-9211.
Berndt et al., "Synthetic lipidation of peptides and amino acids: Monolayer structure and properties," J. Am. Chem. Soc., 1995, 117, 9515-9522.
Bessa et al., "Thermoresponsive self-assembled elastin-based nanoparticles for delivery of BMPs," Journal of Controlled Release, Mar. 2010, vol. 142, Issue 3, pp. 312-318.
Best, "Computational and theoretical advances in studies of intrinsically disordered proteins," Curr Opin Struct Biol, Feb. 2017, 42:147-154.
Bhattacharyya et al., "A paclitaxel-loaded recombinant polypeptide nanoparticle outperforms Abraxane in multiple murine cancer models," Nat. Commun., Aug. 2015, Issue 6, Article 7939, 30 pages.
Bhattacharyya et al., "Encapsulating a Hydrophilic Chemotherapeutic into Rod-Like Nanoparticles of a Genetically Encoded Asymmetric Triblock Polypeptide Improves its Efficacy," Advanced functional materials, Mar. 2017, vol. 27, Issue 12, Article 1605421, 9 pages.
Bidwell et al., "Development of elastin-like polypeptide for thermally targeted delivery of doxorubicin," Biochemical Pharmacology, Mar. 2007, vol. 73, Issue 5, pp. 620-631.
Binz et al., "Engineering novel binding proteins from nonimmunoglobulin domains," Nat Biotechnol, 2005, 23(10):1257-68.

(56) References Cited

OTHER PUBLICATIONS

Blanco et al., "Principles of nanoparticle design for overcoming biological barriers to drug delivery," Nat Biotechnol, Sep. 2015, 33(9):941-51.
Blasko et al., "Brachytherapy for carcinoma of the prostate: Techniques, patient selection, and clinical outcomes," Seminars in Radiation Oncology, 2002, 12, 81-94.
Blasko et al., "The role of external beam radiotherapy with I-125/Pd-103 brachytherapy for prostate carcinoma," Radiother Oncol, 2000, 57, 273-278.
Blasko et al., "Transperineal percutaneous iodine-125 implantation for prostatic carcinoma using transrectal ultrasound and template guidance," Endocurietherapy/Hyperthermia Oncology, 1987, 3, 131-139.
Bley et al., "Microtubule stabilising agents and ionising radiation: Multiple exploitable mechanisms for combined treatment," Eur J Cancer, Jan. 2013, vol. 49, Issue 1, pp. 245-253.
Bobo et al., "Nanoparticle-based medicines: a review of FDA-approved materials and clinical trials to date." Pharmaceutical research, Oct. 2016, vol. 33, Issue 10, pp. 2373-2387.
Bocci et al., "The pharmacological bases of the antiangiogenic activity of paclitaxel," Angiogenesis, Jul. 2013, vol. 16, Issue 3, pp. 481-492.
Bochicchio et al., "Investigating by CD the molecular mechanism of elasticity of elastomeric proteins," Chirality, Sep. 2008, vol. 20, Issue 9, pp. 985-994.
Boekhorst et al., "Genome-wide detection and analysis of cell wall-bound proteins with LPxTG-like sorting motifs," J. Bacteriol. 187, 2005, 4928-4934.
Boeynaems et al., "Protein Phase Separation: A New Phase in Cell Biology," Trends Cell Biol, Jun. 2018, 28(6):420-435.
Boldt, "Use of albumin: an update," Br J. Anaesth., Mar. 2010, vol. 104, Issue 3, pp. 276-284.
Bond, "Exenatide (Byetta) as a novel treatment option for type 2 diabetes mellitus," Proc. (Bayl. Univ. Med. Cent.), Jul. 2006, vol. 19, Issue 3, pp. 281-284.
Bontempo et al., "Streptavidin as a macroinitiator for polymerization: in situ protein-polymer conjugate formation," J. Am. Chem. Soc., 2005, 6508-6509.
Borst et al., "The Therapeutic Antibody LM609 Selectively Inhibits Ligand Binding to Human $\alpha V\beta 3$ Integrin via Steric Hindrance," Structure, Nov. 2017, 25(11):1732-1739.e5.
Bowditch et al., "Identification of a novel integrin binding site in fibronectin. Differential utilization by $\beta 3$ integrins," Journal of Biological Chemistry, 1994, 269(14):10856-10863.
Boyer et al., "Well-Defined Protein-Polymer Conjugates via in Situ RAFT Polymerization," J. Am. Chem. Soc., Jun. 2007, vol. 129, Issue 22, pp. 7145-7154.
Branco et al., "Self-assembling materials for therapeutic delivery," Acta Biomaterialia, Mar. 2009, vol. 5, Issue 3, pp. 817-831.
Brangwynne et al., "Polymer physics of intracellular phase transitions," Nature Physics, Nov. 2015, 11(11):899-904.
Brannon-Peppas et al., "Nanoparticle and targeted systems for cancer therapy," Advanced Drug Delivery Reviews, Elsevier, Sep. 2012, 64(11):206-212.
Broome et al., "Expanding the utility of beta-galactosidase complementation: piece by piece," Mol Pharm, ACS Publications, Feb. 2010, 7(1):60-74.
Broyer et al., "Emerging synthetic approaches for protein-polymer conjugations," Chem. Commun., Feb. 2011, vol. 47, Issue 8, pp. 2212-2226.
Brusa et al., "Antitumor activity and pharmacokinetics of liposomes containing lipophilic gemcitabine prodrugs," Anticancer Res., Jan. 2007, vol. 27, Issue 1A, pp. 195-199.
Burchard, "Light Scattering Techniques," Physical techniques for the study of food biopolymers, 1994, 151-213.
Burke et al., "Multimodal nanoparticle imaging agents: design and applications," Philos Trans A Math Phys Eng Sci, Nov. 2017, 375:20170261.
Burnouf, "Modern plasma fractionation," Transfus. Med. Rev., Apr. 2007, vol. 21, Issue 2, pp. 101-117.
Buteau et al., "Glucagon-like peptide-1 prevents beta cell glucolipotoxicity," Diabetologia, 2004, 47(5):806-815.
Butler et al., "$\beta$-Cell Deficit and Increased $\beta$-Cell Apoptosis in Humans With Type 2 Diabetes," Diabetes, 2003, 52(1):102-110.
Cabral et al., "Accumulation of sub-100 nm polymeric micelles in poorly permeable tumours depends on size," Nature Nanotechnology, Oct. 2011, vol. 6, Issue 12, pp. 815-823.
Cabrera et al., "Automated, High-Throughput Assays for Evaluation of Human Pancreatic Islet Function," Cell Transplant, First published Nov. 2007, vol. 16, Issue 10, pp. 1039-1048.
Cabrera et al., "Glutamate Is a Positive Autocrine Signal for Glucagon Release," Cell Metab, Jun. 2008, vol. 7, Issue 6, pp. 545-554.
Cai et al., "Long-acting preparations of exenatide," Drug Des. Devel. Ther., Sep. 2013, vol. 7, pp. 963-970.
Caliceti et al., "Pharmacokinetic and biodistribution properties of poly(ethylene glycol)-protein conjugates," Adv. Drug Deliv. Rev, 2003, 55, 1261-1277.
Callahan et al., "Triple stimulus-responsive polypeptide nanoparticles that enhance intratumoral spatial distribution," Nano Letters, Mar. 2012, vol. 12, Issue 4, pp. 2165-2170.
Camilloni et al., "Determination of secondary structure populations in disordered states of proteins using nuclear magnetic resonance chemical shifts," Biochemistry, Feb. 2012, vol. 51, Issue 11, pp. 2224-2231.
Campbell et al., "Pegylated peptides V. Carboxy-terminal PEGlyted analogs of growth hormone-releasing factor (GRF) display enhanced duration of biological activity in vivo," J. Peptide Res., 1997, 49:527-537.
Cao et al., "Monitoring the effects of anti-angiogenesis on the radiation sensitivity of pancreatic cancer xenografts using dynamic contrast-enhanced computed tomography," Int J Radiation Oncol Biol Phys, Feb. 2014, vol. 88, Issue 2, pp. 412-418.
Cardenes et al., "Locally advanced pancreatic cancer: Current therapeutic approach," The Oncologist, Jun. 2006, vol. 11, Issue 6, pp. 612-623.
Carreiras et al., "Expression and localization of alpha v integrins and their ligand vitronectin in normal ovarian epithelium and in ovarian carcinoma," Gynecol Oncol, 1996, 62(2):260-7.
Carrico et al., "Introducing genetically encoded aldehydes into proteins," Nat Chem Biol, Jun. 2007, vol. 3, Issue 6, pp. 321-322.
Cataldo et al., "Radiation-induced crosslinking of collagen gelatin into a stable hydrogel," Journal of Radioanalytical and Nuclear Chemistry, Sep. 2008, vol. 275, Issue 1, pp. 125-131.
Centers for Disease Control and Prevention, "National Diabetes Statistics Report, 2017," Atlanta, GA: Centers for Disease Control and Prevention, US Department of Health and Human Services; 2017. Reviewed: Feb. 24, 2018.
Ceska et al., "A new and rapid method for the clinical determination of $\alpha$-amylase activities in human serum and urine. Optimal conditions," Clinica Chimica Acta, 1969, 26, 437-444.
Chakrabartty et al., "Stability of $\alpha$-Helices," Adv Protein Chem, 1995, 46, 141-176.
Champion et al., "Particle shape: a new design parameter for micro- and nanoscale drug delivery carriers," J Control Release, Elsevier, Aug. 2007, 121(1-2):3-9.
Champion et al., "Role of particle size in phagocytosis of polymeric microspheres," Pharm Res, Srpinger, Mar. 2008, 25(8):1815-21.
Champion et al., "Role of target geometry in phagocytosis," Proc Natl Acad Sci U S A, The National Academy of Sciences of the USA, Mar. 2006, 103(13):4930-4.
Champion et al., "Shape induced inhibition of phagocytosis of polymer particles," Pharm Res, Springer, Jan. 2009, 26(1):244-9.
Chang et al., "Tumor-stroma interaction in orthotopic primary pancreatic cancer xenografts during hedgehog pathway inhibition," Int. J. Cancer, Jul. 2013, vol. 133, Issue 1, pp. 225-235.
Chatterjee et al., "Type 2 diabetes," The Lancet, Jun. 2017, vol. 389, Issue 10085, pp. 2239-2251.
Chaudhury et al., "The major histocompatibility complex-related Fc receptor for IgG (FcRn) binds albumin and prolongs its lifespan," J Exp Med, 2003, 197(3): p. 315-22.

(56) References Cited

OTHER PUBLICATIONS

Chen et al., "Anisotropic hydrogels fabricated with directional freezing and radiation-induced polymerization and crosslinking method," Materials Letters, Dec. 2012, vol. 89, pp. 104-107.
Chen et al., "Anti-hypervariable region antibody induced by a defined peptide: An approach for studying the structural correlates of idiotypes," PNAS, 1984, 81:1784-1788.
Chen et al., "Bioinspired Modular Synthesis of Elastin-Mimic Polymers To Probe the Mechanism of Elastin Elasticity," J. Am. Chem. Soc., Mar. 2010, vol. 132, Issue 13, pp. 4577-4579.
Chen et al., "Rheology of Soft Materials," Annual Review of Condensed Matter Physics, May 2010, vol. 1, pp. 301-322.
Chen et al., "Site-specific labeling of cell surface proteins with biophysical probes using biotin ligase," Nat Methods, 2005, 2(2):99-104.
Chen et al., "The use of self-adjuvanting nanofiber vaccines to elicit high-affinity B cell responses to peptide antigens without inflammation," Biomaterials, Nov. 2013, vol. 34, Issue 34, pp. 8776-8785.
Chen, "Small-molecule delivery by nanoparticles for anticancer therapy," Trends Mol Med, Cell Press, Dec. 2010, 16(12):594-602.
Chilkoti et al., "Design of thermally responsive, recombinant polypeptide carriers for targeted drug delivery," Advance Drug Delivery Reviews, 2002, 54:1093-1111.
Chilkoti et al., "Stimulus responsive elastin biopolymers: applications in medicine and biotechnology," Curr Opin Chem Biol, Dec. 2006, vol. 10, Issue 6, pp. 652-657.
Chilkoti et al., "Targeted drug delivery by thermally responsive polymers," Advanced Drug Delivery Reviews, 2002, 54:613-630.
Chithrani et al., "Determining the size and shape dependence of gold nanoparticle uptake into mammalian cells," Nano Lett, Apr. 2006, vol. 6, Issue 4, pp. 662-668.
Chithrani et al., "Elucidating the mechanism of cellular uptake and removal of protein-coated gold nanoparticles of different sizes and shapes," Nano letters, ACS Publications, Jun. 2007, 7(6):1542-1550.
Chitkara et al., "Self-Assembling, Amphiphilic Polymer-Gemcitabine Conjugate Shows Enhanced Antitumor Efficacy Against Human Pancreatic Adenocarcinoma," Bioconjug. Chem., Jun. 2013, vol. 24, Issue 7, pp. 1161-1173.
Cho et al., "Effects of hofmeister anions on the phase transition temperature of elastin-like polypeptides," J. Phys. Chem. B., Nov. 2008, vol. 112, Issue 44, pp. 13765-13771.
Cho et al., "Hydrogen bonding of β-turn structure is stabilized in D(2)O," J Am Chem Soc, Oct. 2009, vol. 131, Issue 42, pp. 15188-15193.
Cho et al., "Therapeutic nanoparticles for drug delivery in cancer," Clin. Cancer Res., Mar. 2008, vol. 14, Issue 5, pp. 1310-1316.
Chockalingam et al., "Design and application of stimulus-responsive peptide systems," Protein Engineering, Design & Selection, Apr. 2007, 20(4):155-161.
Choi et al., "Renal Clearance of Nanoparticles," Nature biotechnology, Oct. 2007, vol. 25, Issue 10, pp. 1165-1170.
Chow et al., "Peptide-based biopolymers in biomedicine and biotechnology," Mater. Sci. Eng. R Reports, Jan. 2008, vol. 62, Issue 4, pp. 125-155.
Chow et al., "Ultra-High Expression of a Thermally Responsive Recombinant Fusion Protein in E. coli," Biotechnology Progress, Sep. 2006, vol. 22, Issue 3, pp. 638-646.
Choy et al., "Investigation of taxol as a potential radiation sensitizer," Cancer, 1993, 71, 3774-3778.
Christensen et al., "Fusion order controls expression level and activity of elastin-like polypeptide fusion proteins," Protein Science, Jul. 2009, vol. 18, Issue 7, pp. 1377-1387.
Christensen et al., "Predicting Transition Temperatures of Elastin-Like Polypeptide Fusion Proteins," Biomacromolecules, Mar. 2013, vol. 14, Issue 5, pp. 1514-1519.
Cid-Arregui et al., "Perspectives in the treatment of pancreatic adenocarcinoma," World Journal of Gastroenterology, Aug. 2015, vol. 21, Issue 31, pp. 9297-9316.
Ciezki et al., "Brachytherapy or surgery? A composite view," Oncology, Oct. 2009, vol. 23, Issue 11, pp. 960-964.
Cima, "AVMA Guidelines for the Euthanasia of Animal: 2013 Edition," Journal of the American Veterinary Medical Association, Jan. 2013, vol. 242, 102 pages.
Cirulis et al., "Viscoelastic properties and gelation of an elastin-like polypeptide," Journal of Rheology, Sep. 2009, vol. 53, Issue 5, pp. 1215-1228.
Clarke et al., "Tropoelastin massively associates during coacervation to form quantized protein spheres," Biochemistry, Jul. 2006, vol. 45, Issue 33, pp. 9989-9996.
Clavé et al., "Amylase, lipase, pancreatic isoamylase, and phospholipase A in diagnosis of acute pancreatitis," Clinical Chemistry, 1995, 41, 1129-1134.
Coin et al., "Solid-phase peptide synthesis: from standard procedures to the synthesis of difficult sequences," Nat. Protoc., Dec. 2007, vol. 2, Issue 12, 3247-3256.
Colomb et al., "Radiation-Convertible Polymers from Norbornenyl Derivatives. Crosslinking with Ionizing Radiation," Journal of Applied Polymer Science, 1970, 14, 1659-1670.
Conner et al., "Regulated portals of entry into the cell," Nature, 2003, 422(6927):37-44.
Conrad et al., "ELPylated anti-human TNF therapeutic single-domain antibodies for prevention of lethal septic shock," Plant Biotechnology Journal, Jan. 2011, vol. 9, Issue 1, pp. 22-31.
Coskun et al., "Fibroblast Growth Factor 21 Corrects Obesity in Mice," Endocrinology, Dec. 2008, vol. 149, Issue 12, pp. 6018-6027.
Costa et al., "Active Targeting of Cancer Cells by Nanobody Decorated Polypeptide Micelle with Bio-orthogonally Conjugated Drug," Nano letters, Dec. 2018, 19(1):247-254.
Craik et al., "The future of peptide-based drugs," Chemical biology & drug design 81, Dec. 2013, vol. 81, Issue 1, pp. 136-147.
Cui et al., "Amino acid sequence in constitutionally isomeric tetrapeptide amphiphiles dictates architecture of one-dimensional nanostructures," J. Am. Chem. Soc., Aug. 2014, vol. 136, Issue 35, 12461-12468.
Cui et al., "Self-assembly of peptide amphiphiles: from molecules to nanostructures to biomaterials," Biopolymers, Jan. 2010, vol. 94, Issue 1, pp. 1-18.
Dai et al., "Versatile biomanufacturing through stimulus-responsive cell-material feedback," Nature chemical biology, Sep. 2019, 15(10):1017-1024.
Dalhaimer et al., "Single Molecule Visualization of Stable, Stiffness-Tunable, Flow-Conforming Worm Micelles," Macromolecules, 2003, 36(18):6873-6877.
Dalla Poza et al., "Targeting gemcitabine containing liposomes to CD44 expressing pancreatic adenocarcinoma cells causes an increase in the antitumoral activity," Biochim. Biophys. Acta, May 2013, vol. 1828, Issue 5, pp. 1396-1404.
Darzynkiewicz et al., "DNA content measurement for DNA ploidy and cell cycle analysis," Current Protocols in Cytometry, 2001, 7.5.1-7.5.24.
Das et al., "Conformations of intrinsically disordered proteins are influenced by linear sequence distributions of oppositely charged residues," Proc Natl Acad Sci U S A, National Academy of Sciences, Aug. 2013, 110(33):13392-13397.
Dasgupta et al., "Isopeptide Ligation Catalyzed by Quintessential Sortase A: Mechanistic Cues From Cyclic and Branched Oligomers of Indolicidin," The Journal of Biological Chemistry, May 2011, vol. 286, No. 27, pp. 23996-24006, Supplemental Information.
Day et al., "A new glucagon and GLP-1 co-agonist eliminates obesity in rodents," Nat Chem Biol, Oct. 2009, 5:749.
De et al., "Temperature-Regulated Activity of Responsive Polymer-Protein Conjugates Prepared by Grafting-from via RAFT Polymerization," J. Am. Chem. Soc. Jul. 2008, 130, 11288-11289.
De Simone et al., "Accurate random coil chemical shifts from an analysis of loop regions in native states of proteins," J Am Chem Soc, Nov. 2009, 131, 16332-16333.
Deer et al., "Phenotype and genotype of pancreatic cancer cell lines," Pancreas, May 2010, 39, 425-435.

(56) References Cited

OTHER PUBLICATIONS

Dejana et al., "The role of adherens junctions and VE-cadherin in the control of vascular permeability," J Cell Sci, Jul. 2008, 121, 2115-2122.
Delaglio et al., "NMRPipe: A multidimensional spectral processing system based on UNIX pipes," Journal of Biomolecular NMR 6, 1995, 277-293.
DeLisser et al., "Vascular endothelial platelet endothelial cell adhesion molecule 1(PECAM-1) regulates advanced metastatic progression," PNAS, Oct. 2010, 107, 18616-18621.
Dennis et al., "Albumin binding as a general strategy for improving the pharmacokinetics of proteins," J Biol Chem, 2002, 277(38): p. 35035-43.
Dennis et al., "Co-Translational Myristoylation Alters the Quaternary Structure of HIV-1 Nef in Solution," Proteins: Structure, Function, and Bioinformatics, 2005, 60:658-669.
Depp et al., "Native protein-initiated ATRP: A viable and potentially superior alternative to PEGylation for stabilizing biologics," Acta Biomater. Feb. 2009, 5, 560-569.
Deshayes et al., "Radium 223 dichloride for prostate cancer treatment," Drug Des Devel Ther, Sep. 2017, 11, 2643-2651.
DeYoung et al., "Encapsulation of exenatide in poly-(D,L-lactide-co-glycolide) microspheres produced an investigational long-acting once-weekly formulation for type 2 diabetes," Diabetes Technol Ther, Nov. 2011, 13, 1145-1154.
Diana et al., "Prognostic role and correlation of CA9, CD31, CD68 and CD20 with the desmoplastic stroma in pancreatic ductal adenocarcinoma," Oncotarget, Nov. 2016, 7, 72819-72832.
Diehl et al., "A Good Practice Guide to the Administration of Substances and Removal of Blood Including Routes and Volumes," J Appl Toxicol, 2001, 21, 15-23.
Dignon et al., "Relation between single-molecule properties and phase behavior of intrinsically disordered proteins," Proc Natl Acad Sci U S A, Oct. 2018, 115(40):9929-9934.
Dignon et al., "Sequence determinants of protein phase behavior from a coarse-grained model," PLoS Comput Biol, Jan. 2018, 14(1):e1005941.
Ding et al., "Mechanism for the alpha-helix to beta-hairpin transition," Proteins, 2003, 53, 220-228.
Ding et al., "βKlotho Is Required for Fibroblast Growth Factor 21 Effects on Growth and Metabolism," Cell Metab, Sep. 2012, 16(3):387-393.
Donnelly et al., "DNA Vaccines," Ann. Rev. Immunol., 1997, 15, 617-648.
Dreher et al., "Evaluation of an elastin-like polypeptide-doxorubicin conjugate for cancer therapy," J. of Controlled Release, 2003, 91:31-43.
Dreher et al., "Temperature triggered self-assembly of polypeptides into multivalent spherical micelles," J. Am. Chem. Soc. Jan. 2008, 130, 687-694.
Dreher et al., "Thermal cycling enhances the accumulation of a temperature-sensitive biopolymer in solid tumors," Cancer Res, May 2007, 67, 4418-4424.
Dreher, M. R. Ph.D. Thesis, Duke University, Durham, NC, Apr. 2006.
Dreis et al., "Preparation, Characterisation and Maintenance of Drug Efficacy of Doxorubicin-Loaded Human Serum Albumin (HSA) Nanoparticles," Int. J. Pharm., Aug. 2007, 341, 207-214.
Drucker "Mechanisms of Action and Therapeutic Application of Glucagon-like Peptide-1," Cell Metab, Apr. 2018, 27(4):740-756.
Drucker et al., "The incretin system: glucagon-like peptide-1 receptor agonists and dipeptidyl peptidase-4 inhibitors in type 2 diabetes," Lancet 368, Nov. 2006, 1696-1705.
Drucker, "Glucagon-like peptides," Diabetes 47, 1998, 159-169.
Drucker, "Incretin action in the pancreas: potential promise, possible perils, and pathological pitfalls," Diabetes, Oct. 2013, 62, 3316-3323.
Du et al., "Endoscope-assisted brachytherapy for pancreatic cancer: From tumor killing to pain relief and drainage," Journal of interventional gastroenterology, Jan. 2011, 1, 23-27.
Du et al., "Tailor-made dual pH-sensitive polymer-doxorubicin nanoparticles for efficient anticancer drug delivery," J. Am. Chem. Soc., Oct. 2011, 133, 17560-17563.
Duan et al., "Fibronectin type III domain based monobody with high activity," Biochemistry, Oct. 2007 46(44):12656-12664.
Duan et al., "Improving the thermostability and catalytic efficiency of *Bacillus deramificans* pullulanase by site-directed mutagenesis," Appl Environ Microbiol, American Society for Microbiology, Jul. 2013, 79(13):4072-4077.
Dubey et al., "Development and evaluation of folate functionalized albumin nanoparticles for targeted delivery of gemcitabine," Int J Pharm., Aug. 2015, 492(1-2):80-91.
Ducreux et al., "Radiation plus docetaxel and cisplatin in locally advanced pancreatic carcinoma: A non-comparative randomized phase II trial," Digestive and Liver Disease, Oct. 2014, 46, 950-955.
Duke University, "Gemcitabine/Nab-Paclitaxel With HIGRT in Resectable Pancreatic Cancer," Clinical Trial NCT02318095 <https://clinicaltrials.gov/ct2/show/NCT02318095> Webpage accessed Jan. 11, 2017.
Duncan, "The dawning era of polymer therapeutics," Nature Reviews Drug Discovery, 2003, 2, 347-360.
Duncan, R. "Polymer conjugates as anticancer nanomedicines," Nat. Rev. Cancer, Sep. 2006, 6, 688-701.
Duronio et al., "Protein N-myristoylation in *Escherichia coli*: Reconstitution of a eukaryotic protein modification in bacteria," Proc. Natl. Acad. Sci. USA, 1990, vol. 87, pp. 1506-1510.
Dyrberg et al., "Peptide as Atigens," J. Exp. Med., 1986, 164:1344-1349.
Dzuricky et al., "Avidity and Cell Uptake of Integrin Targeting Polypeptide Micelles is Strongly Shape Dependent," Nano letters, Sep. 2019, 19(9):6124-6132.
Dzuricky et al., "The Convergence of Artificial Protein Polymers and Intrinsically Disordered Proteins," Biochemistry, May 2018, 57(17):2405-2414.
Egan et al., "The Insulinotropic Effect of Acute Exendin-4 Administered to Humans: Comparison of Nondiabetic State to Type 2 Diabetes," The Journal of Clinical Endocrinology & Metabolism, 2002, 87, 1282-1290.
Ehlerding et al., "Biodegradable and Renal Clearable Inorganic Nanoparticles," Adv Sci (Weinh), Feb. 2016, 3(2):1500223.
Eisenhaber et al., "Prediction of lipid posttranslational modifications and localization signals from protein sequences: Big-Π, NMT and PTS1," Nucleic Acids Res., 2003, 31, 3631-3634.
Eisenhauer et al., "New response evaluation criteria in solid tumours: Revised RECIST guideline (version 1.1)," Eur J Cancer, Jan. 2009, 45(2):228-247.
El-Assaad et al., "Saturated Fatty Acids Synergize with Elevated Glucose to Cause Pancreatic β-Cell Death," Endocrinology, 2003, 144(9):4154-4163.
Elbaum-Garfinkle et al., "The disordered P granule protein LAF-1 drives phase separation into droplets with tunable viscosity and dynamics," Proc Natl Acad Sci U S A, Jun. 2015, 112(23):7189-7194.
Ellis, "Macromolecular crowding: obvious but underappreciated," Trends Biochem. Sci., 2001, 26 (10), 597-604.
Elsabahy et al., "Design of polymeric nanoparticles for biomedical delivery applications," Chem Soc Rev, Royal Society of Chemistry, Apr. 2012, 41(7):2545-61.
Elvin et al., "Synthesis and properties of crosslinked recombinant pro-resilin," Nature, 2005, 437(7061):999-1002.
Elzoghby et al., "Implications of Protein- and Peptide-Based Nanoparticles as Potential Vehicles for Anticancer Drugs," Advances in Protein Chemistry and Structural Biology, Academic Press, Elsevier, Mar. 2015, Chapter Six, vol. 98, pp. 169-221.
Engin et al., "Thermoradiotherapy in the management of superficial malignant tumors," Clinical Cancer Research, 1995, 1, 139-145.
Erickson-Miller et al., "Differential toxicity of camptothecin, topotecan and 9-aminocamptothecin to human, canine, and murine myeloid progenitors (CFU-GM) in vitro," Cancer Chemother. Pharmacol., 1997, 39 (5), 467-472.
Etrych et al., "HPMA Copolymer Conjugates of Paclitaxe; and Docetaxel with pH-Controlled Drug Release," Molecular Pharmaceutics, Jun. 2010, 7(4):1015-1026.

(56) References Cited

OTHER PUBLICATIONS

Falk et al., "Hyperthermia in oncology," Int J Hyperthermia, 2001, 17, 1-18.
Farazi et al., "Structures of *Saccharomyces cerevisiae* N-myristoyltransferase with bound myristoylCoA and peptide provide insights about substrate recognition and catalysis," Biochemistry, 2001, 40, 6335-6343.
Farmer et al., "Conformational behavior of chemically reactive alanine-rich repetitive protein polymers," Biomacromolecules, 2005, 6, 1531-1539.
Farokhzad et al., "Targeted nanoparticle-aptamer bioconjugates for cancer chemotherapy in vivo," Proc Natl Acad Sci U S A, The National Academy of Sciences of the USA, Apr. 2006, 103(16):6315-20.
Feng et al., "Protein resistant surfaces: comparison of acrylate graft polymers bearing oligo-ethylene oxide and phosphorylcholine side chains," Biointerphases, Mar. 2006, 1 (1), 50.
Fernandez-Colino et al., "Amphiphilic Elastin-Like Block Co-Recombinamers Containing Leucine Zippers: Cooperative Interplay between Both Domains Results in Injectable and Stable Hydrogels," Biomacromolecules, Sep. 2015, 16, 3389-3398.
Finan et al., "A rationally designed monomeric peptide triagonist corrects obesity and diabetes in rodents," Nat Med, Jan. 2015, 21:27-36.
Finan et al., "Unimolecular Dual Incretins Maximize Metabolic Benefits in Rodents, Monkeys, and Humans," Sci Transl Med, Oct. 2013, 5(209):209ra151.
Fluegel et al., "Chain stiffness of elastin-like polypeptides," Biomacromolecules, Oct. 2010, 11, 3216-3218.
Fosgerau et al., "Peptide therapeutics: current status and future directions," Drug Discovery Today, Jan. 2015, 20, 122-128.
Franzmann et al., "Phase separation of a yeast prion protein promotes cellular fitness," Science, Jan. 2018, 359(6371):eaao5654.
Free et al., "A Phase 1, multi-center, randomized, double-blind, placebo controlled study to evaluate the safety/tolerability, pharmacokinetic and hemodynamic response following single ascending subcutaneous doses of PB1046 (Vasomera) in subjects with essential hypertension," Circulation, Mar. 2018, 130:A19112.
Friedman et al., "Directed Evolution to Low Nanomolar Affinity of a Tumor-Targeting Epidermal Growth Factor Receptor-Binding Affibody Molecule," J. Mol. Biol., Mar. 2008, 376, 1388-1402.
Frilling et al., "Recommendations for management of patients with neuroendocrine liver metastases," The lancet oncology, Jan. 2014, 15, e8-21.
Fu et al., "Nanoparticle Albumin—Bond (NAB) Technology is a Promising Method for Anti-Cancer Drug Delivery," Recent Patents on Anti-Cancer Drug Discovery, Nov. 2009. 4(3):262-272.
Fujiwara et al., "Modulating effect of the PI3-kinase inhibitor LY294002 on cisplatin in human pancreatic cancer cells," Journal of Experimental & Clinical Cancer Research, Nov. 2008, 27, 76.
Furgeson et al., "Structural optimization of a "smart" doxorubicin-polypeptide conjugate for thermally targeted delivery to solid tumors," Journal of Controlled Release, Jan. 2006, 110:362-369.
Furumoto et al., "Effect of coupling of albumin onto surface of PEG liposome on its In vivo disposition," International Journal of Pharmaceutics, Mar. 2007, 329(1-2): p. 110-116.
Gaberc-Porekar et al., "Obstacles and pitfalls in the PEGylation of therapeutic proteins," Curr. Opin. Drug Discov. Devel. 11, Mar. 2008, 242-250.
Gabizon et al., "Prolonged circulation time and enhanced accumulation in malignant exudates of doxorubicin encapsulated in polyethylene-glycol coated liposomes," Cancer Res., Feb. 1994, 54, 987-992.
Gaich et al., "The Effects of LY2405319, an FGF21 Analog, in Obese Human Subjects with Type 2 Diabetes," Cell Metab, Sep. 2013, 18(3):333-340.
Ganson et al., "Control of hyperuricemia in subjects with refractory gout, and induction of antibody against poly(ethylene glycol) (PEG), in a phase I trial of subcutaneous PEGylated urate oxidase," Arthritis Res. Ther. 8, Feb. 2006, R12-R22.
Ganson et al., "Pre-existing anti-polyethylene glycol antibody linked to first-exposure allergic reactions to pegnivacogin, a PEGylated RNA aptamer," J Allergy Clin Immunol, May 2016, 137(5): 1610-1613, e1617.
Gao et al., "In situ growth of a PEG-like polymer from the C terminus of an intein fusion protein improves pharmacokinetics and tumor accumulation" PNAS Early Edition, Jul. 2010, vol. 107, 1-6.
Gao et al., "In situ growth of a PEG-like polymer from the C terminus of an intein fusion protein improves pharmacokinetics and tumor accumulation," Proc. Natl. Acad. Sci., Sep. 2010, 107(38):16432-16437.
Gao et al., "In situ growth of a stoichiometric PEG-like conjugate at a protein's N-terminus with significantly improved pharmacokinetics," Proc. Natl. Acad. Sci., Sep. 2009, 15231-15236.
Gao, "Site-specific and in situ growth of stealth polymer conjugates of proteins with significally improved pharmacology," Journal of Controlled Release, Nov. 2013, 172(1):e116-e117.
Garanger et al., "Structural Evolution of a Stimulus-Responsive Diblock Polypeptide Micelle by Temperature Tunable Compaction of its Core," Macromolecules, Sep. 2015, 48, 6617-6627.
Garay et al., "Antibodies against polyethylene glycol in healthy subjects and in patients treated with PEG-conjugated agents," Expert Opinion. Drug Deliv. 9, Nov. 2012, 1319-1323.
Garcia Quiroz et al., "Syntax of Phase Transition Peptide Polymers with LCST and UCST Behavior," Jan. 1, 2013, Retrieved from the Internet: URL:https://dukespace.lib.duke.edu/dspace/bitstream/handle/10161/7256/GarciaQuirozduke0066D_11972.pdf?sequence=1&isAllowed=y.
Gauthier et al., "Peptide/protein-polymer conjugates: synthetic strategies and design concepts," Chem. Commun., Jul. 2008, 2591-2611.
Ge et al., "Self-Cleavable Stimulus Responsive Tags for Protein Purification without Chromatography" J. Am. Chem. Soc., 2005, 127: 11228-11229.
Genbank Accession NM_001182082.1 (Mar. 2017).
Geng et al., Shape effects of filaments versus spherical particles in flow and drug delivery, Nat Nanotechnol, Nature Research, Apr. 2007, 2(4):249-55.
Ghoorchian et al., "Molecular architecture influences the thermally induced aggregation behavior of elastin-like polypeptides," Biomacromolecules, Oct. 2011, 12, 4022-4029.
Gianni et al., "Nonlinear pharmacokinetics and metabolism of paclitaxel and its pharmacokinetic/pharmacodynamic relationships in humans," J. Clin. Oncol., 1995, 13 (1), 180-190.
Giberti et al., "Radical retropubic prostatectomy versus brachytherapy for low-risk prostatic cancer: a prospective study," World J Urol, Oct. 2009, 27, 607-612.
Gibson et al., "Enzymatic assembly of DNA molecules up to several hundred kilobases," Nat Methods, May 2009, 6, 343-345.
Gilbreth et al., "Structural insights for engineering binding proteins based on non-antibody scaffolds," Curr Opin Struct Biol, Elsevier, Jun. 2012, 22(4):413-20.
Gillies et al., "Dendrimers and dendritic polymers in drug delivery," Drug Discovery Today, 2005, 10(1):35-43.
Gilroy et al., "Fusion of fibroblast growth factor 21 to a thermally responsive biopolymer forms an injectable depot with sustained anti-diabetic action," J Control Release, May 2018, 277:154-164.
Glassman et al., "Toughening of Thermoresponsive Arrested Networks of Elastin-Like Polypeptides To Engineer Cytocompatible Tissue Scaffolds," Biomacromolecules, Feb. 2016, 17, 415-426.
Gluck et al., "Single Vector System for Efficient N-myristoylation of Recombinant Proteins in *E. coli*," Plos One, Apr. 2010, 5(4) e100881.
Göke et al., "Exendin-4 is a high potency agonis and truncated exendin-(9-39)-amide an antagonist at the glucagon-like peptide 1-(7-36)-amide receptor of insulin-secreting b-cells," J. Biol. Chem. 268, 1993, 19650-19655.
Goldsmith et al., "Enzyme engineering: reaching the maximal catalytic efficiency peak," Curr Opin Struct Biol, Dec. 2017, 47:140-150.
Gordon et al., "Protein N-myristoylation," J. Biol. Chem., 1991, 266, 8647-8650.

(56) References Cited

OTHER PUBLICATIONS

Gosline et al., "Elastic proteins: biological roles and mechanical properties," Philos Trans R Soc Lond B Biol Sci, 2002, 357, 121-132.
Gottlieb et al., "NMR chemical shifts of common laboratory solvents as trace impurities," J. Org. Chem., 1997, 62, 7512-7515.
Goutelle et al., "The Hill equation: a review of its capabilities in pharmacological modelling. Fundam," Clin. Pharmacol. 22, Dec. 2008, 633-648.
Graff et al., "Theoretical analysis of antibody targeting of tumor spheroids: importance of dosage for penetration, and affinity for retention," Cancer Research, 2003, 63(6):1288-1296.
Gratton et al., "The effect of particle design on cellular internalization pathways," Proc Natl Acad Sci U S A, The National Academy of Sciences of the USA, Aug. 2008, 105(33):11613-8.
Greco et al., "The search for synergy: a critical review from a response surface perspective," Pharmacological Reviews, 1995, 24, 331-385.
Green et al., "Abraxane®, a novel Cremophor®-free, albumin-bound particle form of paclitaxel for the treatment of advanced non-small-cell lung cancer," Annals of Oncology, Aug. 2006, 17, 1263-1268.
Green et al., "Novel dipeptidyl peptidase IV resistant analogues of glucagon-like peptide-1(7-36) amide have preserved biological activities in vitro conferring improved glucose-lowering action in vivo" J. of Mol. Endocrin., 2003, 31(3): 529-540.
Greenfield, "Using circular dichroism spectra to estimate protein secondary structure," Nat. Protoc., Dec. 2006, 1(6):2876-90.
Grimm et al., "Advances in Brachytherapy," Reviews in Urology, 2004, 6, S37-S48.
Grover et al., "Protein-Polymer Conjugates: Synthetic Approaches by Controlled Radical Polymerizations & Interesting Applications", Curr Opin Chem Bioi., Dec. 2010; 14(6): 818-827.
Gu et al., "Enzymatic Synthesis of Nucleobase-Modified Single-Stranded DNA Offers Turnable Resistance to Nuclease Degradation," Biomacromolecules, Jul. 2018, 19, 3525-3535.
Gu et al., "Photocontrolled micellar aggregation of amphiphilic DNA-azobenzene conjugates," Colloids Surfaces B: Biointerfaces, Nov. 2015, 135, 126-132.
Gu et al., "Precise engineering of targeted nanoparticles by using self-assembled biointegrated block copolymers," Proc Natl Acad Sci U S A, The National Academy of Sciences of the USA, Feb. 2008, 105(7):2586-91.
Güngör et al., "Pancreatic cancer," British Journal of Pharmacology, Jan. 2014, 171, 849-858.
Guo et al., "Nanoparticles escaping RES and endosome: challenges for siRNA delivery for cancer therapy," J. Nanomaterials, Aug. 2011, 2011: 1-12.
Gustafsson, "Nonlinear structured-illumination microscopy: widefield fluorescence imaging with theoretically unlimited resolution," Proc Natl Acad Sci U S A, 2005, 102, 13081-13086.
Gustafsson, "Surpassing the lateral resolution limit by a factor of two using structured illumination microscopy," Short Communication. Journal of Microscopy, 2000, 198, 82-87.
Guzman et al., "Leiodermatolide, a novel marine natural product, has potent cytotoxic and antimitotic activity against cancer cells, appears to affect microtubule dynamics, and exhibits antitumor activity," Int. J. Cancer, Nov. 2016, 139, 2116-2126.
Ha et al., "Immunoglobulin Fc Heterodimer Platform Technology: From Design to Applications in Therapeutic Antibodies and Proteins," Front Immunol, Oct. 2016, 7(394) (in English).
Haider et al., "Genetically engineered polymers: Status and prospects for controlled release," J. Control. Release, 2004, 95, 1-26.
Halozyme Therapeutics, "PEGPH20 Plus Nab-Paclitaxel Plus Gemcitabine Compared With Nab-Paclitaxel Plus Gemcitabine in Subjects With Stage IV Untreated Pancreatic Cancer (HALO-109-202)," Clinical Trial NCT01839487 <https://clinicaltrials.gov/ct2/show/study/NCT01839487> Accessed May 29, 2018.

Hamada et al., "Novel therapeutic strategies targeting tumor-stromal interactions in pancreatic cancer," Frontiers in Physiology, Nov. 2013, vol. 4, Article 331, 7 pages.
Hamidi et al., "Pharmacokinetic Consequences of Pegylation," Drug Deliv., Dec. 2006, 13, 399-409.
Hamley, "Self-assembly of amphiphilic peptides," Soft Matter, Feb. 2011, 7, 4122.
Hampp et al., "Use of Antidiabetic Drugs in the U.S., 2003-2012," Diabetes Care, May 2014, 37: 1367-1374.
Han et al., "Survival of patients with advanced pancreatic cancer after iodine[125] seeds implantation brachytherapy: A meta-analysis," Medicine, Feb. 2017, 96, e5719.
Harmon et al., "A Model for Hysteresis Observed in Phase Transitions of Thermally Responsive Intrinsically Disordered Protein Polymers," Biophysical Journal, Feb. 2017, 112(3):207a.
Harries et al., "Nanoparticle Albumin-Bound Paclitaxel for Metastatic Breast Cancer," J. Clin. Oncol., 2005, 23(31):7768-7771.
Harris et al., "Pegylation," Clinical Pharmacokinetics, 2001, 40(7):539-551.
Hart et al., "Attenuation of FGF signalling in mouse β-cells leads to diabetes," Nature, 2000, 408:864.
Hartgerink et al., "Self-assembly and mineralization of peptide-amphiphile nanofibers," Science, 2001, 294, 1684-8.
Hassouneh et al., "Elastin-like Polypeptide Diblock Copolymers Self-Assemble into Weak Micelles," Macromolecules, Jun. 2015, 48, 4183-4195.
Hassouneh et al., "Elastin-Like Polypeptides as a Purification Tag for Recombinant Proteins," Curr Protoc Protein Sci., Aug. 2010, Chapter 6. Unit 6.11. 10.1002/0471140864.ps0611s61.
Hassouneh et al., "Fusions of elastin-like polypeptides to pharmaceutical proteins," Methods Enzymol., Jan. 2012, 502, 215-37.
Hassouneh et al., "Unexpected Multivalent Display of Proteins by Temperature Triggered Self-assembly of Elastin-like Polypeptide Block Copolymers," Biomacromolecules, Apr. 2012, vol. 13, Issue 4, pp. 1598-1605.
Hathout et al., "Analysis of seed loss and pulmonary seed migration in patients treated with virtual needle guidance and robotic seed delivery," American journal of clinical oncology, Oct. 2011, 34, 449-453.
He et al., "Comparative genomics of elastin: Sequence analysis of a highly repetitive protein," Matrix Biology, Sep. 2007, 26:524-540.
He et al., "Improving protein resistance of α-Al2O3 membranes by modification with POEGMA brushes," Applied Surface Science, Nov. 2011, 258(3):1038-1044.
Heagerty et al., Biometrics, "Time-dependent ROC curves for censored survival data and a diagnostic marker," Jun. 2000, 56(2):337-44.
Heal et al., "N-Myristoyl transferase-mediated protein labelling in vivo," Org. Biomol. Chem., Aug. 2008, 6(13):2308-2315.
Heal et al., "Site-specific N-terminal labelling of proteins in vitro and in vivo using N-myristoyl transferase and bioorthogonal ligation chemistry," Chem. Commun., Jan. 2008, 3, 480-482.
Heredia et al., "In Situ Preparation of Protein-'Smart' Polymer Conjugates with Retention of Bioactivity," J. Am. Chem. Soc. Jan. 2006, 127, 16955-16960.
Herrero-Vanrell et al., "Self-assembled particles of an elastin-like polymer as vehicles for controlled drug release," J Control Release, 2005, 102, 113-122.
Hershfield et al., "Induced and pre-existing anti-polyethylene glycol antibody in a trial of every 3-week dosing of pegloticase for refractory gout, including in organ transplant recipients," Arthritis Res. Ther. 16, Mar. 2014, R63.
Hidalgo, "Pancreatic Cancer," N Engl J Med, Apr. 2010, 362, 1605-1617.
Hingorani et al., "Phase lb Study of PEGylated Recombinant Human Hyaluronidase and Gemcitabine in Patients with Advanced Pancreatic Cancer," Clinical Cancer Research, Jun. 2016, 22, 2848-2854.
Ho et al., "Chemoenzymatic Labeling of Proteins for Imaging in Bacterial Cells," J. Am. Chem. Soc., Nov. 2016, 138(46):15098-15101.
Ho et al., "Internal radiation therapy for patients with primary or metastatic hepatic cancer: a review," Cancer, 1998, 83, 1894-1907.

(56) References Cited

OTHER PUBLICATIONS

Hober et al., "Protein A chromatography for antibody purification," Journal of Chromatography B 848, Mar. 2007, pp. 40-47.
Hochkoeppler, "Expanding the landscape of recombinant protein production in *Escherichia coli*," Biotechnol. Lett., Dec. 2013, 35, 1971-1981.
Hofmann et al., "A kinetic study on the enzymatic hydrolysis of fluoresceindiacetate and fluorescein-di-β-D-galactopyranoside," Analytical biochemistry, 1983, 131(1):180-186.
Holehouse et al., "CIDER: Classification of Intrinsically Disordered Ensemble Regions," Biophysical Journal, Feb. 2015, vol. 108, Issue 2, Supplement 1, p. 228a.
Holehouse et al., "Functional Implications of Intracellular Phase Transitions," Biochemistry, May 2018, 57(17):2415-2423.
Holm et al., "Transperineal $^{125}$iodine seed implantation in prostatic cancer guided by transrectal ultrasonography, " The Journal of urology, 2002, 167, 985-988.
Hopp et al., "The effects of affinity and valency of an albumin-binding domain (ABD) on the half-life of a single-chain diabody-ABD fusion protein," Protein Engineering Design and Selection, Sep. 2010, 23(11): p. 827-834.
Hortobágyi, "Anthracyclines in the Treatment of Cancer," Drugs, 1997, vol. 54, No. 4, pp. 1-7.
Howell et al., "The MIRD Perspective 1999," J Nucl Med, 1999, 40, 3S-10S.
Hruby et al., "New bioerodable thermoresponsive polymers for possible radiotherapeutic applications," Journal of Controlled Release, May 2007, 119, 25-33.
Hruby et al., "Thermoresponsive polymeric radionuclide delivery system—an injectable brachytherapy," Eur J Pharm Sci., Feb. 2011, 42, 484-488.
Hrycushko et al., "Direct intratumoral infusion of liposome encapsulated rhenium radionuclides for cancer therapy: effects of non-uniform intratumoral dose distribution," Med Phys, Mar. 2011, 38, 1339-1347.
Hu et al., "Design of tumor-homing and pH-responsive polypeptide-doxorubicin nanoparticles with enhanced anticancer efficacy and reduced side effects," Chemical Communications, Jun. 2015, 51, 11405-11408.
Hu et al., "Nanografting De Novo Proteins onto Gold Surfaces," Langmuir, 2005, vol. 21:9103-9109.
Huang et al., "Photodynamic Therapy Synergizes with Irinotecan to Overcome Compensatory Mechanisms and Improve Treatment Outcomes in Pancreatic Cancer," Cancer Research, Mar. 2016, 76, 1066-1077.
Huber et al., "Designer amphiphilic proteins as building blocks for the intracellular formation of organelle-like compartments," Nat Mater, Jan. 2015, 14(1):125-132.
Huotari et al., "Endosome maturation," EMBO J, Aug. 2011, 30 (17), 3481-3500.
Hwang et al., "Caprolactonic poloxamer analog: PEG-PCL-PEG," Biomacromolecules, 2005, 6, 885-890.
Hwang et al., "Gene therapy for primary and metastatic pancreatic cancer with intraperitoneal retroviral vector bearing the wild-type p53 gene," Surgery, 1998, 124, 143-151.
Ibrahim et al., "Phase I and pharmacokinetic study of ABI-007, a Cremophor-free, protein-stabilized, nanoparticle formulation of paclitaxel," Clin. Cancer Res., 2002, 8 (5), 1038-1044.
Ilangovan et al., "Structure of sortase, the transpeptidase that anchors proteins to the cell wall of *Staphylococcus aureus*," Proc. Natl. Acad. Sci. 98, 2001, 6056-6061.
Inostroza-Brito et al., "Co-assembly, spatiotemporal control and morphogenesis of a hybrid protein-peptide system," Nat. Chem., Nov. 2015, 7, 1-8.
Ishida et al., "Accelerated blood clearance (ABC) phenomenon upon repeated injection of PEGylated liposomes," International Journal of Pharmaceutics, May 2008, 354(1-2):56-62.
Ito et al., "Impaired negative feedback suppression of bile acid synthesis in mice lacking βKlotho," J Clin Invest, 2005, 115(8):2202-2208.
Ito et al., "In vivo antitumor effect of the mTOR inhibitor CCI-779 and gemcitabine in xenograft models of human pancreatic cancer," International Journal of Cancer, May 2006, 118, 2337-2343.
Jacob et al., "Human phagocytes employ the myeloperoxidase-hydrogen peroxide system to synthesize dityrosine, trityrosine, pulcherosine, and isodityrosine by a tyrosyl radical-dependent pathway," J. Biol. Chem., 1996, 271, 19950-19956.
Jain, "Barriers to Drug-Delivery in Solid Tumors," Sci Am, 1994, 271, 58-65.
Jakubowski et al., "Activators regenerated by electron transfer for atom-transfer radical polymerization of (meth)acrylates and related block copolymers," Angew. Chem. Int. Ed., Jun. 2006, 4482-4486.
Janes et al., "Chitosan nanoparticles as delivery systems for doxorubicin," J. Control Release, 2001, 73, 255-267.
Jenkins et al., In vivo monitoring of tumor relapse and metastasis using bioluminescent PC-3M-luc-C6 cells in murine models of human prostate cancer. Clinical & Experimental Metastasis, 2003, 20, 745-756.
Ji et al., "RGD-conjugated albumin nanoparticles as a novel delivery vehicle in pancreatic cancer therapy," Cancer Biology & Therapy, Feb. 2012, 13, 206-215.
Jia et al., "Preparation, physicochemical characterization and cytotoxicity in vitro of gemcitabine-loaded PEG-PDLLA nanovesicles," World J. Gastroenterol., Feb. 2010, 16(8):1008-1013.
Jiang et al., "Nanoparticle-mediated cellular response is size-dependent," Nat Nanotechnol, Nature Research, Mar. 2008, 3(3):145-50.
Jiang et al., "The internal structure of self-assembled peptide amphiphiles nanofibers," Soft Matter, Feb. 2007, 3, 454.
Jin et al., "Protein-resistant polyurethane prepared by surface-initiated atom transfer radical graft polymerization (ATRgP) of water-soluble polymers: effects of main chain and side chain lengths of grafts," Colloids and surfaces. B, Biointerfaces, Apr. 2009, 70 (1), 53-9.
Johansson et al., "Structure, Specificity, and Mode of Interaction for Bacterial Albumin-binding Modules," J. Biol. Chem. 2002, 277 (10), 8114-8120.
Johansson et al., "The GA module, a mobile albumin-binding bacterial domain, adopts a three-helix-bundle structure," FEBS Lett, 1995, 374(2): 257-261.
Johnson et al., "Fibroblast Growth Factor 21 Reduces the Severity of Cerulein-Induced Pancreatitis in Mice," Gastroenterology, Nov. 2009, 137(5):1795-1804.
Jokerst et al., "Nanoparticle PEGylation for imaging and therapy," Nanomedicine (Lond), Future Medicine, Jun. 2011, 6(4):715-28.
Jonsson et al., "Engineering of a femtomolar affinity binding protein to human serum albumin," Protein Engineering Design and Selection, Aug. 2008, 21(8): 515-527.
Junutula et al., "Site-specific conjugation of a cytotoxic drug to an antibody improves the therapeutic index," Nat Biotechnol, Aug. 2008, 26(8):925-932.
Jurney et al., "Unique size and shape-dependent uptake behaviors of non-spherical nanoparticles by endothelial cells due to a shearing flow," J Control Release, Jan. 2017, 245:170-176.
Kaighn et al., "Establishment and characterization of a human prostatic carcinoma cell line (PC-3)," Investigative urology, 1979, 17, 16-23.
Kaitin et al., "Pharmaceutical innovation in the 21st century: new drug approvals in the first decade, 2000-2009," Clin Pharmacol Ther, Feb. 2011, 89, 183-188.
Kamaly et al., "Targeted polymeric therapeutic nanoparticles: design, development and clinical translation," Chem Soc Rev, Royal Society of Chemistry, Apr. 2012, 41(7):2971-3010.
Kamisawa et al., "Pancreatic cancer," Lancet, Jul. 2016, 388, 73-85.
Kanoski et al., "The role of nausea in food intake and body weight suppression by peripheral GLP-1 receptor agonists, exendin-4 and liraglutide," Neuropharmacology 62, Apr. 2012, 1916-1927.
Kanyama et al., "Usefulness of Repeated Direct Intratumoral Gene Transfer Using Hemagglutinating Virus of Japan-Liposome Method for Cytosine Deaminase Suicide Gene Therapy," Cancer Research, 2001, 61, 14-18.

(56) References Cited

OTHER PUBLICATIONS

Karagoz et al., "Polymerization-Induced Self-Assembly (PISA)—control over the morphology of nanoparticles for drug delivery applications," Polym. Chem., Jan. 2014, 5(2):350-355.
Karamanolis et al., "Increased expression of VEGF and CD31 in postradiation rectal tissue: implications for radiation proctitis," Mediators Inflamm, May 2013, 515048.
Karperien, A. FracLac for Image J, version 2.5 <http://rsb.info.nih.gov/ij/plugins/fraclac/FLHelp/Introduction.htm> 1999-2012.
Kaspar et al., "Future directions for peptide therapeutics development," Drug Discovery Today, Sep. 2013, 18, 807-817.
Katakura, "Nuclear Data Sheets for A=125," Nuclear Data Sheets, Mar. 2011, 112, 495-705.
Kataoka et al., "Block copolymer micelles for drug delivery: Design, characterization and biological significance," Advanced Drug Delivery Reviews, 2001, 47:113-131.
Kato et al., "Acidic extracellular microenvironment and cancer," Cancer Cell Int, Sep. 2013, 13, 89, 8 pages.
Katti et al., "Amino acid repeat patterns in protein sequences: Their diversity and structural-functional implications," Protein Science, 2000, 9: 1203-1209.
Keefe et al., "Poly(zwitterionic) protein conjugates offer increased stability without sacrificing binding affinity or bioactivity," Nat Chem, Jan. 2012, 4(1):59-63.
Keller et al., "Empirical Statistical Model To Estimate the Accuracy of Peptide Identifications Made by MS/MS and Database Search," Anal. Chem. 2002, 74, 5383-5392.
Kelly et al., "How to study proteins by circular dichroism," Biochim. Byophys. Acta—Proteins Proteomics, 2005, 1751(2):119-39.
Kelly et al., "Shape-specific, monodisperse nano-molding of protein particles," J Am Chem Soc, ACS Publications, Apr. 2008, 130(16):5438-9.
Kesharwani et al., "Dendrimer as nanocarrier for drug delivery," Progress in Polymer Science, Feb. 2014, 39(2):268-307.
Keten et al., "Nanoconfinement controls stiffness, strength and mechanical toughness of β-sheet crystals in silk," Nat Mater, Mar. 2010, 9, 359-367.
Khandare et al., "Polymer-drug conjugates: Progress in polymeric drugs," Prog. Polym. Sci., 2005, vol. 31, pp. 359-397.
Khanna et al., "The dog as a cancer model," Nat. Biotechnol., Sep. 2006, 24, 1065-1066.
Kharitonenkov et al., "FGF-21 as a novel metabolic regulator," J Clin Invest, 2005, 115(6):1627-1635.
Kharitonenkov et al., "FGF21 Revolutions: Recent Advances Illuminating FGF21 Biology and Medicinal Properties," Trends Endocrinol Metab, Nov. 2015, 26(11):608-617.
Kharitonenkov et al., "Fibroblast growth factor 21 night watch: advances and uncertainties in the field," J Intern Med, Nov. 2016, 281(3):233-246.
Kharitonenkov et al., "Inventing new medicines: The FGF21 story," Mol Metab, Jun. 2014, 3(3):221-229.
Khazov et al., "Nuclear Data Sheets for A=131," Nuclear Data Sheets, 2006, 107, 2715-2930.
Khoo et al., "Activation of mitogen-activating protein kinase by glucose is not required for insulin secretion," Proc Natl Acad Sci USA, 1997, 94(11):5599-5604.
Khoo et al., "Regulation of Insulin Gene Transcription by ERK1 and ERK2 in Pancreatic β Cells," J Biol Chem, 2003, 278(35):32969-32977.
Kim et al., "Effects of Once-Weekly Dosing of a Long-Acting Release Formulation of Exenatide on Glucose Control and Body Weight in Subjects With Type 2 Diabetes," Diabetes Care, Jun. 2007, 30, 1487-93.
Kim et al., "Recombinant elastin-mimetic biomaterials: Emerging applications in medicine," Adv Drug Deliv Rev, Dec. 2010, 62, 1468-1478.
Kim et al., "Site-Specific PEGylated Exendin-4 Modified with a High Molecular Weight Trimeric PEG Reduces Steric Hindrance and Increases Type 2 Antidiabetic Therapeutic Effects," Bioconjugate Chem., Nov. 2012, 23, 2214-2220.
Kim et al., "Ultrasensitive Carbon nanotube-based biosensors using antibody-binding fragments," Analytical Biochemistry, Jul. 2008, 381, 193-198.
Knop et al., "Poly(ethylene glycol) in Drug Delivery: Pros and Cons as Well as Potential Alternatives," Angewandte Chemie International Edition, Aug. 2010, 49(36):6288-6308.
Knudsen, "Glucagon-like Peptide-1: The Basis of a New Class of Treatment for Type 2 Diabetes" J. Med. Chem, 2004, 47: 4128-4134.
Kobashigawa et al., "Attachment Of An NMR-Invisible Solubility Enhancement Tag Using A Sortase-Mediated Protein Ligation Method," J Biomol NMR. Mar. 2009, vol. 43, No. 3; pp. 145-150.
Kobayashi et al., "Summary of recombinant human serum albumin development," Biologicals, Mar. 2006, 34(1): 55-59.
Koehler et al., "Albumin affinity tags increase peptide half-life In vivo," Bioorganic & Medicinal Chemistry Letters, 2002, 12(20): 2883-2886.
Kontos et al., "Drug development: longer-lived proteins," Chemical Society Reviews, Feb. 2012, 41(7):2686-2695.
Koong et al., "Phase II study to assess the efficacy of conventionally fractionated radiotherapy followed by a stereotactic radiosurgery boost in patients with locally advanced pancreatic cancer," Int J Radiation Oncol Biol Phys, 2005, 63, 320-323.
Kothare et al., "Pharmacokinetics, pharmacodynamics, tolerability, and safety of exenatide in Japanese patients with type 2 diabetes mellitus," J. Clin. Pharmacol. 48, Jan. 2009, 1389-1399.
Kowalczyk et al., "Elastin-like Polypeptides as a Promising Family of Genetically-Engineered Protein Based Polymers," World Journal of Microbiology and Biotechnology, Springer, Apr. 2014, 30(8):2141-2152.
Kramer et al., "Quantitative Side-Chain Modifications of Methionine-Containing Elastin-Like Polypeptides as a Versatile Tool to Tune Their Properties," ACS Macro Lett., Nov. 2015, 4(11):1283-1286.
Kraulis et al., "The serum albumin-binding domain of streptococcal protein G is a three-helical bundle: a heteronuclear NMR study," FEBS letters, 1996, 378(2): p. 190-194.
Krause et al., "Structure and function of claudins," Biochmica et Biophysica Acta, Mar. 2008, 1778, 631-645.
Krempien et al., "Neoadjuvant chemoradiation in patients with pancreatic adenocarcinoma," HPB (Oxford), Feb. 2006, 8(1):22-28.
Kruger et al., "Analysis of the Substrate Specificity of the *Staphylococcus aureus* Sortase Transpeptidase SrtA†," Biochemistry, 2004, 43, 1541-1551.
Kulkarni et al., "Bioorthogonal Chemoenzymatic Functionalization of Calmodulin for Bioconjugation Applications," Bioconjug. Chem., Oct. 2015, 26(10):2153-2160.
Kulkarni et al., "Design of lipid nanoparticles for in vitro and in vivo delivery of plasmid DNA," Nanomedicine, May 2017, 13(4):1377-1387.
Kulkarni et al., "Selective functionalization of the protein N terminus with N-myristoyl transferase for bioconjugation in cell lysate," ChemBioChem, Oct. 2013, 14, 1958-1962.
Kumar et al., "N-Terminal Region of the Catalytic Domain of Human N-Myristoyltransferase 1 Acts as an Inhibitory Module," PLoS One, May 2015, 10(5):e0127661.
Kupelian et al., "Radical prostatectomy, external beam radiotherapy <72 Gy, external beam radiotherapy > or =72 Gy, permanent seed implantation, or combined seeds/external beam radiotherapy for stage T1-T2 prostate cancer," International journal of radiation oncology, biology, physics, 2004, 58, 25-33.
Kurosu et al., "Tissue-specific Expression of BKlotho and Fibroblast Growth Factor (FGF) Receptor Isoforms Determines Metabolic Activity of FGF19 and FGF21," J Biol Chem, Sep. 2007, 282(37):26687-26695.
Kyte et al., "A Simple Method for Displaying the Hydropathic Character of a Protein," J. Mol. Biol., 1982, 157:105-132.
Labelle et al., "Vascular endothelial cadherin promotes breast cancer progression via transforming growth factor β signaling," Cancer Res, Mar. 2008, 68, 1388-1397.
Lacroix et al., "Elucidating the folding problem of alpha-helices: local motifs, long-range electrostatics, ionic-strength dependence and prediction of NMR parameters," J Mol Biol, 1998, 284, 173-191.

(56) References Cited

OTHER PUBLICATIONS

Langer et al., "Designing materials for biology and medicine," Nature, 2004, 428, 487-92.
Laybutt et al., "Endoplasmic reticulum stress contributes to beta cell apoptosis in type 2 diabetes," Diabetologia, Apr. 2007, 50(4):752-763.
Le Droumaguet et al., "Recent advances in the design of bioconjugates from controlled/living radical polymerization," Polym. Chem. Jan. 2010, 1, 563-598.
Le Meins et al., "Hybrid polymer/lipid vesicles: State of the art and future perspectives," Mater. Today, Oct. 2013, 16, 397-402.
Leader et al., "Protein therapeutics: a summary and pharmacological classification," Nat. Rev. Drug Discov. 7, Jan. 2008, 21-39.
Lee et al., "Atomistic molecular dynamics simulations of peptide amphiphile self-assembly into cylindrical nanofibers," J. Am. Chem. Soc., Feb. 2011, 133, 3677-3683.
Lee et al., "Immunohistochemical analysis of claudin expression in pancreatic cystic tumors," Oncology Reports, Apr. 2011, 25(4): 971-978.
Lee et al., "In vivo bioluminescent imaging of irradiated orthotopic pancreatic cancer xenografts in nonobese diabetic-severe combined immunodeficient mice: a novel method for targeting and assaying efficacy of ionizing radiation," Transl. Oncol., Jun. 2010, 3, 153-159.
Lee et al., "Mechanical properties of cross-linked syntheti elastomeric polypentapeptides," Macromolecules, 2001, 34, 5968-5974.
Lee et al., "Nanoparticle-Delivered Chemotherapy: Old Drugs in New Packages." Oncology (Williston Park, NY) 31.3 (Mar. 2017): 198-208.
Lee et al., "Phase transition and elasticity of protein-based hydrogels," J. Biomater. Sci. Polymer Edn, 2001, 12, 229-242.
Lee et al., "Polymersomes for drug delivery: design, formation and characterization," J Control Release, Elsevier, Jul. 2012, 161(2):473-83.
Lee et al., "Structures of β-klotho reveal a 'zip code'-like mechanism for endocrine FGF signaling," Nature, Jan. 2018, 553:501-505.
Lee et al., "Theranostic nanoparticles with controlled release of gemcitabine for targeted therapy and MRI of pancreatic cancer," ACS Nano, Mar. 2013, 7(3):2078-2089.
Leibowitz et al., "Glucose-Regulated Proinsulin Gene Expression Is Required for Adequate Insulin Production during Chronic Glucose Exposure," Endocrinology, 2002, 143(9):3214-3220.
Lele et al., "Synthesis of uniform protein-polymer conjugates," Biomacromolecules 6, 2005, 3380-3387.
Lennen et al., "Membrane Stresses Induced by Overproduction of Free Fatty Acids in *Escherichia coli*," Appl Environ Microb., Nov. 2011, 77(22):8114-28.
Leung et al., "Bio-Click Chemistry: Enzymatic Functionalization of PEGylated Capsules for Targeting Applications**," Angew. Chem. Int. Ed. Jul. 2012, 51, 7132-7136.
LeVine et al., "Thioflavine T interaction with synthetic Alzheimer's disease beta-amyloid peptides: detection of amyloid aggregation in solution," Protein Sci., 1993, 2, 404-10.
Levy et al., "Novel Exenatide Analogs with Peptidic Albumin Binding Domains: Potent Anti-Diabetic Agents with Extended Duration of Action," PLoS ONE, Feb. 2014, 9(2): e87704, 9 pages.
Lewis et al., "Use of digitized video microscopy with a fluorogenic enzyme substrate to demonstrate cell-and compartment-specific gene expression in Salmonella enteritidis and *Bacillus subtilis*," Molecular microbiology, 1994, 13:655-662.
Li et al., "Elastin is an essential determinant of arterial morphogenesis," Nature, 1998, 393, 276-280.
Li et al., "FGF21 Is Not a Major Mediator for Bone Homeostasis or Metabolic Actions of PPARα and PPARγ Agonists," J Bone Miner Res, Apr. 2017, 32(4):834-845.
Li et al., "Molecular description of the LCST behavior of an elastin-like polypeptide," Biomacromolecules, Aug. 2014, 15, 3522-3530.
Li et al., "Nanoparticles Evading The Reticuloendothelial System: Role of The Supported Bilayer," Biochim. Biophys. Acta, Oct. 2009, 1788 (10), 2259-2266.
Li et al., "Pancreatic cancer," Lancet, 2004, 363, 1049-1057.
Li et al., "Phase transitions in the assembly of multivalent signalling proteins," Nature, Nature Research, Mar. 2012, 483(7389):336-340.
Li et al., "Prediction of solvent-induced morphological changes of polyelectrolyte diblock copolymer micelles," Soft Matter, Nov. 2015, 11(42): 8236-45.
Li et al., "Protein adsorption on oligo(ethylene glycol)-terminated alkanethiolate self-assembled monolayers: The molecular basis for nonfouling behavior," The journal of physical chemistry. B, 2005, 109 (7), 2934-41.
Li et al., "Temperature-Triggered Phase Separation of a Hydrophilic Resilin-Like Polypeptide," Macramol. Rapid Commun., Jan. 2015, 36(1):90-95.
Li et al., "Tunable Assembly of Protein-Microdomains in Living Vertebrate Embryos," Advanced Biosystems, Oct. 2018, 2(10):1800112.
Liao et al., "Removal of N-terminal methionine from recombinant proteins by engineered *E. coli* methionine aminopeptidase," Prot. Sci. 13, 2004, 1802-1810.
Liechty et al., "Polymers for Drug Delivery Systems," Annual review of chemical and biomolecular engineering, Aug. 2010, 1:149-173.
Lillie et al., "The viscoelastic basis for the tensile strength of elastin," Int J Biol Macromol, 2002, 30, 119-127.
Lim et al., "Improved Non-Chromatographic Purification of a Recombinant Protein by Cationic Elastin-like Polypeptides" Biomacromolecules, May 2007, 8(5): 1417-1424.
Lim et al., "In situ cross-linking of elastin-like polypeptide block copolymers for tissue repair," Biomacromolecules, Feb. 2008, 9, 222-230.
Lim et al., "In vivo post-translational modifications of recombinant mussel adhesive protein in insect cells," Biotechnol. Prog., September-Oct. 2011, 27(5):1390-1396.
Lin et al., "Adiponectin Mediates the Metabolic Effects of FGF21 on Glucose Homeostasis and Insulin Sensitivity in Mice," Cell Metab, May 2013, 17(5):779-789.
Lin et al., "Formation and Maturation of Phase-Separated Liquid Droplets by RNA-Binding Proteins," Mol Cell, Oct. 2015, 60(2):208-219.
Lin et al., "Functional expression of a biologically active fragment of soluble gp130 as an ELP-fusion protein in transgenic plants: purification via inverse transition cycling," Biochem J, Sep. 2006, 398(3):577-583.
Lin et al., "Intrinsically disordered sequences enable modulation of protein phase separation through distributed tyrosine motifs," J Biol Chem, Nov. 2017, 292(46):19110-19120.
Lin et al., "Phase Separation and Single-Chain Compactness of Charged Disordered Proteins Are Strongly Correlated," Biophys J, May 2017, 112(10):2043-2046.
Lin et al., "Sequence-Specific Polyampholyte Phase Separation in Membraneless Organelles," Phys Rev Lett, Oct. 2016, 117(17):178101.
Lin et al., "Statistical properties of the traditional algorithm-based designs for phase I cancer clinical trials," Biostatistics, 2001, 2(2):203-215.
Lin et al., "Utility of immunohistochemistry in the pancreatobiliary tract," Arch Pathol Lab Med, Jan. 2015, 139, 24-38.
Linder et al., "Lipid Modifications of G Protein Subunits," J. Biol. Chem., 1991, 266(7):4654-4659.
Ling et al., "Protein thioester synthesis enabled by sortase," J. Am Chem Soc, Jul. 2012, 134(26):10749-10752.
Liong et al., "Multifunctional inorganic nanoparticles for imaging, targeting, and drug delivery," ACS Nano, ACS Publications, May 2008, 2(5):889-96.
Litiere et al., "RECIST—learning from the past to build the future," Nat Rev Clin Oncol, Mar. 2017, 14, 187-192.
Liu et al., "Brachytherapy using injectable seeds that are self-assembled from genetically encoded polypeptides in situ," Cancer Res, Nov. 2012, 72, 5956-5965.
Liu et al., "Hydrophobic modifications of cationic polymers for gene delivery," Prog. In Polym. Sci., Sep. 2010, 35, 1144-1162.

(56) References Cited

OTHER PUBLICATIONS

Liu et al., "In Situ Formation of Protein-Polymer Conjugates through Reversible Addition Fragmentation Chain Transfer Polymerization**," Angew. Chem. Int. Ed. Apr. 2007, 46, 3099-3103.
Liu et al., "Injectable intratumoral depot of thermally responsive polypeptide-radionuclide conjugates delays tumor progression in a mouse model," J. Control Release, May 2010, 144(1):2-9.
Liu et al., "Integrin $\alpha_v\beta_3$-Targeted Cancer Therapy," Drug Dev Res, Wiley, Sep. 2008, 69(6):329-339.
Liu et al., "Tracking the in vivo fate of recombinant polypeptides by isotopic labeling," Journal of Controlled Release, Sep. 2006, 114, 184-192.
Liu et al., "Tumor accumulation, degradation and pharmacokinetics of elastin-like polypeptides in nude mice," Journal of Controlled Release, Nov. 2006, 116, 170-178.
Livingstone, "Theoretical property predictions. Curr Top Med Chem FIELD Full Journal Title: Current topics in medicinal chemistry," Curr. Top. Med. Chem. 2003, 3, 1171-1192.
Loh et al., "Utilising inorganic nanocarriers for gene delivery," Biomater Sci, Jan. 2016, 4(1):70-86.
LoPresti et al., "Polymersomes: nature inspired nanometer sized compartments," Journal of Materials Chemistry, RSC Publishing, Jun. 2009, 19(22):3576-3590.
Lovshin et al., "Incretin-based therapies for type 2 diabetes mellitus," Nat. Rev. Endocrinol. 5, Jun. 2009, 262-269.
Ludden, "Nonlinear pharmacokinetics: clinical Implications," Clin. Pharmacokinet., 1991, 20 (6), 429-446.
Luginbuhl et al., "One-week glucose control via zero-order release kinetics from an injectable depot of glucagon-like peptide-1 fused to a thermosensitive biopolymer," Nat. Biomed. Eng. 1, Jun. 2017, Article No. 0078.
Luginbuhl et al., "Recombinant Synthesis of Hybrid Lipid-Peptide Polymer Fusions that Self-Assemble and Encapsulate Hydrophobic Drugs," Angew Chem Int Ed Engl., Nov. 2017, 56(45):13979-13984.
Lukyanov et al., "Micelles From Lipid Derivatives of Water-Soluble Polymers as Delivery Systems for Poorly Soluble Drugs," Adv. Drug Deliver. Rev., 2004, 56(9):1273-1289.
Lukyanov et al., "Tumor-targeted liposomes: doxorubicin-loaded long-circulating liposomes modified with anti-cancer antibody," J Control Release, 2004, 100(1):135-44.
Lund et al., "Phase II study of gemcitabine (2',2'-difluorodeoxycytidine) in previously treated ovarian cancer patients," J. Natl. Cancer. Inst. 1994, 86(20):1530-1533.
Luo et al., "Noncovalent Modulation of the Inverse Temperature Transition and Self-Assembly of Elastin-b-Collagen-like Peptide Bioconjugates," J Am Chem Soc, Dec. 2015, 137, 15362-15365.
Lutz et al., "About the Phase Transitions in Aqueous Solutions of Thermoresponsive Copolymers and Hydrogels Based on 2-(2-methoxyethoxy)ethyl Methacrylate and Oligo(ethylene glycol) Methacrylate," Macromolecules, Mar. 2007, 40, 2503-2508.
Lutz et al., "Preparation of Ideal PEG Analogues with a Tunable Thermosensitivity by Controlled Radical Copolymerization of 2-(2-Methoxyethoxy)ethyl Methacrylate and Oligo(ethylene glycol) Methacrylate," Macromolecules, Jan. 2006, 39, 893-896.
Lyons et al., "Comparisons of Recombinant Resilin-like Proteins: Repetitive Domains Are Sufficient to Confer Resilin-like Properties," Biomacromolecules, ACS Publications, Oct. 2009, 10(11):3009-3014.
Lyons et al., "Design and facile production of recombinant resilin-like polypeptides: Gene construction and a rapid protein purification method," Protein Engineering Design & Selection, Oxford university Press, Jan. 2007, 20(1):25-32.
Ma et al., "Non-fouling" oligo(ethylene glycol)-functionalized polymer brushes synthesized by surface-initiated atom transfer radical polymerization, Advanced Materials 2004, 16 (4), 338.
Ma et al., "Protein-resistant polymer coatings on silicon oxide by surface-initiated atom transfer radical polymerization," Langmuir: the ACS journal of surfaces and colloids, Mar. 2006, 22 (8), 3751-6.
Ma et al., "Surface-Initiated Atom Transfer Radical Polymerization of Oligo(ethylene glycol) Methyl Methacrylate from a Mixed Self-Assembled Monolayer on Gold," Advanced Functional Materials, Mar. 2006, 16 (5), 640-648.
MacEwan et al., "Applications of elastin-like polypeptides in drug delivery," Journal of Controlled Release, Sep. 2014, 190: p. 314-330.
MacEwan et al., "Controlled apoptosis by a thermally toggled nanoscale amplifier of cellular uptake," Nano Letters, Apr. 2014, 14, 2058-2064.
MacEwan et al., "Digital switching of local arginine density in a genetically encoded self-assembled polypeptide nanoparticle controls cellular uptake," Nano Lett., Jun. 2012, 12, 3322-3328.
MacEwan et al., "Elastin-like polypeptides: Biomedical applications of tunable biopolymers," Biopolymers, Jan. 2010, 94, 60-77.
MacEwan et al., "Non-chromatographic Purification of Recombinant Elastin-like Polypeptides and their Fusions with Peptides and Proteins from *Escherichia coli*," Jun. 2014, 88, p. e51583.
MacEwan et al., "Phase Behavior and Self-Assembly of Perfectly Sequence-Defined and Monodisperse Multiblock Copolypeptides," Biomacromolecules, Jan. 2017, 18(2):599-609.
Mack et al., "Antiobesity action of peripheral exenatide (exendin-4) in rodents: effects on food intake, body weight, metabolic status and side-effect measures," Int. J. Obes. 30, Sep. 2006, 1332-1340.
MacKay et al., "Self-assembling chimeric polypeptide-doxorubicin conjugate nanoparticles the abolish tumors after single injection," Nat Mater, Dec. 2009, 8(12):993-999.
Maeda et al., "Tumor vascular permeability and the EPR effect in macromolecular therapeutics: a review," J. Control. Release, Mar. 2000, 65(1-2)271-284.
Maeda et al., "Tumoritropic and lymphotropic principles of macromolecular drugs," Critical reviews in therapeutic drug carrier systems, 1989, 6(3):193-210.
Maeda, "The enhanced permeability and retention (EPR) effect in tumor vasculature: the key role of tumor-selective macromolecular drug targeting," Advances in Enzyme Regulation, 2001, 41(1):189-207.
Magnusson et al., "In Situ Growth of Side-Chain PEG Polymers from Functionalized Human Growth Hormone-A New Technique for Preparation of Enhanced Protein-Polymer Conjugates," Bioconjugate Chem. 21, Mar. 2010, 671-678.
Magnusson et al., "Ion-Sensitive "Isothermal" Responsive Polymers Prepared in Water," Journal of the American Chemical Society, Aug. 2008, 130, 10852-10853.
Maitra et al., "Pancreatic Cancer," Annu Rev Pathol Mech Dis, Feb. 2008, 3, 157-188.
Malam et al., "Liposomes and nanoparticles: nanosized vehicles for drug delivery in cancer," Trends Pharmacol Sci, Cell Press, Nov. 2009, 30(11):592-9.
Malik et al., "Recent advances in protein and peptide drug delivery systems," Curr. Drug Deliv. 2, Apr. 2007, 141-151.
Manders et al., "Dynamics of three-dimensional replication patterns during the S-phase, analysed by double labelling of DNA and confocal microscopy," Journal of cell science, 1992, 103(Pt 3):857-862.
Mann et al., "Proteomic analysis of post-translational modifications," Nat. Biotechnol., 2003, 21, 255-61.
Manzoor et al., "Overcoming limitations in nanoparticle drug delivery: triggered, intravascular release to improve drug penetration into tumors," Cancer Res, Nov. 2012, 72, 5566-5575.
Mao et al., "DNA repair by nonhomologous end joining and homologous recombination during cell cycle in human cells," Cell cycle, Sep. 2008, 7, 2902-2906.
Mao et al., "Net charge per residue modulates conformational ensembles of intrinsically disordered proteins," Proc Natl Acad Sci U S A, 2010, 107(18):8183-8188.
Mao et al., "Sortase-mediated protein ligation: a new method for protein engineering," J. Am. Chem. Soc., 2004, 126(9):2670-2671.
Maraffini et al., "Sortases and the art of anchoring proteins to the envelopes of Gram-positive bacteria," Microbiol Mol Biol Rev, Mar. 2006, 70(1):192-221.

(56) References Cited

OTHER PUBLICATIONS

Mariam et al., "Albumin corona on nanoparticles—a strategic approach in drug delivery," Drug Deliv., Oct. 2016, 23 (8), 2668-2676.
Marr et al., "Effect of Temperature on the Composition of Fatty Acids in *Escherichia Coli*," J Bacteriol., 1962, 84(6):1260-7.
Marten et al., "A randomized multicentre phase II trial comparing adjuvant therapy in patients with interferon alpha-2b and 5-FU alone or in combination with either external radiation treatment and cisplatin (CapRI) or radiation alone regarding event-free survival—CapRI-2," BMC Cancer, Feb. 2009, 9, 1-8.
Maskarinec et al., "Protein engineering approaches to biomaterials design," Curr. Opin. Biotechnol., 2005, 16, 422-426.
Masood, "Polymeric nanoparticles for targeted drug delivery system for cancer therapy," Mater Sci Eng C Mater Biol Appl, Mar. 2016, 60:569-578.
Massey et al., "Self-Assembly of a Novel Organometallic-Inorganic Block Copolymer in Solution and the Solid State: Nonintrusive Observation of Novel Wormlike Poly(ferrocenyldimethylsilane)-b-Poly(dimethylsiloxane) Micelles," J. Am. Chem. Soc. 1998, 120(37):9533-9540.
Mastria et al., "Doxorubicin-conjugated polypeptide nanoparticles inhibit metastasis in two murine models of carcinoma," J Control Release, Jun. 2015, 208:52-8.
Mastria et al., "Nanoparticle formulation improves doxorubicin efficacy by enhancing host antitumor immunity," J Control Release, Jan. 2018, 269:364-373.
Matsumura et al., "A new concept for macromolecular therapeutics in cancer chemotherapy: mechanism of tumoritropic accumulation of proteins and the antitumor agent smancs," Cancer Res. 1986, 46, 6387-6392.
Matsumura, "Cancer stromal targeting (CAST) therapy," Advanced Drug Delivery Reviews, Jun. 2012, 64, 710-719.
Matthews et al., "Pharmacodynamics, Pharmacokinetics, Safety, and Tolerability of Albiglutide, a Long-Acting Glucagon-Like Peptide-1 Mimetic, in Patients with Type 2 Diabetes," J Clin Endocrinol Metab, Dec. 2008, 93(12):4810-4817.
Matyjaszewski et al., "Atom transfer radical polymerization," Chem. Rev. 101, Sep. 2001, 2921-2990.
Matyjaszewski et al., "Macromolecular engineering by atom transfer radical polymerization," J. Am. Chem. Soc. 136, 2014, 6513-6533.
Maurer-Stroh et al., "N-terminal N-myristoylation of proteins: prediction of substrate proteins from amino acid sequence" J Mol Biol., 2002, 317(4):541-557.
Maurer-Stroh et al., "N-terminal N-myristoylation of proteins: Refinement of the sequence motif and its taxon-specific differences," J Mol Biol., 2002, 317(4):523-540.
Mayo et al., "Cell Adhesion Promoting Peptide GVKGDKGNPGWPGAP from the Collagen Type IV Triple Helix: Cis/Trans Proline-Induced Multiple 1H Nmr Conformations and Evidence for a KG/PG Multiple Turn Repeat Motif in the All-Trans proline State," Biochemistry, 1991, 30: 8251-8267.
McConkey et al., "Molecular Characterization of Pancreatic Cancer Cell Lines," Pancreatic Cancer, Jan. 2010, 457-469.
McDaniel et al., "A unified model for de novo design of elastin-like polypeptides with tunable inverse transition temperatures," Biomacromolecules, Aug. 2013, 14(8):2866-2872.
McDaniel et al., "Actively targeting solid tumours with thermoresponsive drug delivery systems that respond to mild hyperthermia," Int J Hyperthermia, Aug. 2013, 29, 501-510.
McDaniel et al., "Doxorubicin-conjugated chimeric polypeptide nanoparticles that respond to mild hyperthermia," Control. Release, May 2012, 159 (3), 362-367.
McDaniel et al., "Drug delivery to solid tumors by elastin-like polypeptides," Adc. Drug Deliver. Rev., Dec. 2010, 62(15):1456-1467.
McDaniel et al., "Noncanonical Self-Assembly of Highly Asymmetric Genetically Encoded Polypeptide Amphiphiles into Cylindrical Micelles," Nano Lett., Sep. 2014, 14(11):6590-6598.
McDaniel et al., "Rational design of "heat seeking" drug loaded polypeptide nanoparticles that thermally target solid tumors," Nano Letters, Apr. 2014, 14, 2890-2895.
McDaniel et al., "Recursive Directional Ligation by Plasmid Reconstruction Allows Rapid and Seamless Cloning of Oligomeric Genes," Biomacromolecules, Feb. 2010, 11(4):944-952.
McDaniel et al., "Self-assembly of thermally responsive nanoparticles of a genetically encoded peptide polymer by drug conjugation," Chem. Int. Ed. Feb. 2013, 52, 1683-1687.
McDaniel, "Assembly of Highly Asymmetric Genetically-Encoded Amphiphiles for Thermally Targeted Delivery of Therapeutics," Dissertation, 2013, 295 pages, Published Mar. 1, 2014.
McHale et al., "Synthesis and in vitro evaluation of enzymatically cross-linked elastin-like polypeptide gels for cartilaginous tissue repair," Tissue Eng., 2005, 11, 1768-1779.
McIlhinney et al., "Characterization of a polyhistidine-tagged form of human myristoyl-CoA: protein N-myristoyltransferase produced in *Escherichia Coli*," European Journal of Biochemistry, 1994, 222(1):137-146.
McKenzie et al., "Multivalent Binding of a Ligand-Coated Particle: Role of Shape, Size, and Ligand Heterogeneity," Biophys J, Apr. 2018, 114(8):1830-1846.
Meier et al., "Determination of Optimal Sample Size for Quantification of $\beta$-Cell Area, Amyloid Area and $\beta$-Cell Apoptosis in Isolated Islets," J Histochem Cytochem, Aug. 2015, 63(8):663-673.
Mejuch et al., "Synthesis of lipidated proteins," Bioconjug. Chem. 27, Jul. 2016, 1771-1783.
Meng et al., "Stimuli-responsive polymersomes for programmed drug delivery," Biomacromolecules, ACS Publications, Feb. 2009, 10(2):197-209.
Merkel et al., "Using mechanobiological mimicry of red blood cells to extend circulation times of hydrogel microparticles," Proc Natl Acad Sci U S A, The National Academy of Sciences of the USA, Jan. 2011, 108(2):586-91.
Mero et al., "Transglutaminase-mediated PEGylation of proteins: direct identification of the sites protein medification by mass spectrometry using a novel monodisperse PEG," Bioconjug Chem, Feb. 2009, 20(2):384-389.
Merriam Webster Dictionary, "Plurality," <https://www.merriam-webster.com/dictionary/plurality> webpage accessed Jun. 25, 2020.
Merrick et al., "Seed fixity in the prostate/periprostatic region following brachytherapy," International journal of radiation oncology, biology, physics, 2000, 46, 215-220.
Meyer et al., "Drug targeting using thermally responsive polymers and local hyperthermia," Journal of Controlled Release, 2001, 74, 213-224.
Meyer et al., "Genetically Encoded Synthesis of Protein-Based Polymers with Precisely Specified Molecular Weight and Sequence by Recursive Directional Ligation: Examples from the Elastin-like Polypeptide System," Biomacromolecules, 2002, 3:357-367.
Meyer et al., "Purification of recombinant proteins by fusion with thermally-responsive polypeptide," Nat. Biotechnol., 1999, 17(11):1112-1115.
Meyer et al., "Quantification of the effects of chain length and concentration on the thermal behavior of elastin-like polypeptides," Biomacromolecules, 2004, 5(3):846-51.
Meyer et al., "Targeting a Genetically Engineered Elastin-Like Polypeptide to Solid Tumors by Local Hyperthermia," Cancer Res., 2001, 61(4):1548-1554.
Miao et al., "Sequence and domain arrangements influence mechanical properties of elastin-like polymeric elastomers," Biopolymers, Jun. 2013, 99, 392-407.
Miao et al., "Structural determinants of cross-linking and hydrophobic domains for self-assembly of elastin-like polypeptides," Biochemistry, 2005, 44, 14367-14375.
Michl et al., "Current concepts and novel targets in advanced pancreatic cancer," Gut, Jan. 2013, 62, 317-326.
Micsonai et al. "Accurate secondary structure prediction and fold recognition for circular dichroism spectroscopy," Proc Natl Acad Sci U S A, Jun. 2015, 112, E3095-3103.
Milenic et al., "Antibody-targeted radiation cancer therapy," Nature Reviews Drug Discovery, 2004, 3, 488-498.

(56) References Cited

OTHER PUBLICATIONS

Miller et al., "Solubilized, Spaced Polyalanines: A Context-Free System for Determining Amino Acid α-Helix Propensities," Journal of the American Chemical Society, 2002, 124, 945-962.
Mitragotri et al., "Physical approaches to biomaterial design," J. Nat Mater, Nature Publishing Group, Jan. 2009, 8(1):15-23.
Miyata et al., "Polymeric micelles for nano-scale drug delivery," Reaction & Functional Polymers, Mar. 2011, 71, 227-234.
Mjelle et al., "Cell cycle regulation of human DNA repair and chromatin remodeling genes," DNA Repair, Jun. 2015, 30, 53-67.
Modery et al., "Heteromultivalent liposomal nanoconstructs for enhanced targeting and shear-stable binding to active platelets for site-selective vascular drug delivery," Biomaterials, Elsevier, Dec. 2011, 32(35):9504-9514.
Molliex et al., "Phase separation by low complexity domains promotes stress granule assembly and drives pathological fibrillization," Cell, Sep. 2015, 163(1):123-133.
Moosmann et al., "Alpha complementation of LacZ in mammalian cells," Nucleic Acids Res, 1996, 24(6):1171-1172.
Morgan et al., "The combination of epidermal growth factor receptor inhibitors with gemcitabine and radiation in pancreatic cancer," Clin Cancer Res, Aug. 2008, 14, 5142-5149.
Mosbach et al., "Formation of proinsulin by immobilized *Bacillus subtilis*," Nature, 1983, 302, 543-545.
Mozhdehi et al., "Genetically Encoded Cholesterol-Modified Polypeptides," Journal of the American Chemical Society, Jan. 2019, 141(2):945-951.
Mozhdehi et al., "Genetically encoded lipid-polypeptide hybrid biomaterials that exhibit temperature-triggered hierarchical self-assembly," Nature chemistry, May 2018, 10(5):496-505.
Mu et al., "FGF21 Analogs of Sustained Action Enabled by Orthogonal Biosynthesis Demonstrate Enhanced Antidiabetic Pharmacology in Rodents," Diabetes, Feb. 2012, 61(2):505-512.
Muiznieks et al., "Modulated growth, stability and interactions of liquid-like coacervate assemblies of elastin," Matrix Biology 36, Jun. 2014, pp. 39-50.
Muiznieks et al., "Proline periodicity modulates the self-assembly properties of elastin-like polypeptides," J Biol Chem, The American Society for Biochemistry and Molecular Biology, Inc, Dec. 2010, 285(51):39779-39789.
Muiznieks et al., "Structural changes and facilitated association of tropoelastin," Archives of Biochemistry and Biophysics, 2003, 410, 317-323.
Muñoz et al., "Elucidating the folding problem of helical peptides using empirical parameters," Nature Structural Biology, 1994, 1, 399-409.
Muñoz et al., "Elucidating the Folding Problem of Helical Peptides using Empirical Parameters. II†. Helix Macrodipole Effects and Rational Modification of the Helical Content of Natural Peptides," Journal of Molecular Biology, 1995, 245, 275-296.
Muñoz et al., "Elucidating the folding problem of helical peptides using empirical parameters. III. Temperature and pH dependence," J Mol Biol, 1995, 245, 297-308.
Muralidharan et al., "Protein Ligation: an Enabling Technology for the Biophysical Analysis of Proteins," Nature Methods, Jun. 2006, vol. 3, No. 6, pp. 429-438.
Muro, "Challenges in design and characterization of ligand-targeted drug delivery systems," J Control Release, Elsevier, Dec. 2012, 164(2):125-37.
Murphy et al., "A dosimetric model of duodenal toxicity after stereotactic body radiotherapy for pancreatic cancer," Int J Radiation Oncology Biol Phys, Dec. 2010, 78, 1420-1426.
Na et al., "Thermoresponsive pore structure of biopolymer microspheres for a smart drug carrier," Langmuir, Jun. 2010, 26, 11165-11169.
Nagarsekar et al., "Genetically Engineered Polymers for Drug Delivery," Journal of Drug Targeting, 1999, 7(1):11-32.
Nahire et al., "Multifunctional Polymersomes for Cytosolic Delivery of Gemcitabine and Doxorubicin to Cancer Cells," Biomaterials, Aug. 2014, 35(24):6482-6497.

Nairn et al., "A Synthetic Resilin Is Largely Unstructured," Biophysical Journal, Oct. 2008, vol. 95 3358-3365.
Nakaoka et al., "Prolongation of the serum half-life period of superoxide dismutase by poly(ethylene glycol) modification," Journal of Controlled Release, 1997, 46(3):253-261.
Nanoprecision Medical, "Pipeline, Type II Diabetes," <http://www.nanoprecisionmedical.com/pipeline/diabetes> webpage available as early as Aug. 2018.
Napier et al., "Nanoparticle drug delivery platform," Journal of Macromolecular Science, Part C: Polymer Reviews, Taylor & Francis Group, LLC, Aug. 2007, 47(3):321-327.
National Institute of Mental Health, "Methods and Welfare Considerations in Behavioral Research with Animals: Report of a National Institutes of Health Workshop," NIH Publication No. 02-54083, Washington, DC: U.S. Government Printing Office. (Mar. 2002).
Nauck "Glucagon-like Peptide 1 (GLP-1) in the Treatment of Diabetes," Horm Metab Res, 2004, 36(11/12):852-858 (in English).
Nayeem et al., "Engineering enzymes for improved catalytic efficiency: a computational study of site mutagenesis in epothilone-B hydroxylase," Protein Eng Des Sel, Oxford Academy, Apr. 2009, 22(4):257-266.
Neidigh et al., "Exendin-4 and glucagon-like-peptide-q: NMR structural comparisons in the solution and micelle-associated states," Biochemistry 40, 2001, 13188-13200.
Nettles et al., "Applications of elastin-like polypeptides in tissue engineering," Adv Drug Deliv Rev, Dec. 2010, 62, 1479-1485.
Nettles et al., "In situ crosslinking elastin-like polypeptide gels for application to articular cartilage repair in a goat osteochondral defect model," Tissue Eng Part A, Jul. 2008, 14, 1133-1140.
Newcomb et al., "Advances in cryogenic transmission electron microscopy for the characterization of dynamic self-assembling nanostructures," Current Opinion in Colloid and Interface Science, Dec. 2012, 17, 350-359.
Newton et al., "Commissioning a small-field biological irradiator using point, 2D, and 3D dosimetry techniques," Medical Physics, Dec. 2011, 38, 6754-6762.
Ni et al., "Engineering of inorganic nanoparticles as magnetic resonance imaging contrast agents," Chem Soc Rev, Nov. 2017, 46(23):7438-7468.
Nichols et al., "Claudin 4 protein expression in primary and metastatic pancreatic cancer," Am J Clin Pathol, 2004, 121, 226-230.
Nicolas et al., "Fluorescently tagged polymer bioconjugates from protein derived macroinitiators," Chem. Commun. Jan. 2007, 45, 4697-4699.
Nie, "Understanding and overcoming major barriers in cancer nanomedicine," Nanomedicine (Lond) Jun. 2010, 5 (4), 523-528.
Nielsen, "Incretin mimetics and DPP-IV inhibitors for the treatment of type 2 diabetes," Drug Discov. Today 10, 2005, 703-710.
Nies et al., "Fibroblast Growth Factor Signaling in Metabolic Regulation," Front Endocrinol, Jan. 2016, 6(193) (in English).
Nilvebrant et al., "The albumin-binding domain as a scaffold for protein engineering," Computational and Structural Biotechnology Journal, Mar. 2013, 6: e201303009, 8 pages.
Niu et al., "The role of adhesion molecules, αvβ3, αvβ5 and their ligands in the tumor cell and endothelial cell adhesion," Eur J Cancer Prev, Wolters Kluwer, Dec. 2007, 16(6):517-27.
Nott et al., "Phase transition of a disordered nuage protein generates environmentally responsive membraneless organelles," Mol Cell, Mar. 2015, 57(5):936-947.
Nucci et al., "The therapeutic value of poly(ethylene glycol)-modified proteins," Adv. Drug Deliv. Rev., 1991, 6(2):133-151.
Nuhn et al., "Secondary structure formation and LCST behavior of short elastin-like peptides," Biomacromolecules, Sep. 2008, 9, 2755-2763.
O'Day et al., "Therapeutic Protein-polymer Conjugates: Advancing beyond PEGylation," J. Am. Chem. Soc., Sep. 2014, vol. 136, pp. 14323-14332.
Ogawara et al., "Pre-coating with serum albumin reduces receptor-mediated hepatic disposition of polystyrene nanosphere: implications for rational design of nanoparticles," Journal of Controlled Release, 2004, 100(3): 451-455.

(56) References Cited

OTHER PUBLICATIONS

Olafsen et al., "Covalent disulfide-linked anti-CEA diabody allows site-specific conjugation and radiolabeling for tumor targeting applications," Protein Engineering, Design & Selection, 2004, 17(1):21-27.
Ortega et al., "Hydrodynamic properties of rodlike and dislike particles in dilute solution," The Journal of Chemical Physics, 2003, 119(18):9914-9919.
Ortony et al., "Internal dynamics of a supramolecular nanofibre," Nat. Mater., Aug. 2014, 13, 1-5.
Ozer et al., "Site-Specific and Stoichiometric Stealth Polymer Conjugates of Therapeutic Peptides and Proteins," Bioconjug Chem, Mar. 2017, 28(3):713-723.
Pace et al., "How to measure and predict the molar absorption coefficient of a protein" Protein Science 1995, 4: 2411-2423.
Pagani et al., "International guidelines for management of metastatic breast cancer: can metastatic breast cancer be cured?," Journal of the National Cancer Institute, Apr. 2010, 102, 456-463.
Pak et al., "Sequence Determinants of Intracellular Phase Separation by Complex Coacervation of a Disordered Protein," Mol Cell, Jul. 2016, 63(1):72-85.
Palmerston Mendes et al., "Dendrimers as Nanocarriers for Nucleic Acid and Drug Delivery in Cancer Therapy," Molecules, Aug. 2017, 22(9):1401.
Palta et al., "Interim Acute Toxicity Analysis and Surgical Outcomes of Neoadjuvant Gemcitabine/nab-Paclitaxel and Hypofractionated Image Guided Intensity Modulated Radiation Therapy in Resectable and Borderline Resectable Pancreatic Cancer (ANCHOR) Study," International Journal of Radiation Oncology • Biology • Physics, Oct. 2016, 96, S204-S205.
Palva et al., "Secretion of interferon by *Bacillus subtilis*," Gene, 1983, 22, 229-235.
Pang et al., "A Modular Method for the High-Yield Synthesis of Site-Specific Protein-Polymer Therapeutics," Angew Chem Int Ed Engl, Jul. 2016, 55, 10296-10300.
Paolino et al., "Folate-targeted supramolecular vesicular aggregates as a new frontier for effective anticancer treatment in in vivo model," Eur. J. Pharm. Biopharm., Jun. 2012, 82(1):94-102.
Paolino et al., "Gemcitabine-loaded PEGylated unilamellar liposomes vs GEMZAR: biodistribution, pharmacokinetic features and in vivo antitumor activity," J. Control. Release Jun. 2010, 144(2):144-150.
Paoloni et al., "Translation of new cancer treatments from pet dogs to humans," Nat. Rev. Cancer Feb. 2008, 8 (2), 147-156.
Papa et al., "PEGylated Liposomal Gemcitabine: Insights Into a Potential Breast Cancer Therapeutic," Cell Oncol. (Dordr), Oct. 2013, 36(6):449-457.
Paramonov et al., "Self-assembly of peptide-amphiphile nanofibers: The roles of hydrogen bonding and amphiphilic packing," J. Am. Chem. Soc., May 2006, 128, 7291-7298.
Pardridge, "The blood-brain barrier: bottleneck in brain drug development," NeuroRx, 2005, 2(1):3-14.
Park et al., "Exendin-4 and exercise improve hepatic glucose homeostasis by promoting insulin signaling in diabetic rats," Metabolism, Janury 2010, 59, 123-133.
Park et al., "Formulation optimization and in vivo proof-of-concept study of thermosensitive liposomes balanced by phospholipid, elastin-like polypeptide, and cholesterol," PLoS One, Jul. 2014, 9: e103116, 13 pages.
Park et al., "Protein stitchery: Design of a protein for selective binding to a specific DNA sequence," PNAS, 1992, vol. 89:9094-9096.
Parker et al., "Antibody mimics based on human fibronectin type three domain engineered for thermostability and high-affinity binding to vascular endothelial growth factor receptor two," Protein Eng Des Sel, 2005, 18(9):435-44.
Parkes et al. "Discovery and development of exenatide: the first antidiabetic agent to leverage the multiple benefits of the incretin hormone, GLP-1," Expert Opinion. Drug Deliv., Feb. 2013, 8(2):219-244.

Parveen et al., "Nanomedicine," Clinical Pharmacokinetics, Oct. 2006, 45(10):965-988.
Pastuszka et al., "A tunable and reversible platform for the intracellular formation of genetically engineered protein microdomains," Biomacromolecules, ACS Publications, Oct. 2012, 13(11):3439-3444.
Patil et al., "Cellular delivery of doxorubicin via pH-controlled hydrazone linkage using multifunctional nano vehicle based on poly(beta-I-malic acid)," Int J Mol Sci, Sep. 2012, 13, 11681-11693.
Peeler et al., "Genetically encoded initiator for polymer growth from proteins," J. Am. Chem. Soc. 132, Oct. 2010, 13575-13577.
Peng et al., "Length-dependent prediction of protein intrinsic disorder," BMC Bioinformatics, Springer Nature, Apr. 2006, 7:208.
Peters, "Serum albumin," Adv. Protein Chem. 37, 1985, 161-245.
Petitdemange et al., "Tuning Thermoresponsive Properties of Cationic Elastin-like Polypeptides by Varying Counterions and Side-Chains," Bioconjug. Chem., May 2017, 28(5):1403-1412.
Petros et al., "Strategies in the design of nanoparticles for therapeutic applications," Nat Rev Drug Discov, Nature Research, Aug. 2010, 9(8):615-27.
Phan et al., "Temperature-responsive self-assembly of charged and uncharged hydroxyethylcellulose-graft-poly(N-isopropylacrylamide) copolymer in aqueous solution," Colloid Polym. Sci., Apr. 2011, 289 (9), 993-1003.
Pinkas et al., "Tunable, post-translational hydroxylation of collagen domains in *Escherichia coli*," ACS Chem. Biol., Apr. 2011, 6(4):320-324.
Pliarchopoulou et al., "Pancreatic cancer: Current and future treatment strategies," Cancer Treatment Reviews, Aug. 2009, 35, 431-436.
Poitout et al., "Glucolipotoxicity: Fuel Excess and β-Cell Dysfunction," Endocr Rev, May 2008, 29(3):351-366.
Pometun et al., "Quantitative observation of backbone disorder in native elastin," J Biol Chem, 2004, 279, 7982-7987.
Popp et al., "Site-specific labeling via sortase-mediated transpeptidation," Curr. Protoc. Protein Sci. 56, Apr. 2009, 15.13.1-15.13.9.
Popp et al., "Sortase-Catalyzed Transformations That Improve The Properties Of Cytokines," PNAS, Feb. 2011, vol. 108, No. 8, pp. 3169-3174.
Potters et al., "12-year outcomes following permanent prostate brachytherapy in patients with clinically localized prostate cancer," The Journal of urology, 2005, 173, 1562-1566.
Potters et al., "Monotherapy for stage T1-T2 prostate cancer: radical prostatectomy, external beam radiotherapy, or permanent seed implantation," Radiotherapy and oncology: journal of the European Society for Therapeutic Radiology and Oncology, 2004, 71, 29-33.
Potters et al., "Potency after permanent prostate brachytherapy for localized prostate cancer," International journal of radiation oncology, biology, physics, 2001, 50(5): 1235-1242.
Potthoff et al., "Endocrine fibroblast growth factors 15/19 and 21: from feast to famine," Genes Dev, Feb. 2012, 26(4):312-324.
Prestwich et al., "Beta dose point kernels for radionuclides of potential use in radioimmunotherapy," J Nucl Med, 1989, 30, 1036-1046.
Privratsky et al., "PECAM-1: regulator of endothelial junctional integrity," Cell Tissue Res, Mar. 2014, 355, 607-619.
Prostate Seed Center, "Brachytherapy seed pre-plan rendering," <http://www.prostateseedcenter.com/dynamics-of-brachytherapy> webpage available as early as Aug. 30, 2012.
Provenzano et al., "Enzymatic targeting of the stroma ablates physical barriers to treatment of pancreatic ductal adenocarcinoma," Cancer cell, Mar. 2012, 21, 418-429.
Provenzano et al., "Hyaluronan, fluid pressure, and stromal resistance in pancreas cancer," Br J Cancer, Jan. 2013, 108, 1-8.
Pulaski et al., "Mouse 4T1 breast tumor model," Curr. Protoc. Immunol., 2001, Chapter 20, Unit 20.2.
Qamar et al., "FUS Phase Separation Is Modulated by a Molecular Chaperone and Methylation of Arginine Cation-pi Interactions," Cell, Apr. 2018, 173(3):720-734.e15.
Qi et al., "A brush-polymer conjugate of exendin-4 reduces blood glucose for up to five days and eliminates poly(ethylene glycol) antigenicity," Nat Biomed Eng, Nov. 2016, 1:0002.

(56) References Cited

OTHER PUBLICATIONS

Qi et al., Dataset for A brush-polymer conjugate of exendin-4 reduces blood glucose for up to five days and eliminates poly(ethylene glycol) antigenicity. Figshare, Nov. 2016, <http://dx.doi.org/10.6084/m9.figshare.3976761>.
Qi et al., "Growing polymers from peptides and proteins: a biomedical perspective," Polym. Chem., Jan. 2014, 5(2):266-276.
Qi et al., "Protein-polymer conjugation—moving beyond PEGylation," Curr. Opin. Chem. Biol. 28, Oct. 2015, 181-193.
Qi et al., "Sortase-catalyzed initiator attachment enables high yield growth of a stealth polymer from the C terminus of a protein," Macromol. Rapid Commun., Aug. 2013, 34(15):1256-1260.
Qiu et al., "Development of Orthotopic Pancreatic Tumor Mouse Models," Methods Mol Biol, Jan. 2013, 980: 215-223.
Qiu et al., "Polymer Architecture and Drug Delivery," Pharmaceutical Research, Feb. 2006, 23(1):1-30.
Quarmby et al., "Irradiation induces upregulation of CD31 in human endothelial cells," Arterioscler Thromb Vasc Biol, 1999, 19, 588-597.
Quarmby et al., "Radiation-induced normal tissue injury: role of adhesion molecules in leukocyte-endothelial cell interactions," Int J Cancer, 1999, 82, 385-395.
Quiroz et al., "Intrinsically disordered proteins access a range of hysteretic phase separation behaviors," Scientific advances, Oct. 2019, 5(10):eaax5177.
Quiroz et al., "Sequence heuristics to encode phase behaviour in intrinsically disordered protein polymers," Nat. Mater., Nov. 2015, 14(11):1164-1171.
Rabotyagova et al., "Protein-based block copolymers," Biomacromolecules, Feb. 2011, 12(2): 269-289.
Radivojac et al., "Intrinsic Disorder and Functional Proteomics," Biophysical Journal, Mar. 2007, vol. 92, Issue 5, pp. 1439-1456.
Ragupathi et al., "Abstract A73: Antitumor activity of MVT-5873, a monoclonal antibody targeting sialyl Lewisa, alone and in combination with gemcitabine/nab-paclitaxel in a BxPC3 human pancreatic cancer xenograft model," Cancer Research, Dec. 2016, 76.
Rankine et al., "Investigating end-to-end accuracy of image guided radiation treatment delivery using a micro-irradiator," Physics in Medicine and Biology, Nov. 2013, 58(21): 7791-7801.
Rao et al., "Synthetic nanoparticles camouflaged with biometric erythrocyte membranes for reduced reticuloendothelial system uptake," Nanotechnology, Jan. 2016, 27 (8), 85106, 9 pages.
Rapaka et al., "Coacervation of Sequential Polypeptide Models of Tropoelastin," Int J Peptide Protein Res, 1978, 11: 97-108.
Ratner et al., "Radiation-grafted hydrogels for biomaterial applications as studied by the ESCA technique," Journal of Applied Polymer Science, 1978, 22, 643-664.
Ratner, "A pore way to heal and regenerate: 21st century thinking on biocompatibility," Regen Biomater, Feb. 2016, 3(2):107-110.
Rauscher et al. "Proline and Glycine Control Protein Self-Organization into Elastomeric or Amyloid Fibrils," Structure, Nov. 2006, 14(11):1667-1676.
Ravikumar et al., "Mimicking adhesive functionalities of blood platelets using ligand-decorated liposomes," Bioconjugate chemistry, ACS Publications, May 2012, 23(6):1266-1275.
Ray et al., "Aptamer-mediated delivery of chemotherapy to pancreatic cancer cells." Nucleic acid therapeutics, Oct. 2012, 22(5): 295-305.
Regier et al., American Heart Association 2014 Scientific Sessions, May 2015, vol. 7, pp. 299-303.
Reguera et al., "Thermal Behavior and Kinetic Analysis of the Chain Unfolding and Refolding and of the Concomitant Nonpolar Solvation and Desolvation of Two Elastin-like Polymers," Macromolecules, 2003, 36, 8470-8476.
Ren et al., "Mesenchymal stem cell-mediated immunosuppression occurs via concerted action of chemokines and nitric oxide," Cell Stem Cell, Feb. 2008, 2(2): p. 141-150.
Ribeiro et al., "Influence of the amino-acid sequence on the inverse temperature transition of elastin-like polypeptides," Biophysical Journal, Jul. 2009, 97(1):312-320.
Richards et al., "Engineered fibronectin type III domain with a RGDWE sequence binds with enhanced affinity and specificity to human avβ3 integrin," J Mol Biol, 2003, 326(5):1475-1488.
Richards et al., "Man's best friend: what can pet dogs teach US about non-Hodgkin lymphoma?" Inmunol Rev., Jan. 2015, 263 (1): 173-191.
Riddles et al., "Ellman's reagent: 5,5'-dithiobis(2-nitrobenzoic acid)—a reexamination," Anal Biochem. 1979, 94(1):75-81.
Riedel et al., "Engineered glucagon-like peptide-1-producing hepatocytes lower plasma glucose levels in mice," Am J Physiol Endocrinol Metab, Apr. 2009, 296(4):E936-E944.
Rincon et al., "Biocompatibility of elastin-like polymer poly(VPAVG) microparticles: in vitro and in vivo studies," Journal of Biomedical Materials Research, 2005, 78A, 343-351.
Rios-Doria et al., "Doxil synergizes with cancer immunotherapies to enhance antitumor responses in syngeneic mouse models," Neoplasia, Aug. 2015, 17(8):661-670.
Ritcher et al., "Antibodies against polyethylene glycol produced in animals by immunization with monomethoxy polyethylene glycol modified proteins," Int. Arch. Allergy Appl. Immunol. 70, 1983, 124-131.
Ritcher et al., "Polyethylene glycol reactive antibodies in man: titer distribution in allergic patients treated with monomethoxy polyethylene glycol modified allergens or placebo, and in healthy blood donors," Int. Arch. Allergy Appl. Immunol. 74, 1984, 36-39.
Rivory et al., "Effects of lipophilicity and protein binding on the hepatocellular uptake and hepatic disposition of two anthracyclines, doxorubicin and iododoxorubicin," Cancer Chemother Pharmacol, 1996, 38(5):439-445.
Roberts et al., "Elastin-like polypeptides as models of intrinsically disordered proteins," FEBS Lett., Sep. 2015, 589, 2477-2486.
Robinet et al. "Elastin-derived peptides enhance angiogenesis by promoting endothelial cell migration and tubulogenesis through upregulation of MT1-MMP," J. Cell Science, 2005, 118:343-356.
Rodriguez-Diaz et al., "Alpha cells secrete acetylcholine as a non-neuronal paracrine signal priming beta cell function in humans," Nat Med, Jun. 2011, 17:888-892.
Rolland et al., "Direct fabrication and harvesting of monodisperse, shape-specific nanobiomaterials," J Am Chem Soc, 2005, 127(28):10096-100.
Römer et al., "The elaborate structure of spider silk: structure and function of a natural high performance fiber," Prion, Nov. 2008, 2(4):154-161.
Roopenian et al., "FcRn: the neonatal Fc receptor comes of age," Nat. Rev. Immunol., Sep. 2007, vol. 7, No. 9, 715-725.
Rosenberg et al., "Present and future innovations in radiation oncology," Surg Oncol Clin N Am, Jul. 2013, 22(3):599-618.
Rosenholm et al., "Towards multifunctional, targeted drug delivery systems using mesoporous silica nanoparticles—opportunities & challenges," Nanoscale, Royal Society of Chemistry, Oct. 2010, 2(10):1870-83.
Rösler et al., "Advanced drug delivery devices via self-assembly of amphiphilic block copolymers," Advanced Drug Delivery Reviews, 2001, 53:95-108.
Rozak et al., "G148-GA3: a streptococcal virulence module with atypical thermodynamics of folding optimally binds human serum albumin at physiological temperatures," Biochim Biophys Acta, 2005, 1753(2): p. 226-33.
Ruiz van Haperen et al., "Regulation of phosphorylation of deoxycytidine and 2',2'-difluorodeoxycytidine (gemcitabine); effects of cytidine 5'-triphosphate and uridine 5'-triphosphate in relation to chemosensitivity for 2',2'-difluorodeoxycytidine," Biochem. Pharmacol. 1996, 51(7):911-908.
Russo et al., "The role of neoadjuvant therapy in pancreatic cancer: a review," Future Oncol, Mar. 2016, 12(5):669-685.
Ryerson et al., "Annual report to the nation on the status of cancer, 1975-2012, featuring the Increasing incidence of liver cancer," Cancer, May 2016, 122(9): 1312-1337.
Ryu et al., "Elastin-like polypeptide for improved drug delivery for anticancer therapy: preclinical studies and future applications," Expert Opinion on Drug Delivery, Informa Healthcare, Oct. 2014, 12(4):653-667.

(56) References Cited

OTHER PUBLICATIONS

Saba et al., "A Comparative Oncology Study of Iniparib Defines Its Pharmacokinetic Profile and Biological Activity in a Naturally-Occurring Canine Cancer Model," PLoS One, Feb. 2016, 11(2): 1-11.

Safran et al., "Gemcitabine, paclitaxel, and radiation for locally advanced pancreatic cancer: A phase I trial," Int J Radiation Oncology Biol Phys, 2002, 54, 137-141.

Sagle et al., "Investigating the hydrogen-bonding model of urea denaturation," J Am Chem Soc, Jun. 2009, 131(26): 9304-9310.

Saifer et al., "Selectivity of binding of PEGs and PEG-like oligomers to anti-PEG antibodies induced by methoxyPEG-proteins," Molecular Immunology, Feb. 2014, 57(2):236-246.

Sandler et al., "Gemcitabine: Single-Agent and Combination Therapy in Non-Small Cell Lung Cancer," Oncologist 1999, 4(3)241-251.

Sanna et al., "Targeted therapy using nanotechnology: focus on cancer," Int J Nanomedicine, Jan. 2014, 9:467-83.

Schaal et al., "Biopolymer ß-brachytherapy delivered with concomitant paclitaxel outperforms traditional x-ray radiation to include complete regression in multiple pancreatic tumor xenograft models through synergistic modulation of the tumor microenvironment," Poster #5831, 2018.

Schaal et al., "Injectable polypeptide micelles that form radiation crosslinked hydrogels in situ for intratumoral radiotherapy," Journal of Controlled Release, Apr. 2016, 228, 58-66.

Schellenberg et al., "Gemcitabine chemotherapy and single-fraction stereotactic body radiotherapy for locally advanced pancreatic cancer," Int J Radiation Oncol Biol Phys,Nov. 2008, 72(3): 678-686.

Schellenberg et al., "Single-fraction stereotactic body radiation therapy and sequential gemcitabine for the treatment of locally advanced pancreatic cancer," Int J Radiation Oncology Biol Phys, Sep. 2011, 81(1): 181-188.

Schellenberger et al., "A recombinant polypeptide extends the in vivo half-life of peptides and proteins in a tunable manner," Nat. Biotechnol., Dec. 2009, 27(12):1186-1188.

Schlaff et al., "Bringing the heavy: carbon ion therapy in the radiobiological clinical context," Radiation Oncology, Mar. 2014, 9, Article 88, 1-18.

Schneider et al., "NIH Image to ImageJ: 25 years of image analysis," Nature Methods, Jul. 2012, 9(7): 671-675.

Schnell et al., "Expression of integrin αvβ3 in gliomas correlates with tumor grade and is not restricted to tumor vasculature," Brain Pathol, International Society of Neuropathology, Aug. 2008, 18(3):378-86.

Schwendeman et al., "Injectable controlled release depots for large molecules," J Control Release, Sep. 2014, 190, 240-253.

Senin et al., "N-Myristoylation of recoverin enhances its efficiency as an inhibitor of rhodopsin kinase," Febs. Lett., 1995, 376, 87-90.

Senior et al., "Val-Gly-Val-Ala-Pro-Gly, a Repeating Peptide in Elastin, Is Chemotactic for Fibroblasts and Monocytes," The Journal of Cell Biology, 1984, 99: 870-874.

Serrano et al., "An infrared spectroscopic study of the conformational transition of elastin-like polypeptides," Biophys. J., Oct. 2007, 93(7):2429-2435.

Shadwick, "Mechanical design in arteries," J Exp Biol, 1999, 202, 3305-3313.

Shang et al., "pH-Dependent Protein Conformational Changes in Albumin:Gold Nanoparticle Bioconjugates: A Spectroscopic Study," Langmuir, Feb. 2007, 23 (5), 2714-2721.

Shao et al., "Super-resolution 3D microscopy of live whole cells using structured illumination," Nat Methods, Oct. 2011, 8(12):1044-1046.

Sharma et al., "Dendrimer nanoarchitectures for cancer diagnosis and anticancer drug delivery," Drug Discov Today, Feb. 2017, 22(2):314-326.

Sharma et al., "PLGA-based nanoparticles: A new paradigm in biomedical applications, " TrAC Trends in Analytical Chemistry, Jun. 2016, 80:30-40.

Sharma et al., "Polymer particle shape independently influences binding and internalization by macrophages," Journal of Controlled Release, Elsevier, Nov. 2010, 147(3):408-412.

Shen et al., "Conjugation site modulates the in vivo stability and thearpeutic activity of antibody-drug conjugates," Nat Biotechnol, Jan. 2012, 30(2):184-189.

Sheparovych et al., "Stimuli-Responsive Properties of Peptide-Based Copolymers Studied via Directional Growth of Self-Assembled Patterns on Solid Substrate," Biomacromolecules, Jul. 2009, 10:1955-1961.

Sherman et al., "Next-Generation PEGylation Enables Reduced Immunoreactivity of PEG-Protein Conjugates," Drug and Development & Delivery, Jun. 2012, vol. 12, No. 5, 36-42.

Sherman et al., "Role of the Methoxy Group in Immune Responses to mPEG-Protein Conjugates," Bioconjugate Chemistry, Mar. 2012, 23(3): 485-499.

Shi et al., "Cell adhesion on a POEGMA-modified topographical surface," Langmuir: the ACS journal of surfaces and colloids, Dec. 2012, 28 (49), 17011-8.

Shi et al., "Triggered sorting and co-assembly of genetically engineered protein microdomains in the cytoplasm," Adv Mater, Wiley, Jan. 2014, 26(3):449-454.

Shimoboji et al., "Temperature-Induced Switching of Enzyme Activity with Smart Polymer-Enzyme Conjugates," Bioconjugate Chem. 2003, 14, 517-525.

Shin et al., "Liquid phase condensation in cell physiology and disease," Science, Sep. 2017, 357(6357):eaaf4382.

Shusharina et al., "Micelles of Diblock Copolymers with Charged and Neutral Blocks: Scaling and Mean-Field Lattice Approaches," Macromolecules, 2000, 33(10): 3892-3901.

Sickmeier et al., "DisProt: the Database of Disordered Proteins," Nucleic Acids Res, Oxford Academy, Jan. 2007, 35:D786-793.

Siegel et al., "Absorbed fractions for electrons and beta particles in spheres of various sizes," J Nucl Med, 1994, 35, 152-156.

Siegwart et al., "ATRP In The Design Of Functional Materials For Biomedical Applications," Prog Polymer Science, Jan. 2012, vol. 37, No. 1, pp. 18-37.

Silberstein et al., "The SNM Practice Guideline for Therapy of Thyroid Disease with $^{131}$I, 3.0," J Nucl Med, Jul. 2012, 53, 1-19.

Silva et al., "Selective differentiation of neural progenitor cells by high-epitope density nanofibers," Science, 2004, 303, 1352-5.

Simakova et al., "Aqueous ARGET ATRP," Macromolecules, Aug. 2012, 45(16):6371-6379.

Simnick et al., "In vivo tumor targeting by a NGR-decorated micelle of a recombinant diblock copolypeptide," J Control Release, Oct. 2011, 155(2): 144-151.

Simnick et al., "Morphing low-affinity ligands into high-avidity nanoparticles by thermally triggered self-assembly of a genetically encoded polymer," ACS Nano, Apr. 2010, 4(4):2217-2227.

Simon et al., "Engineered Ribonucleoprotein Granules Inhibit Translation in Protocells," Molecular cell, Jul. 2019, 75(1):66-75.

Simon et al., "Programming molecular self-assembly of intrinsically disordered proteins containing sequences of low complexity," Nat Chem, Jun. 2017, 9(6):509-515.

Singhal et al., "Fibroblast Growth Factor 21 (FGF21) Protects against High Fat Diet Induced Inflammation and Islet Hyperplasia in Pancreas," PLoS One, Feb. 2016, 11(2):e0148252.

Sisson et al., "Radiation safety in the treatment of patients with thyroid diseases by radioiodine 131I: practice recommendations of the American Thyroid Association," Thyroid, Apr. 2011, 21(4):335-346.

Skerra, "Alternative non-antibody scaffolds for molecular recognition," Curr Opin Biotechnol, Elsevier, Aug. 2007, 18(4):295-304.

Smith et al., "The Role of Beta Cell Glucagon-like Peptide-1 Signaling in Glucose Regulation and Response to Diabetes Drugs," Cell Metab, Jun. 2014, 19(6):1050-1057.

Smits et al., "Elastin-Like Polypeptide Based Nanoparticled: Design Rationale Toward Nanomedicine," Macromolecular Bioscience, Macromolecular Journals, Jan. 2015, 15(1):36-51.

Sonawane et al., "Hydrazo linkages in pH responsive drug delivery systems," European Journal Pharmaceutical Sciences, Mar. 2017, 99, 45-65.

(56) References Cited

OTHER PUBLICATIONS

Sorkin et al., "Signal transduction and endocytosis: close encounters of many kinds," Nat Rev Mol Cell Biol, 2002, 3(8):600-614.
Sousa et al., "Production of a polar fish antimicrobial peptide in *Escherichia coli* using an ELP-intein tag," J Biotechnol, Sep. 2016, 234:83-89.
Sriraman et al., "Barriers to drug delivery in solid tumors," Tissue Barriers, Jul. 2014, 2(3): 2-10.
Stanislaus et al., "A Novel Fc-FGF21 With Improved Resistance to Proteolysis, Increased Affinity Toward β-Klotho, and Enhanced Efficacy in Mice and Cynomolgus Monkeys," Endocrinology, May 2017, 158(5):1314-1327.
Stefl et al., "RNA sequence-and shape-dependent recognition by proteins in the ribonucleoprotein particle" EMBO reports (2005) 6(1):33-38.
Steichen et al., "A Review of Current Nanoparticle and Targeting Moieties for the Delivery of Cancer Therapeutics," Eur J Pharm Sci, Elsevier, Feb. 2013, 48(3):416-27.
Stock et al., "Penile erectile function after permanent raioactive seed implantation for treatment of prostate cancer," The Journal of urology, 2001, 165, 436-439.
Stork et al., "A novel tri-functional antibody fusion protein with improved pharmacokinetic properties generated by fusing a bispecific single-chain diabody with an albumin-binding domain from streptococcal protein G," Protein Engineering Design and Selection, Nov. 2007, 20(11): p. 569-576.
Strohmaier et al., "Comparison of $^{60}$Co and $^{192}$Ir sources in HDR brachytherapy," J Contemp Brachyther, Dec. 2011, 3(4): 199-208.
Strulson et al., "RNA catalysis through compartmentalization," Nat Chem, Nature Publishing Group, Nov. 2012, 4(11):941-946.
Stutz et al., "Seed loss through the urinary tract after prostate brachytherapy: examining the role of cystoscopy and urine straining post implant," Medical physics, 2003, 30, 2695-2698.
Sugyo et al., "Evaluation of efficacy of radioimmunotherapy with 90Y-labeled fully human anti-transferring receptor monoclonal antibody in pancreatic cancer mouse models," PLoS One, Apr. 2015, 10, 1-17.
Suk et al., "PEGylation as a Strategy for Improving Nanoparticle-Based Drug and Gene Delivery," Adv Drug Deliv Rev, Apr. 2016, 99(Pt A):28-51.
Sumerlin, "Proteins as Initiators of Controlled Radical Polymerization: Grafting-from via ATRP and Raft," ACS Macro Lett. Jan. 2012, 1(1): 141-145.
Sun et al., "Autofluorescence Imaging of Living Pancreatic Islets Reveals Fibroblast Growth Factor-21 (FGF21)-Induced Metabolism," Biophys J, Dec. 2012, 103(11):2379-2388.
Sun et al., "Contributions of the extracellular and cytoplasmic domains of platelet-endothelial cell adhesion molecule-1 (PECAM-1/CD31) in regulating cell-cell localization," J. Cell Sci., 2000, 113, 1459-1469.
Sun et al., "Efficacy and safety of the hypoxia-activated prodrug TH-302 in combination with gemcitabine and nab-paclitaxel in human tumor xenograft models of pancreatic cancer," Cancer Biology & Therapy, Feb. 2015, 16(3): 438-449.
Sun et al., "EUS-guided interstitial brachytherapy of the pancreas: a feasibility study," Gastrointestinal Endoscopy, 2005, 62, 775-779.
Sun et al., "On the Thermally Reversible Dynamic Hydration Behavior of Oligo(ethylene glycol) Methacrylate-Based Polymers in Water," Macromolecules, Jan. 2013, 46(1): 236-246.
Sunamura et al., "Gene Therapy for Pancreatic Cancer Targeting the Genomic Alterations of Tumor Suppressor Genes using Replication-selective Oncolytic Adenovirus," Human Cell, 2002, 15, 138-150.
Surwit et al., Diet-induced type II diabetes in C57BL/6J mice, Diabetes 37, 1988, 1163-1167.
Sussman et al., "Porous implants modulate healing and induce shifts in local macrophage polarization in the foreign body reaction," Ann Biomed Eng, Jul. 2014, 42(7): 1508-1516.
Swee et al., "Sortase-mediated modification of αDEC205 affords optimization of antigen presentation and immunization against a set of viral epitopes," Proc Natl Acad Sci USA, Jan. 2013, 110(4):1428-1433.
Swers et al., Multivalent Scaffold Proteins as Superagonists of TRAIL Receptor 2-Induced Apoptosis, Mol Cancer Ther, Jul. 2013, 12(7): 1235-1244.
Swider et al., "Customizing Poly(lactic-Co-Glycolic Acid) Particles for Biomedical Applications," Acta Biomater, Jun. 2018, 73:38-51.
Takalkar et al., "Radium-223 dichloride bone-targeted alpha particle therapy for hormone-refractory breast cancer metastatic to bone," Exp Hematol Oncol, Sep. 2014, 8, Article No. 23.
Talelli et al., "Core-Crosslinked Polymeric Micelles: Principles, Preparation, Biomedical Applications and Clinical Translation," Nano Today, Feb. 2015, 10(1):93-117.
Tallarida, "Quantitative methods for assessing drug synergism," Genes & Cancer, Nov. 2011, 2(11): 1003-1008.
Talukdar et al., "A Long-Acting FGF21 Molecule, PF-05231023, Decreases Body Weight and Improves Lipid Profile in Non-human Primates and Type 2 Diabetic Subjects," Cell Metab, Mar. 2016, 23(3):427-440.
Tamburro et al., "Dissection of human tropoelastin: exon-by-exon chemical synthesis and related conformational studies," Biochemistry, 2003, 42, 13347-13362.
Tamburro et al., "Localizing alpha-helices in human tropoelastin: assembly of the elastin "puzzle"," Biochemistry, Aug. 2006, 45(31): 9518-9530.
Tan et al., "Characterization of a new primary human pancreatic tumor line," Cancer investigation, 1986, 4, 15-23.
Tang et al., "Combinatorial codon scrambling enables scalable gene synthesis and amplification of repetitive proteins," Nature Mater., Apr. 2016, 15(4): 419-424.
Tang et al., "Enzymatic Polymerization of High Molecular Weight DNA Amphiphiles That Self-Assemble into Star-Like Micelles," Advanced Materials, Feb. 2014, 26(19): 3050-3054.
Tang et al., "High-Molecular-Weight Polynucleotides by Transferase-Catalyzed Living Chain-Growth Polycondensation," Angew. Chem., Jun. 2017, 56(24): 6778-6782.
Tang et al., "Identification of PECAM-1 in solid tumor cells and its potential involvement in tumor cell adhesion to endothelium," J. Biol. Chem., 1993, 268, 22883-22894.
Tantakitti et al., "Energy landscapes and functions of supramolecular systems," Nat. Mater., Apr. 2016, 15(4): 469-476.
Tedja et al., "Effect of TiO2 nanoparticle surface functionalization on protein adsorption, cellular uptake and cytotoxicity: the attachment of PEG comb polymers using catalytic chain transfer and thiol-ene chemistry," Polymer Chemistry, Oct. 2012, 3 (10), 2743-2751.
Teicher, "In vivo/ex vivo and in situ assays used in cancer research: a brief review," Toxicol. Pathol., Jan. 2009, 37 (1), 114-122.
Thakor et al., "Clinically Approved Nanoparticle Imaging Agents," J Nucl Med, Oct. 2016, 57(12):1833-1837.
Theillet et al., "The alphabet of intrinsic disorder: I. Act like a Pro: On the abundance and roles of proline residues in intrinsically disordered proteins," Intrinsically Disord Proteins, Taylor & Francis, Apr. 2013, 1(1):e24360.
Therasse et al., "New guidelines to evaluate the response to treatment in solid tumors," J Natl Cancer Inst, 2000, 92, 205-216.
Thorens et al., "Cloning and functional expression of the human islet GLP-1 receptor: demonstration that Exendin-4 Is an agonist and Exendin-(9-39) an antagonist of the receptor," Diabetes 42, 1993, 1678-1682.
Tomiyama et al., "Relevant use of Klotho in FGF19 subfamily signaling system in vivo," Proc Natl Acad Sci USA, Jan. 2010, 107(4):1666-71.
Tompa et al., "Fuzzy complexes: polymorphism and structural disorder in protein-protein interactions," Trends Biochem Sci, Jan. 2008, 33(1): 2-8.
Tong et al., "Protein Modification with Amphiphilic Block Copoly(2-oxazoline)s as a New Platform for Enhanced Cellular Delivery," Mol. Pharm., Aug. 2010, vol. 7, No. 4, pp. 984-992.
Ton-That et al., "Assembly of pili on the surface of *Corynebacterium diptheriae*," 2003, 50(4):1429-1438.

(56) References Cited

OTHER PUBLICATIONS

Ton-That et al., "Purification and characterization of sortase, the transpeptide that cleaves surface proteins of *Staphylococcus aureus* and the LPXTG motif," Proc Natl Acad Sci USA, 1999, 96(22):12424-12429.
Torchilin, "Recent advances with liposomes as pharmaceutical carriers," Nature Rev. Drug Discov. 2005, 4(2):145-160.
Towler et al., "Purification and Characterization of Yeast Myristoyl-Coa-Protein N-Myristoyltransferase," P Natl Acad Sci USA, 1987, 84(9):2708-12.
Trabbic-Carlson et al., "Effect of protein fusion on the transition temperature of an environmentally responsive elastin-like polypeptide: a role for surface hydrophobicity?," Protein Engineering Design and Selection, 2004, 17(1): 57-66.
Trabbic-Carlson et al., "Expression and purification of recombinant proteins from *Escherichia coli*: Comparison of an elastin-like polypeptide fusion with an oligohistidine fusion" Protein Science, 2004, 13: 3274-3284.
Trakul et al., "Stereotactic body radiotherapy in the treatment of pancreatic cancer," Semin Radiat Oncol, Apr. 2014, 24(2): 140-147.
Trieu et al., "P0157 Preclinical evaluation of NBN-paclitaxel in pancreatic cancer xenograft models," Eur J Cancer, May 2014, 50(4): e53.
Triola et al., "Chemical biology of lipidated proteins," ACS Chemical Biology, Jan. 2012, 7(1): 87-99.
Troyanskaya et al., "Nonparametric methods for identifying differentially expressed genes in microarray data," Bioinformatics, 2002, 18(11):1454-61.
Truong et al., "Polymeric filomicelles and nanoworms: two decades of synthesis and application," Polymer Chemistry, Jun. 2016, 7(26):4295-4312.
Truong et al., "The Importance of Nanoparticle Shape in Cancer Drug Delivery," Expert Opin Drug Deliv, Jan. 2015, 12(1):129-42.
Truong, et al., "The effect of hydration on molecular chain mobility and the viscoelastic behavior of resilin-mimetic protein-based hydrogels," Biomaterials, Elsevier, Nov. 2011, 32(33):8462-73.
Tsarevsky et al., "Deactivation efficiency and degree of control over polymerization in ATRP in protic solvents," Macromolecules 37, 2004, 9768-9778.
Tschöp et al., "Unimolecular Polypharmacy for Treatment of Diabetes and Obesity," Cell Metab, Jul. 2016, 24(1):51-62.
Tsume et al., "The development of orally administrable gemcitabine prodrugs with D-enantiomer amino acids: Enhanced membrane permeability and enzymatic stability," Eur. J. Pharm. Biopharm., Apr. 2014, 86(3):514-523.
Tu et al., "Stages in tropoelastin coalescence during synthetic elastin hydrogel formation," Micron, Apr. 2010, 41(3): 268-272.
Turunen et al., "Paclitaxel Succinate Analogs: Anionic Introduction as a Strategy to Impart Blood Brain Barrier Permeability," Bioorg Med Chem Lett, Nov. 2008, 18(22):5971-5974.
Tward et al., "Survival of men with clinically localized prostate cancer treated with prostatectomy, brachytherapy, or No. definitive treatment: impact of age at diagnosis," Cancer, Oct. 2006, 107(10):2392-2400.
Uchida et al., "Potential of adenovirus-mediated REIC/Dkk-3 gene therapy for use in the treatment of pancreatic cancer," Journal of Gastroenterology and Hepatology, Apr. 2014, 29(5): 973-983.
Urry et al., "Calculation of distorted circular dichroism curves for poly-L-glutamic acid suspensions," Arch Biochem Biophys, 1970, 137, 214-221.
Urry et al., "Coacervation of solubilized elastin effects a notable conformational change," Nature, 1969, 222, 795-796.
Urry et al., "Differential scatter of left and right circularly polarized light by optically active particulate systems," Proc Natl Acad Sci U S A, 1970, 65, 845-852.
Urry et al., "Distortions in circular dichroism patterns of particulate (or membranous) systems," Arch Biochem Biophys, 1968, 128, 802-807.
Urry et al., "Elastic protein-based polymers in soft tissue augmentation and generation," J. Biomater. Sci. Polym. Ed., 1998, 9, 1015-1048.
Urry et al., "Hydrophobicity Scale for Proteins Based on InverseTemperature Transitions," Biopolymers, 1992, 32:1243-1250.
Urry et al., "Physical chemistry of biological free energy transduction as demonstrated by elastic protein-based polymers," J. of Phys. Chem. B., 1997, 101, 11007-11028.
Urry et al., "Temperature dependence of length of elastin and its polypentapeptide," Biochem Biophys Res Commun, 1986, 141, 749-755.
Urry et al., "Temperature of polypeptide inverse temperature transition depends on mean residue hydrophobicity," J. Am. Chem. Soc., 1991, 113(11):4346-4348.
Urry, "Free energy transduction in polypeptides and proteins based on inverse temperature transitions," Prog Biophys Mol Biol, Jan. 1992, 57(1):23-57.
Urry, "Protein elasticity based on conformations of sequential polypeptides: The biological elastic fiber," J Protein Chemistry, 1984, 3, 403-436.
Uversky et al., "Intrinsically disordered proteins as crucial constituents of cellular aqueous two phase systems and coacervates," FEBS Lett, Jan. 2015, 589(1):15-22.
Uversky et al., "Understanding protein non-folding," Biochim Biophys Acta, Elsevier, Jun. 2010, 1804(6):1231-1264.
Valkenburg et al., "Targeting the tumour stroma to improve cancer therapy," Nature Reviews Clinical Oncology, Jun. 2018, 15, 366-381.
Van der Lee et al., "Classification of intrinsically disordered regions and proteins," Chem Rev, Jul. 2014, 114(13): 6589-6631.
Van Roey et al., "Short linear motifs: ubiquitous and functionally diverse protein interaction modules directing cell regulation," Chem Rev, Jully 2014, 114(13): 6733-6778.
Van Roy, "Beyond E-cadherin: roles of other cadherin superfamily members in cancer," Nat Rev Cancer, Feb. 2014, 14(2): 121-134.
Vasey et al., "Phase I clinical and Pharmacokinetic study of PK1 (N-(2-Hydroxypropyl)methacrylamide Copolymer Doxorubicin): First member of a New Class of Chemotherapeutic Agents-Drugs-Polymer Conjugates" Clinical Cancer Research, 1999, 5:83-94.
Vazquez-Lombardi et al., "Challenges and Opportunities for Non-Antibody Scaffold Drugs," Drug Discov Today, Oct. 2015, 20(10):1271-83.
Vega et al., "Targeting Doxorubicin to Epidermal Growth Factor Receptors by Site-Specific Conjugation of C225 to Poly(L-Glutamic Acid) through a Polyethylene Glycol Spacer," Pharmaceutical Research, 2003, 20(5):826-832.
Venkataraman et al., "The Effects of Polymeric Nanostructure Shape on Drug Delivery," Adv Drug Deliv Rev, Elsevier, Nov. 2011, 63(14-15):1228-46.
Verma et al., "Effect of surface properties on nanoparticle-cell interactions," Small, Wiley, Jan. 2010, 6(1):12-21.
Veronese et al., "PEGylation, successful approach to drug delivery," Drug Discovery Today, 2005, 10(21):1451-1458.
Veronese, "Peptide and protein PEGylation: a review of problems and solutions," Biomaterials 22, 2001, 405-417.
Vicini et al., "An interinstitutional and interspecialty comparison of treatment outcome data for patients with prostate carcinoma based on predefined prognostic categories and minimum follow-up," Cancer, 2002, 95, 2126-2135.
Viegas et al., " Polyoxazoline: Chemistry, properties and applications," Bioconjugate Chem., May 2011, 22(5): 976-986.
Vlieghe et al., "Synthetic therapeutic peptides: science and market," Drug Discovery Today, Jan. 2010, 15(1-2): 40-56.
Voelker et al., "Alteration of the specificity and regulation of fatty acid synthesis of *Escherichia coli* by expression of a plant medium-chain acyl-acyl carrier protein thioesterase," J Bacteriol., 1994, 176(23):7320-7.
Volkova et al., "Anthracycline Cardiotoxicity: Prevalence, Pathogenesis and Treatment," Curr. Cardiol. Rev., Nov. 2011, vol. 7, No. 4, pp. 214-220.

(56) References Cited

OTHER PUBLICATIONS

Von Roemeling et al., "Breaking Down the Barriers to Precision Cancer Nanomedicine," Trends Biotechnol, Feb. 2017, 35(2):159-171.
Vonarbourg et al., "Evaluation of pegylated lipid nanocapsules versus complement system activation and macrophage uptake," J Biomed Mater Res A, Wiley, Sep. 2006, 78(3):620-8.
Vrhovski et al., "Biochemistry of tropoelastin," Eur J Biochem, 1998, 258, 1-18.
Vrhovski et al., "Coacervation Characteristics of Recombinant Human Tropoelastin," European Journal of Biochemistry, 1997, 250(1):92-98.
Vrignaud et al., "Strategies for the nanoencapsulation of hydrophilic molecules in polymer-based nanoparticles," Biomaterials, Nov. 2011, 32(33):8593-8604.
Walczak, "Death Receptor-Ligand Systems in Cancer, Cell Death, and Inflammation," Cold Spring Harb. Perspect. Biol., May 2013, 5(5): a008698.
Wali et al., "Measuring Death of Pancreatic Beta Cells in Response to Stress and Cytotoxic T Cells," Methods in Molecular Biology, Mar. 2015, 1292:165-176.
Walsh et al., "Post-translational modifications in the context of therapeutic proteins," Nat. Biotechnol., Oct. 2006, 24(10): 1241-1252.
Walsh et al., "Posttranslationale Proteinmodifikation: die Chemie der Proteomdiversifizierung," Angew Chem, 2005, 117, 7508-7539.
Walsh et al., "Protein posttranslational modifications: The chemistry of proteome diversifications," Angew. Chem. Int. Ed., 2005, 44, 7342-7372.
Wang et al., "A Molecular Grammar Governing the Driving Forces for Phase Separation of Prion-like RNA Binding Proteins," Cell, Jul. 2018, 174(3):688-699.e616.
Wang et al., "Enhanced Tumor Delivery of Gemcitabine via PEG-DSPE/TPGS Mixed Micelles," Mol. Pharm., Apr. 2014, 11(4): 1140-1150.
Wang et al., "Extending Half Life of H-Ferritin Nanoparticle by Fusing Albumin Binding Domain for Doxorubicin Encapsulation," Biomacromolecules, Mar. 2018, 19(3):773-781.
Wang et al., "More effective nanomedicines through particle design," Small, Wiley, Jul. 2011, 7(14):1919-31.
Wang et al., "Nanoparticle delivery of cancer drugs," Annu Rev Med, Annual Reviews, Feb. 2012, 63:185-98.
Wang et al., "Quantitative Mapping of the Spatial Distribution of Nanoparticles in Endo-Lysosomes by Local pH," Nano Lett., Feb. 2017, 17(2): 1226-1232.
Wang et al., "Size and dynamics of caveolae studied using nanoparticles in living endothelial cells," ACS nano, Dec. 2009, 3(12): p. 4110-4116.
Wang et al., "Stimuli-responsive Dendrimers in Drug Delivery," Biomater Sci, Mar. 2016, 4(3):375-90.
Wang et al., "The Weak Link: Optimization of the Ligand-Nanoparticle Interface To Enhance Cancer Cell Targeting by Polymer Micelles," Nano Lett Oct. 2017, 17(10):5995-6005.
Waterman et al., "Edema associated with I-125 or Pd-103 prostate brachytherapy and its impact on post-implant dosimetry: an analysis based on serial CT acquisition," International journal of radiation oncology, biology, physics, 1998, 41, 1069-1077.
Wechsel et al., "Renal Cell Carcinoma: Immunohistological Investigation of Expression of the Integrin $\alpha v \beta 3$," Anticancer research, 1999, 19(2C):1529-1532.
Wei et al., "Anticancer drug nanomicelles formed by self-assembling amphiphilic dendrimer to combat cancer drug resistance," Proceedings of the National Academy of Sciences of the United States of America, Mar. 2015, 112(10): 2978-2983.
Wei et al., "Fibroblast growth factor 21 promotes bone loss by potentiating the effects of peroxisome proliferator-activated receptor $\gamma$," Proc Natl Acad Sci USA, Feb. 2012, 109(8):3143-3148.
Weis et al., "$\alpha V$ Integrins in Angiogenesis and Cancer," Cold Spring Harb Perspect Med, Cold Spring Harbor Laboratory Press, Sep. 2011, 1(1):a006478.
Weitzhandler et al., "Micellar Self-Assembly of Recombinant Resilin-/Elastin-Like Block Copolypeptides," Biomacromolecules, Aug. 2017, 18(8):2419-2426.
Wendt et al., "DNA-mediated Folding and Assembly of MyoD-E47 Heterodimers," Journal of Biol. Chem., 1998, 273(10):5735-5743.
Wente et al., "Fibroblast Growth Factor-21 Improves Pancreatic $\beta$-Cell Function and Survival by Activation of Extracellular Signal-Regulated Kinase 1/2 and Akt Signaling Pathways," Diabetes, Sep. 2006, 55(9):2470-2478.
Werle et al., "Strategies to improve plasma half life time of peptide and protein drugs," Amino Acids 30, Jun. 2006, 30(4):351-367.
Wienkers et al., "Predicting in vivo drug interactions from in vitro drug discovery data," Nat. Rev. Drug. Discov. 2005, 4(10):825-833.
Wilkins et al., "Hydrodynamic Radii of Native and Denatured Proteins Measured by Pulse Field Gradient NMR Techniques," Biochemistry, 1999, 38(50):16424-16431.
Williams et al., "Targeted radionuclide therapy," Medical Physics, Jul. 2008, 35(7): 3062-3068.
Williamson et al., "Efficient N-terminal labeling of proteins by use of sortase," Angew Chem Int ed Engl, Sep. 2012, 51(37):9377-9380.
Wimley et al., "Experimentally determined hydrophobicity scale for proteins at membrane interfaces," Nature Structural & Molecular Biology, 1996, 3(10):842-848.
Winzell et al., "The high-fat diet-fed mouse: a model for studying mechanisms and treatment of impaired glucose tolerance and type 2 diabetes," Diabetes 53, 2004, S215-S219.
Wold, "In vivo chemical modification of proteins," Annu. Rev. Med., 1981, 50, 783-814.
Wood et al., "Experiences Using Chloramine-T and 1,3,4,6-Tetrachloro-3-Alpha,6-Alpha-Diphenylglycoluril (Iodogen) for Radioiodination of Materials for Radioimmunoassay," J Clin Chem Clin Bio, 1981, 19, 1051-1056.
Wright et al., "Intrinsically disordered proteins in cellular signalling and regulation," Nat Rev Mol Cell Biol, Jan. 2015, 16(1):18-29.
Wright et al., "Self-assembly of block copolymers derived from elastin-mimetic polypeptide sequences," Advanced Drug Delivery Reviews, 2002, 54, 1057-1073.
Wright et al., "Thermoplastic elastomer hydrogels via self-assembly of an elastin-mimetic triblock polypeptide," Advanced Functional Materials, 2002, 12, 149-154.
Wu et al., "Site-specific chemical modification of recombinant proteins produced in mammalian cells by using the genetically encoded aldehyde tag," Proc Natl Acad Sci USA, Mar. 2009, 106(9):3000-3005.
Wu et al., "Sortase A-Catalyzed Transpeptidation of Glycosylphosphatidylinositol Derivatives for Chemoenzymatic Synthesis of GPI-Anchored Proteins," J. Am. Chem. Soc., Feb. 2010, 132(5): 1567-1571.
Wust et al., "Hyperthermia in combined treatment of cancer," The Lancet Oncology, 2002, 3, 487-497.
Xavier et al., "HPLC Method for the Dosage of Paclitaxel in Copaiba Oil: Development, Validation, Application to the Determination of the Solubility and Partition Coefficients," Chromatographia, Apr. 2016, 79(7-8): 405-412.
Xia et al., "Tunable self-assembly of genetically engineered silk—elastin-like protein polymers," Biomacromolecules, Nov. 2011, 12(11): 3844-3850.
Xie et al., "The Effect of Shape on Cellular Uptake of Gold Nanoparticles in the Forms of Stars, Rods, and Triangles," Sci Rep, Jun. 2017, 7(1):3827.
Xiong et al., "Engineering of amphiphilic block copolymers for polymeric micellar drug and gene delivery," J Control Release, Elsevier, Oct. 2011, 155(2):248-61.
Xu et al., "A quality by design (QbD) case study on liposomes containing hydrophilic API: Il. Screening of critical variables, and establishment of design space at laboratory scale," Int. J. Pharm., Feb. 2012, 423(2):543-553.
Xu et al., "Downregulation of GLP-1 and GIP Receptor Expression by Hyperglycemia," Diabetes, Jun. 2007, 56(6):1551-58.
Xu et al., "Exendin-4 stimulates both beta-cell replication and neogenesis, resulting in increased beta-cell mass and improved glucose tolerance in diabetic rats," Diabetes 48, 1999, 2270-2276.

(56) References Cited

OTHER PUBLICATIONS

Xu et al., "Fibroblast Growth Factor 21 Reverses Hepatic Steatosis, Increases Energy Expenditure, and Improves Insulin Sensitivity in Diet-Induced Obese Mice," Diabetes, Jan. 2009, 58(1):250-259.
Xu et al., "Genetically engineered block copolymers: influence of the length and structure of the coiled-coil blocks on hydrogel self-assembly," Pharm Res, Mar. 2008, 25, 674-682.
Xu et al., "Inorganic nanoparticles as carriers for efficient cellular delivery," Chemical Engineering Science, Elsevier, Feb. 2006, 61(3):1027-1040.
Xu et al., "Role of pancreatic stellate cells in pancreatic cancer metastasis," Am J of Pathology, Nov. 2010, 177(5): 2585-2596.
Xu et al., "Self-assembly behavior of peptide amphiphiles (PAS) with different length of hydrophobic alkyl tails," Colloids Surfaces B Biointerfaces, Nov. 2010, 81(1): 329-335.
Yamamoto et al., "ATRP Synthesis of Thermally Responsive Molecular Brushes from Oligo(ethylene oxide) Methacrylates," Macromolecules, Dec. 2007, 40(26): 9348-9353.
Yang et al., "Long Term Exendin-4 Treatment Reduces Food Intake and Body Weight and Alters Expression of Brain Homeostatic and Reward Markers," Endocrinology, Sep. 2014, 155(9): 3473-3483.
Yang et al., "Poly(carboxybetaine) nanomaterials enable long circulation and prevent polymer-specific antibody production," Nano Today, Feb. 2014, 9(1):10-16.
Yates et al., "Contemporary management of patients with high-risk non-muscle-invasive bladder cancer who fail intravesical BCG therapy," World journal of urology, May 2011, 29(4): 415-422.
Yeo et al., "Coacervation of tropoelastin," Adv Colloid Interface Sci, Sep. 2011, 167(1-2): 94-103.
Yokoe et al., "Albumin-conjugated PEG liposome enhances tumor distribution of liposomal doxorubicin in rats," International Journal of Pharmaceutics, May 2008, 353(1-2): 28-34.
Yoo et al., "A systemic Small RNA Signaling System in Plants" The Plant Cell (2004) vol. 16, pp. 1979-2000.
Yoo et al., "Biodegradable Nanoparticles Containing Doxorubicin-Plga Conjugate for Sustained Release," Pharm. Res., 1999, 16(7):1114-1118.
Youn et al., "Evaluation of therapeutic potentials of site-specific PEGylated glucagon-like peptide-1 isomers as a type 2 anti-diabetic treatment: Insulinotropic activity, glucose-stabilizing capability, and proteolytic stability" Biochem. Pharmacol, 2007, 73: 84-93.
Youn et al., "High-yield production of biologically active mono-PEGylated salmon calcitonin by site-specific PEGylation," J. Control. Release, Feb. 2007, 117(3):371-379.
Yousefpour et al., "Co-opting biology to deliver drugs," Biotechnol Bioeng, Sep. 2014, 111(9): p. 1699-1716.
Yousefpour et al., "Genetically Encoding Albumin Binding into Chemotherapeutic-loaded Polypeptide Nanoparticles Enhances Their Antitumor Efficacy," Nano Lett., Dec. 2018, 18(12): 7784-7793.
Yu et al., "Effectiveness and security of CT-guided percutaneous implantation of (125)I seeds in pancreatic carcinoma, " The British journal of radiology, Jul. 2014, 87(1039): 20130642, 7 pages.
Yusta et al., "GLP-1 receptor activation improves β cell function and survival following induction of endoplasmic reticulum stress," Cell Metab, Nov. 2006, 4(5):391-406.
Zhang et al., "A self-assembly pathway to aligned monodomain gels," Nat. Mater., Jul. 2010, 9(7): 594-601.
Zhang et al., "In Depth Analysis on the Unusual Multistep Aggregation Process of Oligo(ethylene glycol) Methacrylate-Based Polymers in Water," Macromolecules, Jul. 2014, 47(14): 4728-4737.
Zhang et al., "Nanoparticles in medicine: therapeutic applications and developments," Clin. Pharmacol. Ther., May 2008, 83(5):761-769.
Zhang et al., "Novel agents for pancreatic ductal adenocarcinoma: emerging therapeutics and future directions," Jounral of Hematology & Oncology, Jan. 2018, 11:14, 17 pages.
Zhang et al., "Sensitive and Quantitative Detection of Anti-Poly(ethylene glycol) (PEG) Antibodies by Methoxy-PEG-Coated Surface Plasmon Resonance Sensors," Anal Chem, Aug. 2017, 89(16): 8217-8222.
Zhang et al., "Shape Effects of Nanoparticles Conjugated with Cell-Penetrating Peptides (HIV Tat PTD) on CHO Cell Uptake," Bioconjugate Chem, Sep. 2008, 19(9):1880-1887.
Zhao et al., "A new Bliss Independence model to analyze drug combination data," J Biomol Screen, Jun. 2014, 19(5): 817-821.
Zhao et al., "Cellular uptake, intracellular trafficking, and cytotoxicity of nanomaterials," Small, Wiley, May 2011, 7(10):1322-37.
Zhao et al., "Fluorescence probe techniques used to study micelle formation in water-soluble block copolymers," Langmuir 1990, 6(2):514-516.
Zhao et al., "Tumor αvβ3 Integrin Is a Therapeutic Target for Breast Cancer Bone Metastases," Cancer Res, AACR Publications, Jun. 2007, 67(12):5821-30.
Zimm, "Apparatus and Methods for Measurement and Interpretation of the Angular Variation of Light Scattering; Preliminary Results on Polystyrene Solutions," J. Chem. Phys. 1948, 16, 1099-1116.
Zini et al., "Contemporary management of adrenocortical carcinoma," European urology, Nov. 2011, 60(5): 1055-1065.
Zong et al., "Crystal structures of *Staphylococcus aureus* sortase A and its substrate complex," J. Biol. Chem. 279, 2004, 31383-31389.
Zununi Vahed et al., "Targeted cancer drug delivery with aptamer-functionalized polymeric nanoparticles," Journal of drug targeting, Mar. 2019, 27(3):292-299.
International Search Report and Written Opinion for Application No. PCT/US2008/084159 dated Feb. 27, 2009 (8 pages).
International Search Report and Written Opinion for Application No. PCT/US2016/024202 dated Aug. 26, 2016 (9 pages).
International Search Report and Written Opinion for Application No. PCT/US2016/045655 dated Dec. 2, 2016 (13 pages).
International Search Report and Written Opinion for Application No. PCT/US2016/068141 dated Jul. 19, 2017 (12 pages).
International Search Report and Written Opinion for Application No. PCT/US2016/068142 dated Jul. 19, 2017 (12 pages).
International Search Report and Written Opinion for Application No. PCT/US2018/032785 dated Sep. 25, 2018 (16 pages).
International Search Report and Written Opinion for Application No. PCT/US2017/035530 dated Aug. 23, 2017 (13 pages).
International Search Report and Written Opinion for Application No. PCT/US2017/052887 dated Jan. 26, 2018 (20 pages).
International Search Report and Written Opinion for Application No. PCT/US2017/051661 dated Jan. 2, 2018 (12 pages).
International Search Report and Written Opinion for Application No. PCT/US2018/013611 dated May 30, 2018 (18 pages).
International Search Report and Written Opinion for Application No. PCT/US2018/040409 dated Nov. 5, 2018 (16 pages).
International Search Report and Written Opinion for Application No. PCT/US2019/015176 dated Jun. 3, 2019 (12 pages).
International Search Report and Written Opinion for Application No. PCT/US2019/023583 dated Jul. 5, 2019 (10 pages).
International Search Report and Written Opinion for Application No. PCT/US2019/030022 dated Jul. 25, 2019 (8 pages).
International Search Report and Written Opinion for Application No. PCT/US2019/044911 dated Dec. 10, 2019 (11 pages).
International Search Report and Written Opinion for Application No. PCT/US2019/050077 dated Jan. 27, 2020 (19 pages).
International Search Report and Written Opinion for Application No. PCT/US2019/061144 dated May 21, 2020 (15 pages).
United States Patent Office Action for U.S. Appl. No. 13/904,836 dated Mar. 27, 2014 (10 pages).
United States Patent Office Notice of Allowance for U.S. Appl. No. 13/904,836 dated Jul. 30, 2014 (6 pages).
United States Patent Office Action for U.S. Appl. No. 13/942,037 dated Jan. 15, 2016 (19 pages).
United States Patent Office Action for U.S. Appl. No. 13/942,037 dated Jun. 4, 2015 (33 pages).
United States Patent Office Action for U.S. Appl. No. 13/942,037 dated Nov. 28, 2016 (22 pages).
United States Patent Office Action for U.S. Appl. No. 13/942,037 dated Feb. 9, 2018 (29 pages).
United States Patent Office Notice of Allowance for U.S. Appl. No. 13/245,459 dated Feb. 27, 2013 (13 pages).

(56) References Cited

OTHER PUBLICATIONS

United States Patent Office Action for U.S. Appl. No. 14/572,391 dated Oct. 26, 2016 (11 pages).
United States Patent Office Notice of Allowance for U.S. Appl. No. 14/572,391 dated Jun. 16, 2017 (10 pages).
United States Patent Office Action for U.S. Appl. No. 15/387,536 dated Sep. 27, 2018 (11 pages).
United States Patent Office Action for U.S. Appl. No. 15/387,540 dated Sep. 27, 2018 (12 pages).
United States Patent Office Action for U.S. Appl. No. 15/561,799 dated Dec. 27, 2018 (8 pages).
United States Patent Office Notice of Allowance for U.S. Appl. No. 15/387,536 dated Mar. 13, 2019 (13 pages).
United States Patent Office Notice of Allowance for U.S. Appl. No. 15/561,799 dated Apr. 2, 2019 (6 pages).
United States Patent Office Notice of Allowance for U.S. Appl. No. 15/387,540 dated Apr. 17, 2019 (9 pages).
United States Patent Office Action for U.S. Appl. No. 16/058,924 dated Nov. 26, 2019 (23 pages).
United States Patent Office Action for U.S. Appl. No. 16/064,424 dated Apr. 22, 2020 (18 pages).
United States Patent Office Action for U.S. Appl. No. 16/064,425 dated Apr. 22, 2020 (18 pages).
United States Patent Office Action for U.S. Appl. No. 16/058,924 dated Jul. 6, 2020 (51 pages).
United States Patent Office Action for U.S. Appl. No. 15/749,797 dated May 11, 2020 (14 pages).
United States Patent Office Action for U.S. Appl. No. 15/749,797 dated Oct. 20, 2020 (16 pages).
Ozer et al., "Injectable non-immunogenic PEG-like conjugate that forms a subcutaneous depot and enables sustained delivery of a peptide drug," Research Square, 2021, 38 pages.
Hu et al., "Site-specific in situ growth of a cyclized protein-polymer conjugate with improved stability and tumor retention," Biomaterials, 2015, 47:13-19.
International Search Report and Written Opinion for Application No. PCT/US2022/041241 dated Oct. 25, 2022 (10 pages).
United States Patent Office Action for Application No. 17/265, 165 dated Sep. 2, 2022 (5 pages).
United States Patent Office Action for U.S. Appl. No. 17/015,315 dated Dec. 23, 2022 (10 pages).
United States Patent Office Notice of Allowance for U.S. Appl. No. 16/477,229 dated Jan. 6, 2023 (8 pages).
United States Patent Office Notice of Allowance for U.S. Appl. No. 17/265,165 dated Jan. 10, 2023 (7 pages).
United States Patent Office Notice of Allowance for U.S. Appl. No. 16/625,899 dated Jan. 18, 2023 (8 pages).
Ahmed et al., "Preliminary Identification of Potential Vaccine Targets for the COVID-19 Coronavirus (SARS-CoV-2) Based on SARS-CoV Immunological Studies," Viruses, 2020, 12:254, 15 pages.
Amanat et al., "A serological assay to detect SARS-CoV-2 seroconversion in humans," Nat Med, 2020, 26(7): 1033-1036.
American Hospital Association, "AHA Hospital Statistics," 2020 edition. Available at: <https://www.aha.org/statistics/fast-facts-us-hospitals>.
Armbruster et al., "Limit of blank, limit of detection and limit of quantitation," Clin Biochem Rev, 2008, 29 Suppl 1: S49-52.
Arshavsky-Graham et al., "Lab-on-a-Chip Devices for Point-of-Care Medical Diagnostics," Advances in Biochemical Engineering/Biotechnology, 2020, 19 pages.
Atyeo et al., "Distinct Early Serological Signatures Track with SARS-CoV-2 Survival," Immunity, 2020, 53: 524-532.
Baraf et al., "Infusion-related reactions with pegloticase, a recombinant uricase for the treatment of chronic gout refractory to conventional therapy," J Clin Rheumatol, 2014, 20: 427-432.
Benn et al., "Physiology of Hyperuricemia and Urate-Lowering Treatments," Front Med (Lausanne), 2018, 5: 160, 28 pages.
Berry et al., "Development and characterisation of neutralising monoclonal antibody to the SARS-coronavirus," J Virol Methods, 2004, 120: 87-96.
Bryant et al., "Serology for SARS-CoV-2: Apprehensions, opportunities, and the path forward," Sci Immunol, 2020, 5: eabc6347, 4 pages.
Calabrese et al., "Frequency, distribution and immunologic nature of infusion reactions in subjects receiving pegloticase for chronic refractory gout," Arthritis Res Ther, 2017, 19: 191, 7 pages.
Caves et al., "Thermal inactivation of uricase (urate oxidase): mechanism and effects of additives," Biochemistry, 2013, 52: 497-507.
Chae et al., "Pharmacokinetic and pharmacodynamic evaluation of site-specific PEGylated glucagon-like peptide-1 analogs as flexible postprandial-glucose controllers," J Pharm Sci, 2009, 98(4): 1556-1567.
Chen et al., "Real-world patterns of pegloticase use for treatment of gout: descriptive multidatabase cohort study," BMJ Open, 2020, 10: e041167, 6 pages.
Chen et al., "The influence of polymer topology on pharmacokinetics: differences between cyclic and linear PEGylated poly(acrylic acid) comb polymers," J Control Release, 2009, 140: 203-209.
Chu et al., "Molecular Diagnosis of a Novel Coronavirus (2019-nCoV) Causing an Outbreak of Pneumonia," Clin Chem, 2020, 66(4): 549-555.
Cong et al., "Nucleocapsid Protein Recruitment to Replication-Transcription Complexes Plays a Crucial Role in Coronaviral Life Cycle," J Virol, 2020, 94: e01925-19, 21 pages.
Crowther, "The ELISA guidebook," Methods Mol Biol, 2000, 149(III-IV): 1-413.
Dincer et al., "Multiplexed Point-of-Care Testing—xPOCT," Trends Biotechnol, 2017, 35(8): 728-742.
Dong et al., "An interactive web-based dashboard to track COVID-19 in real time," Lancet Infect Dis, 2020, 20: 533-534.
Dutta et al., "The Nucleocapsid Protein of SARS-CoV-2: a Target for Vaccine Development," J Virol, 2020, 94(13): e00647-20, 2 pages.
Ekladious et al., "Polymer-drug conjugate therapeutics: advances, insights and prospects," Nature Reviews Drug Discovery, 2019, 18: 273-294.
Fathallah et al., "Immunogenicity of Subcutaneously Administered Therapeutic Proteins—a Mechanistic Perspective," The AAPS Journal, 2013, 15(4): 897-900.
Fox et al., "Soluble polymer carriers for the treatment of cancer: the importance of molecular architecture," Acc Chem Res, 2009, 42(8): 1141-1151.
Garay et al., "Therapeutic perspectives on uricases for gout," Joint Bone Spine, 2012, 79: 237-242.
Harris et al., "Effect of pegylation on pharmaceuticals," Nature Reviews Drug Discovery, 2003, 2: 214-221.
Heggestad et al., "In Pursuit of Zero 2.0: Recent Developments in Nonfouling Polymer Brushes for Immunoassays," Adv Mater, 2020, 32: e1903285.
Hermanson et al., "Peginesatide for the treatment of anemia due to chronic kidney disease—an unfulfilled promise," Expert Opin Drug Saf, 2016, 15(10): 1421-1426.
Hershfield et al., "Treating gout with pegloticase, a PEGylated urate oxidase, provides insight into the importance of uric acid as an antioxidant in vivo," Proc Natl Acad Sci U S A, 2010, 107(32): 14351-14356.
Huang et al., "Clinical features of patients infected with 2019 novel coronavirus in Wuhan," China. Lancet, 2020, 395: 497-506.
Hucknall et al., "Simple Fabrication of Antibody Microarrays on Nonfouling Polymer Brushes with Femtomolar Sensitivity for Protein Analytes in Serum and Blood," Adv Mater, 2009, 21(19): 1968-1971.
Jiang et al., "Neutralizing Antibodies against SARS-CoV-2 and Other Human Coronaviruses," Trends Immunol, 2020, 41(5): 355-359.
Joh et al., "Architectural Modification of Conformal PEG-Bottlebrush Coatings Minimizes Anti-PEG Antigenicity While Preserving Stealth Properties," Advanced Healthcare Materials, 2019, 8(8): 1801177, 27 pages.

(56) References Cited

OTHER PUBLICATIONS

Joh et al., "Inkjet-printed point-of-care immunoassay on a nanoscale polymer brush enables subpicomolar detection of analytes in blood," Proc Natl Acad Sci U S A, 2017, 114: E7054-E7062.

Kang et al., "Crystal structure of SARS-CoV-2 nucleocapsid protein RNA binding domain reveals potential unique drug targeting sites," Acta Pharm Sin B, 2020, 10(7): 1228-1238.

Khailany et al., "Genomic characterization of a novel SARS-CoV-2," Gene Rep, 2020, 9: 100682, 6 pages.

Kozel et al., "Point-of-care testing for infectious diseases: past, present, and future," J Clin Microbiol, 2017, 55: 2313-2320.

Kozma et al., "Anti-PEG antibodies: Properties, formation, testing and role in adverse immune reactions to PEGylated nano-biopharmaceuticals," Adv Drug Deliv Rev, 2020, 154-155, 163-175.

Krammer et al., "Serology assays to manage COVID-19," Science, 2020, 368: 1060-1061.

Kuo et al., "Global epidemiology of gout: prevalence, incidence and risk factors," Nature Reviews Rheumatology, 2015, 11: 649-662.

Laing et al., "A dynamic COVID-19 immune signature includes associations with poor prognosis," Nat Med, 2020, 26:1623-1635.

Lieberman et al., "Comparison of Commercially Available and Laboratory-Developed Assays for In Vitro Detection of SARS-CoV-2 in Clinical Laboratories," J Clin Microbiol, 2020, 58(8):e00821-20.

Lipsitch et al., "Antibody testing will enhance the power and accuracy of COVID-19-prevention trials," Nat Med, 2020, 26: 818-819.

Lipsky et al., "Pegloticase immunogenicity: the relationship between efficacy and antibody development in patients treated for refractory chronic gout," Arthritis Res Ther, 2014, 16: R60.

Lisboa Bastos et al., "Diagnostic accuracy of serological tests for covid-19: systematic review and meta-analysis," BMJ, 2020, 370: m2516.

Liu et al., "High neutralizing antibody titer in intensive care unit patients with COVID-19," Emerg Microbes Infect, 2020, 9: 1664-1670.

Liu et al., "Semi-permeable coatings fabricated from comb-polymers efficiently protect proteins in vivo," Nature Communications, 2014, 5: 5526.

Liu et al., "The experiences of health-care providers during the COVID-19 crisis in China: a qualitative study," Lancet Glob Health, 2020, 8: e790-e798.

Lu et al., "Genomic characterisation and epidemiology of 2019 novel coronavirus: implications for virus origins and receptor binding," Lancet, 2020, 395: 565-574.

McAndrews et al., "Heterogeneous antibodies against SARS-CoV-2 spike receptor binding domain and nucleocapsid with implications for COVID-19 immunity," JCI Insight, 2020, 5(18):e142386, 14 pages.

McElvaney et al., "A linear prognostic score based on the ratio of interleukin-6 to interleukin-10 predicts outcomes in COVID-19," EBioMedicine, 2020, 61: 103026, 8 pages.

Mejía-Salazar et al., "Microfluidic Point-of-Care Devices: New Trends and Future Prospects for eHealth Diagnostics," Sensors, 2020, 20: 1951, 19 pages.

Miller et al., "Disease and healthcare burden of COVID-19 in the United States," Nat Med, 2020, 26: 1212-1217.

Nalla et al., "Comparative Performance of SARS-CoV-2 Detection Assays Using Seven Different Primer-Probe Sets and One Assay Kit," J Clin Microbiol, 2020, 58: e00557-20, 6 pages.

Norman et al., "Ultrasensitive high-resolution profiling of early seroconversion in patients with COVID-19," Nat Biomed Eng, 2020, 11 pages.

Nunn et al., "Crystal Structure of Tobacco Etch Virus Protease Shows the Protein C Terminus Bound within the Active Site," Journal of Molecular Biology, 2005, 350: 145-155.

Nyborg et al., "A Therapeutic Uricase with Reduced Immunogenicity Risk and Improved Development Properties," PLoS One, 2016, 11(12): e0167935, 23 pages.

Okba et al., "Severe Acute Respiratory Syndrome Coronavirus 2-Specific Antibody Responses in Coronavirus Disease Patients," Emerg Infect Dis, 2020, 26: 1478-1488.

Ozer et al., "Effect of Molecular Architecture on Cell Interactions and Stealth Properties of PEG," Biomacromolecules, 2017, 18: 2699-2710.

Pecoraro et al., "A systematic evaluation of immunoassay point-of-care testing to define impact on patients' outcomes," Ann Clin Biochem, 2017, 54(4): 420-431.

Ponti et al., "Biomarkers associated with COVID-19 disease progression," Crit Rev Clin Lab Sci, 2020, 57, 11 pages.

Posthuma-Trumpie et al., "Lateral flow (immuno)assay: its strengths, weaknesses, opportunities and threats. A literature survey," Anal Bioanal Chem, 2009, 393: 569-582.

Radzicka et al., "Comparing the Polrities of the Amino Acids: Side-Chain Distribution Coefficients between the Vapor Phase, Cyclohexane, 1-Octanol, and Neutral Aqueous Solution," Biochemistry, 1988, 27: 1664-1670.

Ravichandran et al., "Antibody signature induced by SARS-CoV-2 spike protein immunogens in rabbits," Sci Transl Med, 2020, 10.1126/scitranslmed.abc3539, 9 pages.

Rogers et al., "Isolation of potent SARS-CoV-2 neutralizing antibodies and protection from disease in a small animal model," Science, 2020, 369: 956-963.

Rosadas et al., "Testing for responses to the wrong SARS-CoV-2 antigen," Lancet, 2020, 396: e23.

Rothe et al., "Transmission of 2019-nCoV Infection from an Asymptomatic Contact in Germany," N Engl J Med, 2020, 382: 10, 2 pages.

Seow et al., "Longitudinal evaluation and decline of antibody responses in SARS-CoV-2 infection," medRxiv, 2020, 24 pages.

Sundy et al., "Efficacy and tolerability of pegloticase for the treatment of chronic gout in patients refractory to conventional treatment: two randomized controlled trials," Jama, 2011, 306(7): 711-720.

Sundy et al., "Pharmacokinetics and pharmacodynamics of intravenous PEGylated recombinant mammalian urate oxidase in patients with refractory gout," Arthritis Rheum, 2007, 56(3): 1021-1028.

Tang et al., "Laboratory Diagnosis of COVID-19: Current Issues and Challenges," J Clin Microbiol, 2020, 58: e00512-20, 9 pages.

Turner et al., "Challenges and Opportunities for the Subcutaneous Delivery of Therapeutic Proteins," Journal of Pharmaceutical Sciences, 2018, 107(5): 1247-1260.

U.S. FDA—Classify your medical devices. Updated as of: Feb. 7, 2020. Available at: <https://www.fda.gov/medical-devices/overview-device-regulation/classify-your-medical-device>.

U.S. FDA—In Vitro Diagnostics. Updated as of: Oct. 25, 2019. Available at: <https://www.fda.gov/medical-devices/products-and-medical-procedures/vitro-diagnostics>.

Vaninov, "In the eye of the COVID-19 cytokine storm," Nat Rev Immunol, 2020, 20: 277, 1 page.

Vashist et al., "Emerging Technologies for Next-Generation Point-of-Care Testing," Trends Biotechnol, 2015, 33(11): 692-705.

Verhoef et al., "Potential induction of anti-PEG antibodies and complement activation toward PEGylated therapeutics," Drug Discov Today, 2014, 19(12): 1945-1952.

Vugmeyster et al., "Pharmacokinetics and toxicology of therapeutic proteins: Advances and challenges," World J Biol Chem, 2012, 3(4): 73-92.

Waterboer et al., "Suppression of non-specific binding in serological Luminex assays," J Immunol Methods, 2006, 309: 200-204.

Weinhandl et al., "Relative safety of peginesatide and epoetin alfa," Pharmacoepidemiology and Drug Safety, 2014, 23(10): 1003-1011.

Whitman et al., "Evaluation of SARS-CoV-2 serology assays reveals a range of test performance," Nat Biotechnol, 2020, 38: 1174-1183.

Wiersinga et al., "Pathophysiology, Transmission, Diagnosis, and Treatment of Coronavirus Disease 2019 (COVID-19): A Review," JAMA, 2020, 324(8): 782-793.

Winter et al., "The important role of serology for COVID-19 control," Lancet Infect Dis, 2020, 20: 758-759.

Wölfel et al., "Virological assessment of hospitalized patients with COVID-2019," Nature, 2020, 581: 465-469.

(56) References Cited

OTHER PUBLICATIONS

Yang et al., "Analysis of Pre-existing IgG and IgM Antibodies against Polyethylene Glycol (PEG) in the General Population," Analytical Chemistry, 2016, 88(23): 11804-11812.
Yang et al., "Anti-PEG immunity: emergence, characteristics, and unaddressed questions," Wiley Interdiscip Rev Nanomed Nanobiotechnol, 2015, 7(5): 655-677.
Yang et al., "Plasma IP-10 and MCP-3 levels are highly associated with disease severity and predict the progression of COVID-19," J Allergy Clin Immunol, 2020, 146: 119-127.
Yang et al., "Uricases as therapeutic agents to treat refractory gout: Current states and future directions," Drug Dev Res, 2012, 73(2): 66-72.
Yong et al., "Connecting clusters of COVID-19: an epidemiological and serological investigation," Lancet Infect Dis, 2020, 20: 809-815.
Zhang et al., "Anti-PEG antibodies in the clinic: Current issues and beyond PEGylation," J Control Release, 2016, 244(Pt B): 184-193.
Zhang et al., "Impact of Large Aggregated Uricases and PEG Diol on Accelerated Blood Clearance of PEGylated Canine Uricase," PLoS ONE, 2012, 7(6): e39659.
Zhao et al., "Antibody responses to SARS-CoV-2 in patients of novel coronavirus disease 2019," Clin Infect Dis, 2020, 22 pages.
International Search Report and Written Opinion for Application No. PCT/US2021/020591 dated Oct. 7, 2021 (14 pages).
United States Patent Office Action for U.S. Appl. No. 16/614,282 dated Oct. 21, 2021 (14 pages).
United States Patent Office Action for U.S. Appl. No. 15/749,797 dated Nov. 29, 2021 (10 pages).
United States Patent Office Action for U.S. Appl. No. 16/477,229 dated Oct. 26, 2021 (10 pages).
Erbacher et al., "Transfection and Physical Properties of Various Saccharide, Poly(ethylene glycol), and Antibody-Derivatized Polyethylenimines (PEI)," The Journal of Gene Medicine, 1999, 1: 210-222.
International Search Report and Written Opinion for Application No. PCT/US2022/078659 dated Feb. 1, 2023 (17 pages).
United States Patent Office Action for U.S. Appl. No. 16/964,832 dated Apr. 17, 2023 (17 pages).
U.S. Appl. No. 13/245,459, filed Sep. 26, 2011, now U.S. Pat. No. 8,470,967, Jun. 25, 2013.
U.S. Appl. No. 13/904,836, filed May 29, 2013, now U.S. Pat. No. 8,912,310, Dec. 16, 2014.
U.S. Appl. No. 14/572,391, filed Dec. 16, 2014, now U.S. Pat. No. 9,771,396, Jun. 25, 2013.
U.S. Appl. No. 15/679,751, filed Aug. 17, 2017, 2018/0037609, Feb. 8, 2018.
U.S. Appl. No. 62/138,847, filed Mar. 26, 2015.
PCT/US2016/024202, Mar. 25, 2016, WO2016/154530, Sep. 26, 2016.
U.S. Appl. No. 15/561,799, filed Sep. 26, 2017, now U.S. Pat. No. 10,385,115, Aug. 20, 2019.
U.S. Appl. No. 16/525,374, filed Jul. 29, 2019, 2019/0345228, Nov. 14, 2019.
U.S. Appl. No. 62/399,123, filed Sep. 23, 2016.
PCT/US2017/052887, Sep. 22, 2017, WO2018/057847, Mar. 29, 2018.
U.S. Appl. No. 16/335,734, filed Mar. 22, 2019, 2020/0017557, Jan. 16, 2020.
U.S. Appl. No. 13/942,037, filed Jul. 15, 2015, 2014/0024600, Jan. 23, 2014.
U.S. Appl. No. 16/058,924, filed Aug. 8, 2018, 2019/0023743, Jan. 24, 2019.
U.S. Appl. No. 62/270,401, filed Dec. 21, 2015.
U.S. Appl. No. 62/310,534, filed Mar. 18, 2016.
U.S. Appl. No. 62/329,800, filed Apr. 29, 2016.
U.S. Appl. No. 62/407,403, filed Oct. 12, 2016.
PCT/US2016/068141, Dec. 21, 2016, WO2017/112825, Jun. 29, 2017.
PCT/US2016/068142, Dec. 21, 2016, WO2017/112826, Jun. 29, 2017.
U.S. Appl. No. 15/387,536, filed Dec. 21, 2016, now U.S. Pat. No. 10,364,451, Jul. 30, 2019.
U.S. Appl. No. 15/387,540, filed Dec. 21, 2016, now U.S. Pat. No. 10,392,611, Aug. 27, 2019.
U.S. Appl. No. 16/064,424, filed Jun. 20, 2018, 2019/0015520, Jan. 17, 2019.
U.S. Appl. No. 16/064,425, filed Sep. 12, 2016, 2018/0369399, Dec. 27, 2018.
U.S. Appl. No. 62/506,593, filed May 15, 2017.
U.S. Appl. No. 62/534,442, filed Jul. 19, 2017.
U.S. Appl. No. 62/544,720, filed Aug. 11, 2017.
U.S. Appl. No. 62/545,313, filed Aug. 14, 2017.
PCT/US20168/032785, May 15, 2018, WO2018/213320, Nov. 22, 2018.
U.S. Appl. No. 16/614,282, filed Nov. 15, 2019.
U.S. Appl. No. 62/200,726, filed Aug. 4, 2015.
PCT/US2016/045655, Aug. 4, 2016, WO2017/024182, Feb. 9, 2017.
U.S. Appl. No. 15/749,797, filed Feb. 2, 2018, 2018/0228908, Aug. 16, 2018.
U.S. Appl. No. 62/394,662, filed Sep. 14, 2016.
PCT/US2017/051661, Sep. 14, 2017, WO2018/053201, Mar. 22, 2018.
U.S. Appl. No. 16/332,865, filed Mar. 13, 2019, 2020/0164082, May 28, 2020.
U.S. Appl. No. 62/445,504, filed Jan. 12, 2017.
U.S. Appl. No. 62/479,977, filed Mar. 31, 2017.
PCT/US2018/013611, Jan. 12, 2018, WO2018/132732, Jul. 19, 2018.
U.S. Appl. No. 16/477,229, filed Jul. 11, 2019, 2019/0328662, Oct. 31, 2019.
U.S. Appl. No. 62/527,836, filed Jun. 30, 2017.
U.S. Appl. No. 62/534,019, filed Jul. 18, 2017.
PCT/US2018/040409, Jun. 29, 2018, WO2019/006374, Jan. 3, 2019.
U.S. Appl. No. 16/625,899, filed Dec. 23, 2019, 2020/0148724, May 14, 2020.
U.S. Appl. No. 62/343,926, filed Jun. 1, 2016.
U.S. Appl. No. 62/414,877, filed Oct. 31, 2016.
PCT/US2017/035530, Jun. 1, 2017, WO2017/210476, Dec. 7, 2018.
U.S. Appl. No. 16/305,696, filed Nov. 29, 2018.
U.S. Appl. No. 62/728,582, filed Sep. 7, 2018.
PCT/US2019/050077, Sep. 6, 2019, WO2020/051541, Mar. 12, 2020.
U.S. Appl. No. 62/767,736, filed Nov. 15, 2018.
PCT/US2019/061144, Nov. 13, 2019, WO2020/102324, May 22, 2020.
U.S. Appl. No. 62/622,249, filed Jan. 26, 2018.
PCT/US2019/015176, Jan. 25, 2019, WO2019/147954, Aug. 1, 2019.
U.S. Appl. No. 16/964,832, filed Jul. 24, 2020.
U.S. Appl. No. 62/647,199, filed Mar. 23, 2018.
PCT/US2019/023583, Mar. 22, 2019, WO2019/183476, Sep. 26, 2019.
U.S. Appl. No. 62/700,939, filed Jul. 20, 2018.
U.S. Appl. No. 62/873,306, filed Jul. 12, 2019.
U.S. Appl. No. 16/927,982, filed Jul. 13, 2020.
U.S. Appl. No. 62/713,752, filed Aug. 2, 2018.
PCT/US2019/044911, Aug. 2, 2019, WO2020/028806, Feb. 6, 2020.
U.S. Appl. No. 62/985,174, filed Mar. 4, 2020.
U.S. Appl. No. 62/985,179, filed Mar. 4, 2020.
U.S. Appl. No. 62/898,353, filed Sep. 12, 2019.
U.S. Appl. No. 17/015,315, filed Sep. 9, 2020.
Chan et al., "A randomized, repeat-dose, pharmacodynamic and safety study of an antidote-controlled factor IXa inhibitor," J Thromb Haemost, 2008, 6(5): 789-796.
Chan et al., "Phase 1b randomized study of antidote-controlled modulation of factor IXa activity in patients with stable coronary artery disease," Circulation, 2008, 117(22): 2865-2874.

(56) References Cited

OTHER PUBLICATIONS

Chappell et al., "Computational design of small transcription activating RNAs for versatile and dynamic gene regulation," Nat Commun, 2017, 8(1): 1051.
Chappell et al., "Creating small transcription activating RNAs," Nat Chem Biol, 2015, 11(3): 214-220.
Chase et al., "Single-Stranded DNA Binding Proteins Required for DNA Replication," Ann. Rev. Biochem., 1986, 55: 103-136.
Cohen et al., "First clinical application of an actively reversible direct factor IXa inhibitor as an anticoagulation strategy in patients undergoing percutaneous coronary intervention," Circulation, 2010, 122(6): 614-622.
Dale et al., "Direct covalent mercuration of nucleotides and polynucleotides," Biochemistry, 1975, 14(11): 2447-2457.
Davis et al., "Antibodies and the RNA World: A Role for Low-molecular-weight Effectors in Biochemical Evolution," RNA World, 1993, Chapter 8, p. 185-204.
Dyke et al., "First-in-human experience of an antidote-controlled anticoagulant using RNA aptamer technology: a phase 1a pharmacodynamic evaluation of a drug-antidote pair for the controlled regulation of factor IXa activity," Circulation, 2006, 114(23): 2490-2497.
Eichhorn et al., "Interactions of metal ions with polynucleotides and related compounds. XII. The relative effect of various metal ions on DNA helicity," J. Am. Chem. Soc, 1968, 90: 7323-7328.
Ganesan et al., "Lipid Nanoparticles: Different Preparation Techniques, Characterization, Hurdles, and Strategies for the Production of Solid Lipid Nanoparticles and Nanostructured Lipid Carriers for Oral Drug Delivery," Sustain. Chem. Pharm., 2017, 6: 37-56.
Gold et al., "Aptamers and the RNA World, Past and Present," Cold Spring Harbor Perspect. Biol., 2012, 4: a003582, 9 pages.
Heus, "RNA aptamers," Nat Struct Biol, 1997, 4(8): 597-600.
Hucknall et al., "Simple Fabrication of Antibody Microarrays on Nonfouling Polymer Brushes with Femtomolar Sensitivity for Protein Analytes in Serum and Blood," Adv Mater, 2009, 21: 1968-1971.
Hwang et al., "Inhibition of gene expression in human cells through small molecule-RNA interactions," Proc. Natl. Acad. Sci. USA, 1999, 96(23): 12997-13002.
Keefe et al., "Aptamers as therapeutics," Nature Reviews Drug Discovery, 2010, 9: 537-550.
Korte et al., "Short activated partial thromboplastin times are related to increased thrombin generation and an increased risk for thromboembolism," Am J Clin Pathol, 2000, 113(1): 123-127.
Li et al., "Ferric Chloride-induced Murine Thrombosis Models," J. Vis. Exp., 2016, 115: e54479, 12 pages.
Lincoff et al., "Effect of the REG1 anticoagulation system versus bivalirudin on outcomes after percutaneous coronary intervention (REGULATE-PCI): a randomised clinical trial," Lancet, 2016, 387(10016): 349-356.
Lippard et al., "Platinum complexes: probes of polynucleotide structure and antitumor drugs," Acc. Chem. Res., 1978, 11(5): 211-217.
Maier et al., "From selection hits to clinical leads: progress in aptamer discovery," Mol. Ther. Methods Clin. Dev., 2016, 3: 16014, 10 pages.
McManus et al., "Gene silencing in mammals by small interfering RNAs," Nat Rev Genet, 2002, 3(10): 737-747.
Moreno et al., "Anti-PEG Antibodies Inhibit the Anticoagulant Activity of PEGylated Aptamers," Cell Chem Biol, 2019, 26(5): 634-644.e3.
Nimjee et al., "Aptamers as Therapeutics," Annu Rev Pharmacol Toxicol, 2017, 57: 61-79.
Pisal et al., "Delivery of therapeutic proteins," Journal of Pharmaceutical Sciences, 2010, 99(6): 2557-2575.
Povsic et al., "A Phase 2, randomized, partially blinded, active-controlled study assessing the efficacy and safety of variable anticoagulation reversal using the REG1 system in patients with acute coronary syndromes: results of the RADAR trial," Eur Heart J, 2013, 34(31): 2481-2489.
Povsic et al., "Pre-existing anti-PEG antibodies are associated with severe immediate allergic reactions to pegnivacogin, a PEGylated aptamer," J Allergy Clin Immunol, 2016, 138(6): 1712-1715.
Purtell et al., "Isoelectric point of albumin: effect on renal handling of albumin," Kidney Int, 1979, 16(3): 366-376.
Richter et al., "Mechanistic determinants of biotherapeutics absorption following SC administration," AAPS J, 2012, 14(3): 559-570.
Rinaldi et al., "Antisense oligonucleotides: the next frontier for treatment of neurological disorders," Nat Rev Neurol, 2018, 14(1): 9-21.
Rusconi et al., "Antidote-mediated control of an anticoagulant aptamer in vivo," Nat Biotechnol, 2004, 22(11): 1423-1428.
Rusconi et al., "RNA aptamers as reversible antagonists of coagulation factor Ixa," Nature, 2002, 19(6902): 90-94.
Shu et al., "GISAID: Global initiative on sharing all influenza data—from vision to reality," Euro Surveill 22, 2017, 22(13): 30494, 3 pages.
Smith et al., "Coronaviruses lacking exoribonuclease activity are susceptible to lethal mutagenesis: evidence for proofreading and potential therapeutics," PLoS Pathog, 2013, 9: e1003565, 11 pages.
Tuerk et al., "Systematic evolution of ligands by exponential enrichment: RNA ligands to bacteriophage T4 DNA polymerase," Science, 1990, 249(4968): 505-510.
Werstuck et al., "Controlling gene expression in living cells through small molecule-RNA interactions," Science, 1998, 282(5387): 296-298.
Woodruff et al., "Modulation of the Coagulation Cascade Using Aptamers," Arterioscler Thromb Vasc Biol, 2015, 35(10): 2083-2091.
Yamaoka et al., "Distribution and tissue uptake of poly(ethylene glycol) with different molecular weights after intravenous administration to mice," Journal of Pharmaceutical Sciences, 1994, 83(4): 601-606.
Yizhi et al., "A brush-polymer/exendin-4 conjugate reduces blood glucose levels for up to five days and eliminates poly(ethylene glycol) antigenicity," Nature Biomedical Engineering, 2016, 1(1): 0002.
Zhou et al., "Aptamers as targeted therapeutics: current potential and challenges," Nat Rev Drug Discov, 2017, 16(3): 181-202.
Gilroy et al., "Sustained release of a GLP-1 and FGF21 dual agonist from an injectable depot protects mice from obesity and hyperglycemia," Science Advances, 2020, 6(35): eaaz9890, 12 pages.
United States Patent Office Notice of Allowance for U.S. Appl. No. 15/749,797 dated Mar. 16, 2022 (6 pages).
United States Patent Office Action for U.S. Appl. No. 16/477,229 dated Mar. 3, 2022 (10 pages).
European Patent Office Extended Search Report for Application No. 19796027.1 dated Mar. 15, 2022 (10 pages).
Alghoul et al., "The effect of hyaluronan hydrogel on fat graft survival," Aesthet Surg J, 2012, 32: 622-633.
American Society of Plastic Surgeons, "2017 Plastic Surgery Statistics Report," Oct. 2018, 25 pages.
Balaji, "Subdermal fat grafting for Parry-Romberg syndrome," Ann Maxillofac Surg, 2014, 4: 55-59.
Banyard et al., "Preparation, Characterization, and Clinical Implications of Human Decellularized Adipose Tissue Extracellular Matrix (hDAM): A Comprehensive Review," Aesthet Surg J, 2016, 36: 349-357.
Bennett et al., "Association of Fat Grafting With Patient-Reported Outcomes in Postmastectomy Breast Reconstruction," JAMA Surg, 2017, 152: 944-950.
Brzezienski et al., "Autologous Fat Grafting to the Breast Using REVOLVE System to Reduce Clinical Costs," Ann Plast Surg, 2016, 77: 286-289.
Chang et al., "Thermoprecipitation of Glutathione S-Transferase by Glutathione-Poly(N-isopropylacrylamide) Prepared by RAFT Polymerization," Macromolecular Rapid Communications, Oct. 2010, 31: 1691-1695.
De Leon-Rodriguez et al., "Multifunctional thermoresponsive designer peptide hydrogels," Acta Biomaterialia, 2017, 47: 40-49.
Eom et al., "The number of operations required for completing breast reconstruction," Plast Reconstr Surg Glob Open, 2012, 2: e242.

(56) References Cited

OTHER PUBLICATIONS

Frandsen et al., "Recombinant protein-based polymers for advanced drug delivery," Chem Soc Rev, 2012, 41: 2696-2706.
Gabriel et al., "Fat grafting and breast reconstruction: tips for ensuring predictability," Gland Surg, 2015, 4: 232-243.
Gylbert, "Applanation tonometry for the evaluation of breast compressibility," Scand J Plast Reconstr Surg Hand Surg, 1989, 23: 223-229.
Hess et al., "Graphene Transistors for Multifunctional Polymer Brushes for Biosensing Applications," Applied Materials & Interfaces, 2014, 6: 9705-9710.
Hsu et al., "Fat grafting's past, present, and future: why adipose tissue is emerging as a critical link to the advancement of regenerative medicine," Aesthet Surg J, 2015, 32: 892-899.
Hwang et al., "Synthesis and Characterization of Polystyrene Brushes for Organic Thin Film Transistors," Journal of Nanoscience and Nanotechnology, 2012, 12: 4137-4141.
Kronowitz et al., "Delayed-Immediate Breast Reconstruction," Plastic and Reconstructive Surgery, 2004, 113: 1617-1628.
Minteer et al., "Fat Grafting for Pedal Fat Pad Atrophy in a 2-Year, Prospective, Randomized, Crossover, Single-Center Clinical Trial," Plast Reconstr Surg, 2018, 142: 862e-871e.
Pan et al., "A Pig Model for the Histological Analysis of Adipocytes after Co-injections of Autologous Fat with Fillers," International Journal of Surgery & Surgical Techniques, 2016, 2: 7 pages.
Park et al., "Polymer Brush As a Facile Dielectric Surface Treatment for High-Performance, Stable, Soluble Acene-Based Transistors," Chemistry of Materials, 2010, 22: 5377-5382.
Rasmussen et al., "A Novel Porcine Model for Future Studies of Cell-enriched Fat Grafting," Plast Reconstr Surg Glob Open, 2018, 6: e1735.
Roca et al., "Autologous Fat Grafting for Treatment of Breast Implant Capsular Contracture: A Study in Pigs," Aesthet Surg J, 2014, 34: 769-775.
Sandberg et al., "The Structure of the Elastic Fiber: An Overview," The Journal of Investigative Dermatology, 1982, 79(S1): 128s-132s.
Simonacci et al., "Procedure, applications, and outcomes of autologous fat grafting," Ann Med Surg (Lond), 2017, 20: 49-60.
Strong et al., "The Current State of Fat Grafting: A Review of Harvesting, Processing, and Injection Techniques," Plast Reconstr Surg, 2015, 136: 897-912.
Tamburro et al., "Fractal aspects of elastin supramolecular organization," J Biomol Struct Dyn, 1995, 12: 1161-1172.
Toshima et al., "Three-dimensional architecture of elastin and collagen fiber networks in the human and rat lung," Arch Histol Cytol, 2004, 67: 31-40.
UniProtKB-P15214 (GST_PROMI) acessed online at <https://www.uniprot.org/uniprot/P152146/> on Jun. 8, 2021, 7 pages.
Wang et al., "Pigs Can Be Used as a Large Animal Model for Autologous Fat Grafting," Ophthalmic Plast Reconstr Surg, 2016, 32: 73-74.
Wu et al., "An injectable adipose matrix for soft-tissue reconstruction," Plast Reconstr Surg, 2012, 129: 1247-1257.
United States Patent Office Action for U.S. Appl. No. 15/749,797 dated May 12, 2021 (19 pages).
United States Patent Office Notice of Allowance for U.S. Appl. No. 16/332,865 dated May 17, 2021 (5 pages).
United States Patent Office Notice of Allowance for U.S. Appl. No. 16/335,734 dated Jun. 16, 2021 (9 pages).
United States Patent Office Action for U.S. Appl. No. 16/305,696 dated Jun. 22, 2021 (20 pages).
Da Pieve Chiara et al., "Modification of Thiol Functionalized Aptamers by Conjugation of Synthetic Polymers," Bioconjugate Chemistry, 2009, 1(1): 169-174.
International Search Report and Written Opinion for Application No. PCT2022/023158 dated Jun. 21, 2022 (7 pages).
International Search Report and Written Opinion for Application No. PCT/US2022/017349 dated Jun. 3, 2022 (20 pages).
United States Patent Office Action for U.S. Appl. No. 16/964,832 dated Jul. 14, 2022 (6 pages).
United States Patent Office Notice of Allowance for U.S. Appl. No. 16/927,982 dated Jul. 15, 2022 (8 pages).
United States Patent Office Notice of Allowance for U.S. Appl. No. 16/614,282 dated Aug. 23, 2022 (7 pages).
International Search Report and Written Opinion for Application No. PCT/US2021/046833 dated Nov. 8, 2021 (13 pages).
International Search Report and Written Opinion for Application No. PCT/US2021/035823 dated Dec. 8, 2021 (16 pages).
United States Patent Office Action for U.S. Appl. No. 17/265,165 dated Dec. 21, 2021 (11 pages).
United States Patent Office Action for U.S. Appl. No. 16/964,832 dated Jan. 19, 2022 (12 pages).
United States Patent Office Action for U.S. Appl. No. 16/625,899 dated Dec. 15, 2021 (12 pages).
United States Patent Office Action for U.S. Appl. No. 16/927,982 dated Jan. 6, 2022 (6 pages).
Nikolic et al., "Structural basis for the recognition of LDL-receptor family members by VSV glycoprotein," Nature Communications, 2018, 9: 1029, 12 pages.
International Search Report and Written Opinion for Application No. PCT/US2021/020589 dated Jul. 15, 2021 (21 pages).
International Search Report and Written Opinion for Application No. PCT/US2021/017809 dated Jul. 22, 2021 (20 pages).
Ren et al., "Stimulus-Responsive Polymer Prodrugs," Progress in Chemistry, 2013, 25(5): 10 pages.
United States Patent Office Action for U.S. Appl. No. 16/614,282 dated Apr. 27, 2022 (15 pages).
United States Patent Office Notice of Allowance for U.S. Appl. No. 16/305,696 dated May 23, 2022 (10 pages).
United States Patent Office Notice of Allowance for U.S. Appl. No. 16/305,696 dated Jun. 10, 2022 (4 pages).
United States Patent Office Notice of Allowance for U.S. Appl. No. 15/749,797 dated Jun. 2, 2022 (6 pages).
United States Patent Office Action for U.S. Appl. No. 16/477,229 dated Jun. 13, 2022 (11 pages).
United States Patent Office Action for U.S. Appl. No. 16/335,734 dated Nov. 20, 2020 (15 pages).
United States Patent Office Action for U.S. Appl. No. 16/525,374 dated Dec. 7, 2020 (9 pages).
Abbaspourrad et al., "Controlling release from pH-responsive microcapsules," Langmuir, 2013, 29: 12697-12702.
Abbaspourrad et al., "Polymer microcapsules with programmable active release," J Am Chem Soc, 2013, 135: 7744-7750.
Agarwal et al., "One-step microfluidic generation of pre-hatching embryo-like core-shell microcapsules for miniaturized 3D culture of pluripotent stem cells," Lab Chip, 2013, 13: 4525-4533.
Amiram et al., "Evolution of translation machinery in recoded bacteria enables multi-site incorporation of nonstandard amino acids," Nat Biotechnol, 2015, 33: 1272-1279.
Appleyard et al., "Multiplexed protein quantification with barcoded hydrogel microparticles," Anal Chem, 2011, 83: 193-199.
Bain et al., "Formation of monolayer films by the spontaneous assembly of organic thiols from solution onto gold," Journal of the American Chemical Society, 1989, 111: 321-335.
Boeynaems et al., "Spontaneous driving forces give rise to protein-RNA condensates with coexisting phases and complex material properties," Proc Natl Acad Sci U S A, 2019, 116: 7889-7898.
Cha et al., "Microfluidics-assisted fabrication of gelatin-silica core-shell microgels for injectable tissue constructs," Biomacromolecules, 2014, 15: 283-290.
Chapin et al., "Rapid microRNA profiling on encoded gel microparticles," Angew Chem Int Ed Engl, 2011, 50: 2289-2293.
Chin et al., "Addition of p-azido-I-phenylalanine to the genetic code of *Escherichia coli*," Journal of the American Chemical Society, 2002, 124: 9026-9027.
Choi et al., "Multiplexed detection of mRNA using porosity-tuned hydrogel microparticles," Anal Chem, 2012, 84: 9370-9378.
Choi et al., "Recent advances in engineering microparticles and their nascent utilization in biomedical delivery and diagnostic applications," Lab Chip, 2017, 17: 591-613.
Chu et al., "Controllable monodisperse multiple emulsions," Angew Chem Int Ed Engl, 2007, 46: 8970-8974.

(56) References Cited

OTHER PUBLICATIONS

Costa et al., "Photo-crosslinkable unnatural amino acids enable facile synthesis of thermoresponsive nano- to microgels of intrinsically disordered polypeptides," Adv Mater, 2018, 30(5): 1704878.
Darling et al., "Viscoelastic properties of zonal articular chondrocytes measured by atomic force microscopy," Osteoarthritis Cartilage, 2006, 14: 571-579.
Griffin et al., "Accelerated wound healing by injectable microporous gel scaffolds assembled from annealed building blocks," Nat Mater, 2015, 14: 737-744.
Hutter et al., "Calibration of atomic-force microscope tips," Review of Scientific Instruments, 1993, 64: 1868-1873.
Wang et al., "Differentially degradable janus particles for controlled release applications," Macromol Rapid Commun, 2012, 33: 1178-1183.
Jang et al., "Engineering Globular Protein Vesicles through Tunable Self-Assembly of Recombinant Fusion Proteins," Small, 2017, 13(36): 1700399.
Khademhosseini et al., "Micromolding of photocrosslinkable hyaluronic acid for cell encapsulation and entrapment," J Biomed Mater Res A, 2006, 79: 522-532.
Kim et al., "Generation of core-shell microcapsules with three-dimensional focusing device for efficient formation of cell spheroid," Lab Chip, 2011, 11: 246-252.
Liu, L. et al., "Monodisperse core-shell chitosan microcapsules for pH-responsive burst release of hydrophobic drugs," Soft Matter, 2011, 7: 4821-4827.
Ma et al., "Core-shell hydrogel microcapsules for improved islets encapsulation," Adv Healthc Mater, 2013, 2: 667-672.
Matsunaga et al., "Molding cell beads for rapid construction of macroscopic 3D tissue architecture," Adv Mater, 2011, 23: H90-94.
Oh et al., "The development of microgels/nanogels for drug delivery applications," Progress in Polymer Science, 2008, 33(4): 448-477.
Panda et al., "Stop-flow lithography to generate cell-laden microgel particles," Lab Chip, 2008, 8: 1056-1061.
Paulsen et al., "Optofluidic fabrication for 3D-shaped particles," Nat Commun, 2015, 6: 6976.
Roberts et al., "Injectable tissue integrating networks from recombinant polypeptides with tunable order," Nature Materials, 2018, 17(12): 1154-1163.
Rodriguez-Cabello et al., "Elastin-like polypeptides in drug delivery," Adv Drug Deliv Rev, 2016, 97: 85-100.
Song et al., "Budding-like division of all-aqueous emulsion droplets modulated by networks of protein nanofibrils," Nat Commun, 2018, 9: 2110.
Srinivas et al., "Aptamer-functionalized microgel particles for protein detection," Anal Chem, 2011, 83: 9138-9145.
Tsuda et al., "Monodisperse cell-encapsulating peptide microgel beads for 3D cell culture," Langmuir, 2010, 26: 2645-2649.
Utada et al., "Monodisperse double emulsions generated from a microcapillary device," Science, 2005, 308: 537-541.
Uversky, "Protein intrinsic disorder-based liquid-liquid phase transitions in biological systems: Complex coacervates and membraneless organelles," Adv Colloid Interface Sci, 2017, 239: 97-114.
Volodkin et al., "One-Step Formulation of Protein Microparticles with Tailored Properties: Hard Templating at Soft Conditions," Advanced Functional Materials, 2012, 22: 1914-1922.
Wang et al., "Functional polymeric microparticles engineered from controllable microfluidic emulsions," Acc Chem Res, 2014, 47: 373-384.
Yeh et al., "Micromolding of shape-controlled, harvestable cell-laden hydrogels," Biomaterials, 2006, 27: 5391-5398.
United States Patent Office Action for U.S. Appl. No. 16/305,696 dated Jan. 28, 2021 (15 pages).
United States Patent Office Notice of Allowance for U.S. Appl. No. 16/332,865 dated Apr. 2, 2021 (10 pages).
Resh, "Covalent Lipid Modifications of Proteins," Curr Biol., May 2013, 23(10): R431-R435.
United States Patent Office Action for U.S. Appl. No. 16/477,229 dated Apr. 12, 2021 (14 pages).
United States Patent Office Notice of Allowance for U.S. Appl. No. 17/015,315 dated Apr. 26, 2023 (7 pages).
Chen et al., "Polyethylene Glycol Immunogenicity: Theoretical, Clinical, and Practical Aspects of Anti-Polyethylene Glycol Antibodies," ACS Nano, 2021, 15(9): 14022-14048.
United States Patent Office Action for U.S. Appl. No. 17/294,368 dated Sep. 12, 2024 (11 pages).
Cascarina et al., "Generalizable Compositional Features Influencing the Proteostatic Fates of Polar Low-Complexity Domains," International Journal of Molecular Sciences, 2021, 22(16): 8944.
Cereghetti et al., "Reversible, functional amyloids: towards an understanding of their regulation in yeast and humans," Cell Cycle, 2018, 17(13): 1545-1558.
Krainer et al., "Reentrant liquid condensate phase of proteins is stabilized by hydrophobic and non-ionic interactions," Nature Communications, 2021, 12(1): 1085.
McPherson, "Product purification by reversible phase transition following *Escherichia coli* expression of genes encoding up to 251 repeats of the elastomeric pentapeptide GVGVP," Protein Expression and Purification, 1996, 7: 51-57.
Uversky et al., "Life in Phases: Intra- and Inter-Molecular Phase Transitions in Protein Solutions," Biomolecules, 2019, 9(12): 842.
Antonicelli et al., "Elastin-elastases and inflamm-aging," Curr Top Dev Biol, 2007, 79: 99-155.
Carvalho et al., "Modern Trends for Peripheral Nerve Repair and Regeneration: Beyond the Hollow Nerve Guidance Conduit," Front Bioeng Biotechnol, 2019, 7: 337.
Gu et al., "Construction of tissue engineered nerve grafts and their application in peripheral nerve regeneration," Prog Neurobiol, 2011, 93: 204-230.
Heggestad et al., "Rapid test to assess the escape of SARS-CoV-2 variants of concern," Science Advances, 2021, 7 (49): 1-12.
Jacobs et al., "Fusion to a highly stabble consensus albumin binding domain allows for tunable pharmacokinetics," Protein Engineering, Designs & Selections, 2015, 28(10): 385-393.
Mohammad et al., "Development and validation of a rapid and easy-to-perform point-of-care lateral flow immunoassay (LFIA) for the detection of SARS-CoV-2 spike protein," Frontiers in Immunology, 2023, 14: 1-15.
Parker et al., "Nerve guidance conduit development for primary treatment of peripheral nerve transection injuries: A commercial perspective," Acta Biomater, 2021, 135: 64-86.
Roberts et al., "Complex microparticle architectures from stimuli-responsive intrinsically disordered proteins," Nat Commun, 2020, 11: 1342.
Rosso et al., "Implications of Schwann Cells Biomechanics and Mechanosensitivity for Peripheral Nervous System Physiology and Pathophysiology," Front Mol Neurosci, 2017, 10: 345.
Rosso et al., "Schwann cells and neurite outgrowth from embryonic dorsal root ganglions are highly mechanosensitive," Nanomedicine, 2017, 13: 493-501.
Saffari et al., "Surgical Angiogenesis of Decellularized Nerve Allografts Improves Early Functional Recovery in a Rat Sciatic Nerve Defect Model," Plast Reconstr Surg, 2021, 148: 561-570.
Saffari et al., "The role of vascularization in nerve regeneration of nerve graft," Neural Regen Res, 2020, 15: 1573-1579.
Shakhbazau et al., "Aligned collagen-GAG matrix as a 3D substrate for Schwann cell migration and dendrimer-based gene delivery," J Mater Sci Mater Med, 2014, 25: 1979-1989.
Taskindoust et al., "Recombinant Elastin Biomatrix Improves Autologous Fat Grafting for Soft Tissue Reconstruction," Plastic and Reconstructive Surgery Global Open, 2022, 10(10S): 74-75.
Weber, "Improving Cloning Procedures and Particle Architectures of Elastin-like Polypeptide-based Drug Delivery Vehicles," Master Thesis, Duke University, Nov. 13, 2019, 92 pages.
International Search Report and Written Opinion for Application No. PCT/US2023/082105 dated Apr. 10, 2024 (8 pages).
United States Patent Office Notice of Allowance for Application No. 17/477,192 dated May 9, 2024 (8 pages).
United States Patent Office Action for U.S. Appl. No. 17/272,887 dated Jun. 4, 2024 (12 pages).

(56) References Cited

OTHER PUBLICATIONS

United States Patent Office Action for U.S. Appl. No. 18/303,530 dated Jun. 21, 2024 (14 pages).
United States Patent Office Action for U.S. Appl. No. 16/964,832 dated Jun. 21, 2024 (6 pages).
Singh et al., "Polymeric microneedles for controlled transdermal drug delivery," Journal of Controlled Release, 2019, 315: 97-113.
Vancoillie et al., "Thermoresponsive poly(oligo ethylene glycol acrylates)," Progress in Polymer Science, 2014, 39(6): 1074-1095.
Zhang et al., "A triple thermoresponsive schizophrenic diblock copolymer," Polymer Chemistry, 2013, 4(16): 4322-4325.
International Search Report and Written Opinion for Application No. PCT/US2024/050476 dated Nov. 25, 2024 (18 pages).
United States Patent Office Notice of Allowance for U.S. Appl. No. 16/964,832 dated Jan. 6, 2025 (14 pages).
United States Patent Office Action for U.S. Appl. No. 17/272,887 dated Nov. 21, 2024 (13 pages).

\* cited by examiner

| Group | POEGMA ID | EG2% by NMR | DP | $M_w$ | $M_n$ | Đ($M_w/M_n$) | Rh(nm) | Tt (°C) |
|---|---|---|---|---|---|---|---|---|
| EG3$_{100\%}$ | P1 | 0 | 105 | 24.7 | 22.7 | 1.079 | 3.4 ± 0.6 | 51.6 |
| | P2 | 0 | 194 | 45.3 | 40.3 | 1.123 | 4.6 ± 1.0 | 48.9 |
| | P3 | 0 | 314 | 73.2 | 68.0 | 1.075 | 6.5 ± 1.4 | 46.7 |
| | P4 | 0 | 386 | 90.0 | 84.7 | 1.063 | 6.7 ± 1.3 | 43.9 |
| EG2$_{58\%}$ | P5 | 58.4 | 95 | 19.9 | 18.3 | 1.088 | 3.0 ± 0.5 | 37.8 |
| | P6 | 58.5 | 206 | 42.7 | 39.6 | 1.078 | 3.4 ± 0.4 | 35.8 |
| | P7 | 59.0 | 285 | 59.1 | 53.1 | 1.113 | 4.8 ± 1.2 | 33.8 |
| | P8 | 56.5 | 394 | 82.0 | 71.6 | 1.146 | 5.1 ± 0.4 | 31.7 |
| EG2$_{66\%}$ | P9 | 65.6 | 96 | 19.8 | 18.1 | 1.092 | 2.9 ± 0.3 | 35.2 |
| | P10 | 65.0 | 201 | 41.2 | 38.6 | 1.066 | 3.2 ± 0.4 | 33.6 |
| | P11 | 68.8 | 298 | 60.5 | 55.3 | 1.095 | 3.9 ± 0.3 | 31.8 |
| | P12 | 65.0 | 389 | 79.5 | 69.4 | 1.145 | 5.3 ± 0.7 | 30.6 |
| EG2$_{74\%}$ | P13 | 72.0 | 104 | 21.1 | 19.3 | 1.091 | 3.1 ± 0.4 | 33.7 |
| | P14 | 75.5 | 208 | 41.6 | 38.3 | 1.086 | 3.5 ± 0.3 | 32.0 |
| | P15 | 76.5 | 313 | 62.5 | 55.7 | 1.122 | 4.6 ± 0.8 | 30.3 |
| | P16 | 73.8 | 420 | 84.2 | 72.2 | 1.166 | 5.7 ± 1.1 | 28.7 |
| EG2$_{82\%}$ | P17 | 82.3 | 105 | 20.8 | 19.0 | 1.097 | 3.1 ± 0.7 | 32.6 |
| | P18 | 82.0 | 195 | 38.4 | 34.9 | 1.099 | 3.8 ± 0.5 | 30.1 |
| | P19 | 83.0 | 289 | 56.8 | 52.8 | 1.075 | 4.3 ± 0.5 | 28.8 |
| | P20 | 82.3 | 404 | 79.4 | 67.7 | 1.173 | 5.9 ± 1.3 | 26.7 |
| EG2$_{90\%}$ | P21 | 89.6 | 103 | 20.1 | 18.2 | 1.102 | 3.0 ± 0.5 | 30.8 |
| | P22 | 92.0 | 210 | 40.6 | 35.3 | 1.151 | 3.5 ± 0.3 | 28.9 |
| | P23 | 90.0 | 315 | 61.0 | 55.2 | 1.105 | 4.1 ± 0.5 | 27.0 |
| | P24 | 90.0 | 405 | 78.2 | 66.2 | 1.182 | 4.8 ± 0.4 | 25.0 |
| EG2$_{100\%}$ | P25 | 100 | 190 | 36.0 | 32.3 | 1.116 | 3.1 ± 0.5 | 25.8 |

FIG. 4

| Compound name | EG2 % | POEGMA DP | Tt at injected concentration (°C) | Mn (kDa) | Đ (Mw/Mn) | Rh (nm) | EC50 (nM) |
|---|---|---|---|---|---|---|---|
| Exendin | NA | NA | NA | 4.2* | 1.000† | 2.2 ± 0.10 | 0.04 ± 0.01 |
| Ex-POEGMA$_{31.9}$ | 48.6 | 247 | 31.9 | 57.7 | 1.153 | 4.8 ± 0.74 | 4.75 ± 0.84 |
| Ex-POEGMA$_{29.9}$ | 60.5 | 253 | 29.9 | 57.6 | 1.148 | 4.4 ± 0.91 | 2.04 ± 0.37 |
| Ex-POEGMA$_{28.4}$ | 69.5 | 254 | 28.4 | 56.9 | 1.132 | 4.5 ± 0.75 | 7.54 ± 1.26 |

FIG. 9

STIMULI-RESPONSIVE PEG-LIKE POLYMER-BASED DRUG DELIVERY PLATFORM

CROSS-REFERENCE TO RELATED APPLICATIONS

This patent application is the U.S. national stage entry, under 35 U.S.C. § 371, of International Application Number PCT/US2019/030022, filed Apr. 30, 2019, which claims priority to U.S. Provisional Patent Application No. 62/664,512, filed Apr. 30, 2018, the entire contents of each of which are hereby incorporated by reference.

TECHNICAL FIELD

The present disclosure relates to a novel drug delivery platform.

BACKGROUND OF THE INVENTION

Therapeutic biomolecules have some significant limitations as drugs; they typically have a short plasma half-life, and some peptides and proteins have poor stability in circulation. These attributes lead to their rapid in vivo elimination, which necessitates frequent injections that result in high treatment costs and suboptimal patient compliance and thus limits their utility as therapeutics. To overcome this limitation, therapeutic biomolecules are often covalently attached to linear polyethylene glycol (PEG) moieties, termed PEGylation. Originally, these PEGylated biomolecules were believed to have minimal interaction with proteins and cells, due to the "stealth" properties of PEG. However, PEG moieties have been reported to induce anti-PEG antibodies (anti-PEGS) upon treatment. In addition to inducing anti-Pairs, these PEGylated biomolecules have shown reactivity with pre-existing anti-PEGS, Which have been reported in individuals naive to PEGylated therapeutics, possibly due to chronic exposure to PEG in consumer products. Both induced and pre-existing anti-PEGs have caused severe immune reaction and accelerated drug clearance, which have collectively led to early termination of clinical trials of PEGylated drugs and reduced clinical efficacy and safety of PEGylated therapeutics that are already in the market.

There remains a need, therefore, for new therapeutic biomolecule delivery systems that can overcome the short plasma half-life and poor stability of existing therapeutics while not inducing antibodies or cross reacting with pre-existing anti-PEG antibodies.

BRIEF SUMMARY OF THE INVENTION

In one aspect, the disclosure provides thermally responsive polymer-therapeutic molecule conjugate comprising a backbone comprising repeating monomer units selected from the group consisting of acrylate, methacrylate, acrylamide, methacrylamide, and combinations thereof; a plurality of oligoethylene glycol side chains; and a therapeutic molecule conjugated to the backbone; wherein a first end each oligoethylene glycol side chain is covalently attached to the backbone and each oligoethylene glycol side chain comprises two or three monomers of ethylene glycol repeated in tandem, and wherein the conjugate has a transition temperature between 23° C. and 40° C.

In another aspect, the disclosure provides a drug depot comprising the thermally responsive polymer-therapeutic molecule conjugates described herein.

In another aspect, the disclosure provides a method of treating a disease or disorder in a subject in need thereof comprising administering a therapeutically effective amount of the thermally responsive polymer-therapeutic molecule conjugates described herein.

Other aspects and embodiments of the disclosure will become apparent in light of the following description and drawings.

BRIEF DESCRIPTIONS OF FHE DRAWINGS

Figure 3A:
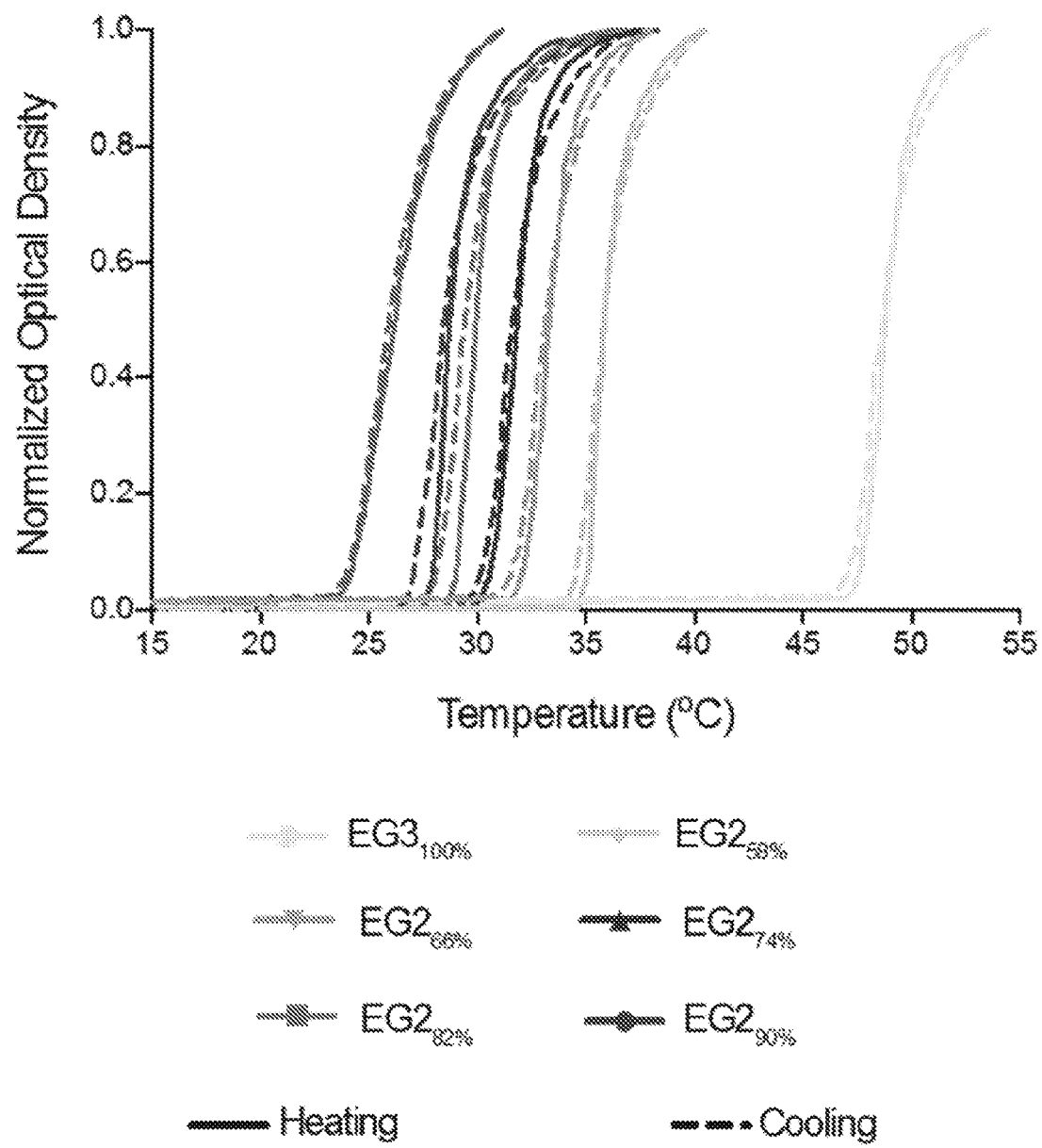
Figure 3B:
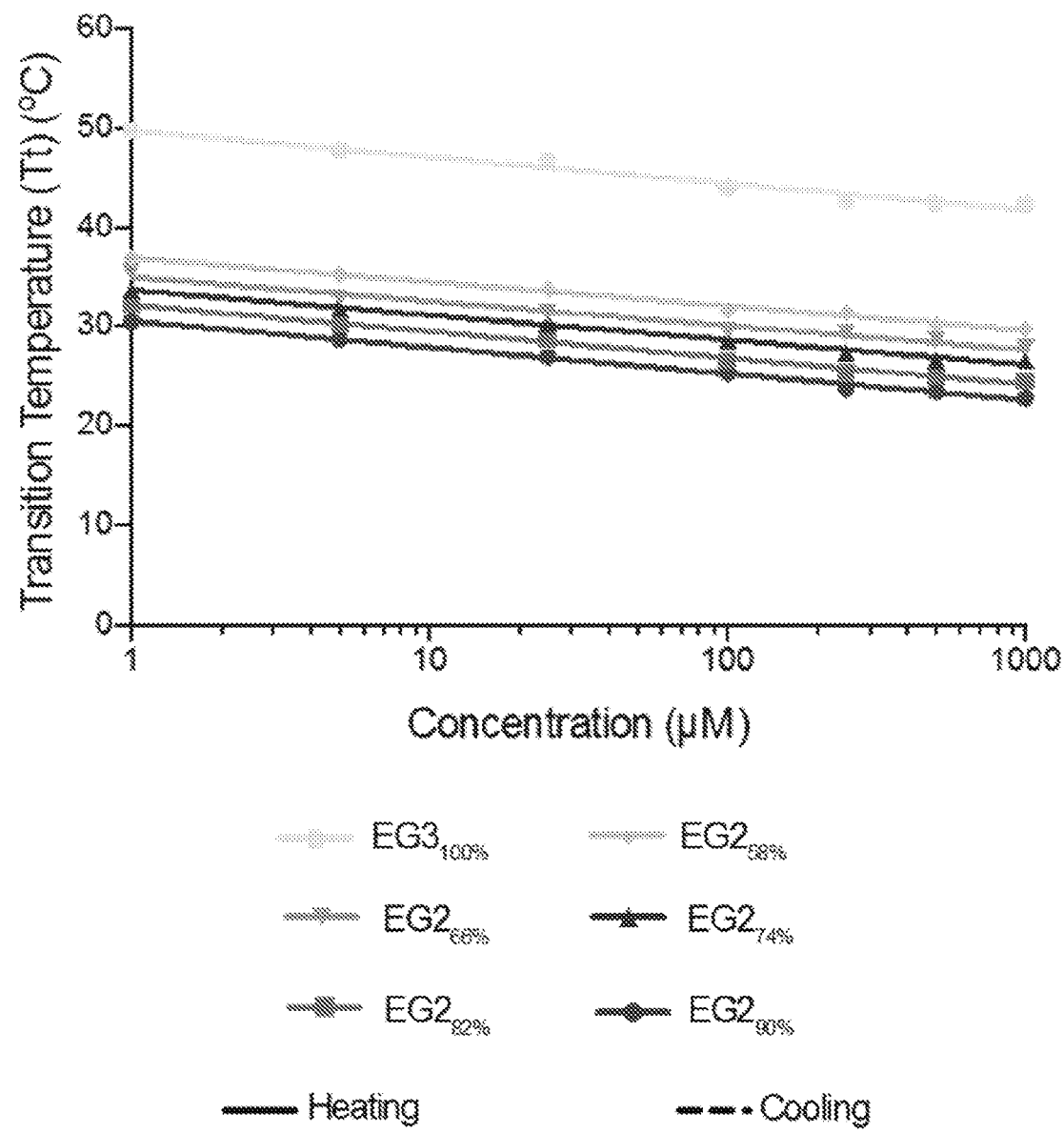
Figure 3C:
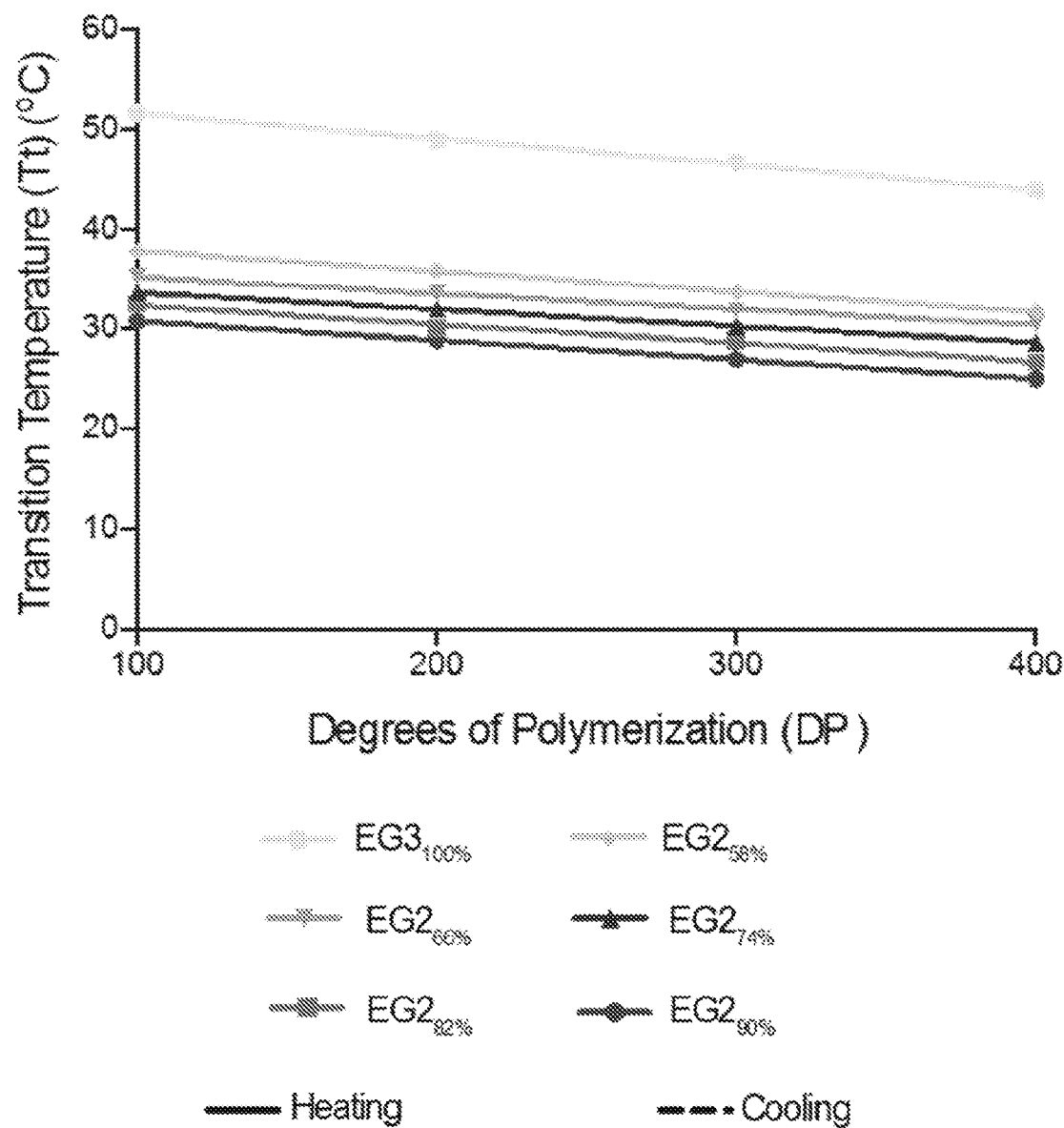

FIG. 3A, FIG. 3B, and FIG. 3C are graphs of the characterization of phase behavior of POEGMA. Optical density of POEGMAs with constant degrees of polymerization (DP) but varying monomer composition was monitored (FIG. 3A) as temperature increased (solid line) and decreased (dashed line) to demonstrate reversibility of phase behavior (data shown for POEGMAs at DP 200 and 25 µM in phosphate buffered saline (PBS) at pH 7.4; n=1). The transition temperature was determined at varying concentrations (FIG. 3B) to demonstrate concentration-dependence of $T_t$ (data shown for POEGMAs at degrees of polymerization (DP) of 300 in phosphate buffered saline (PBS) at pH 7.4; n=1). Optical density of POEGMAs with varying DP and monomer composition was monitored to demonstrate DP-dependence of $T_t$ (FIG. 3C, data shown for POEGMAs at constant concentration (25 µM) in phosphate buffered saline (PBS) at pH 7.4; n=1).

FIG. 4 is a summary table of POEGMA library characterization data. EG2 composition values were derived from NMR spectra. Mw and Đ values were determined by gel permeation chromatography—multi-angle light scattering (GPC-MALS). DP values were calculated by subtracting mass of initiator from Mw and then dividing the resulted mass to average mass of monomeric unit at the indicated monomer composition. Hydrodynamic size ($R_h$) was measured by dynamic light scattering. $T_t$ values were derived from UV-vis spectrophotometry curves.

Figure 5A:
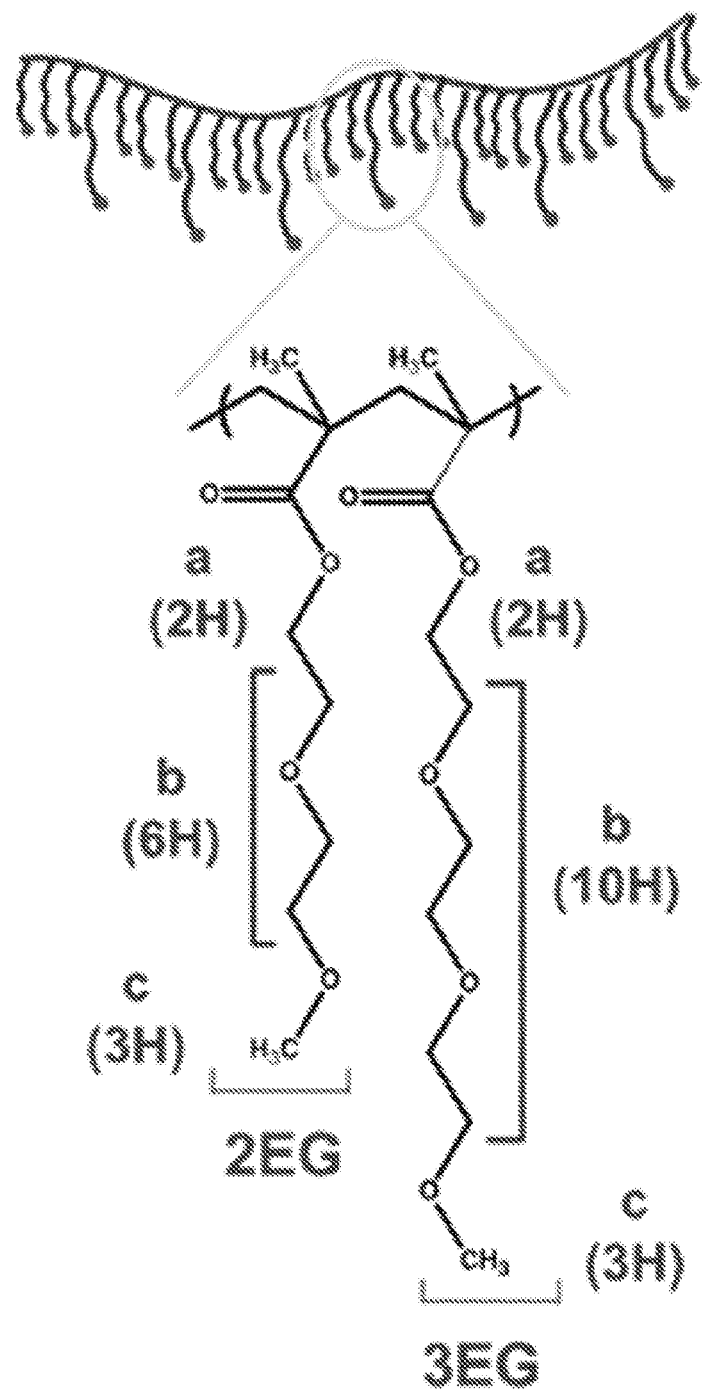
Figure 5B:
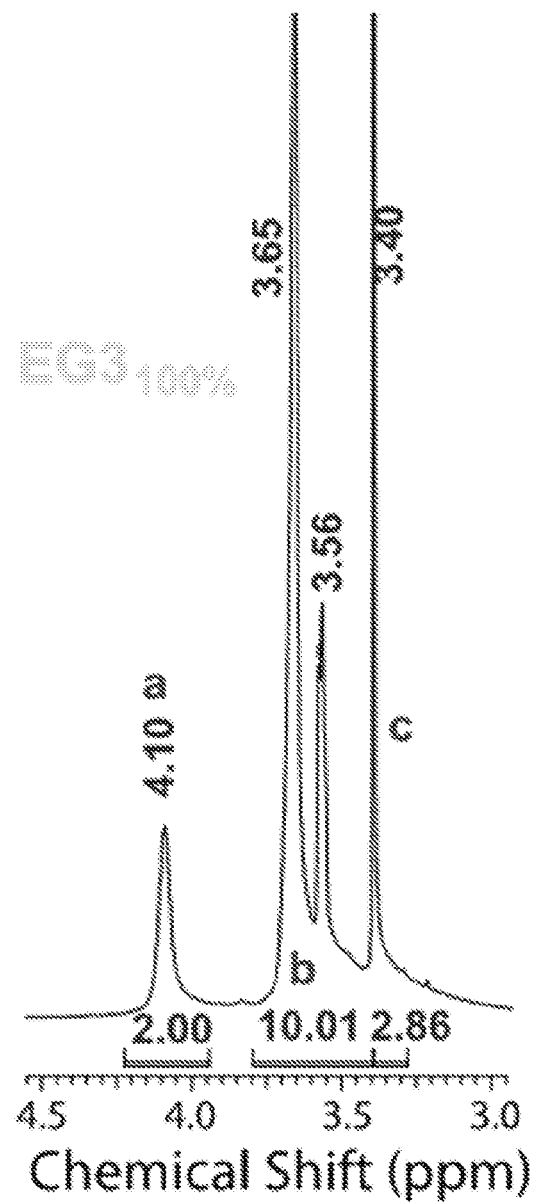
Figure 5C:
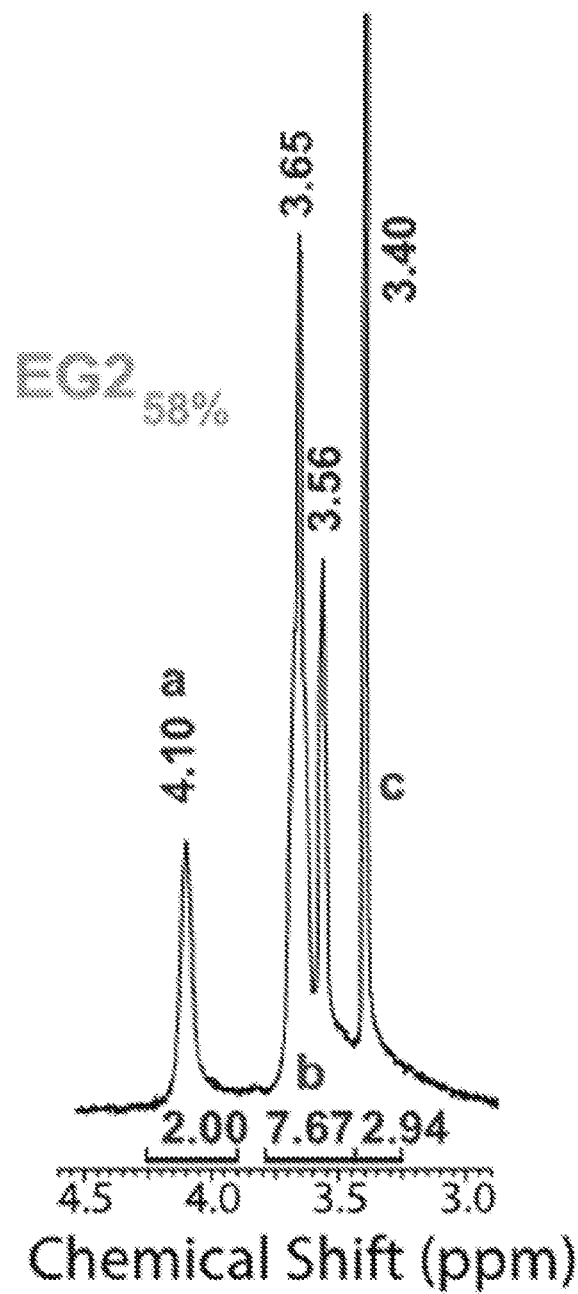
Figure 5D:
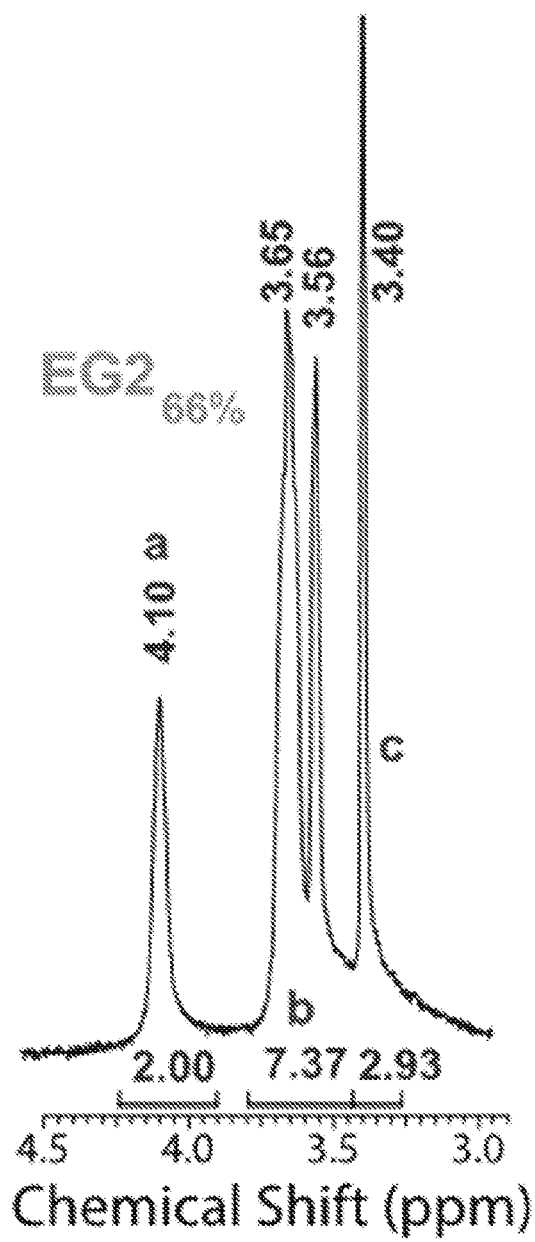
Figure 5E:
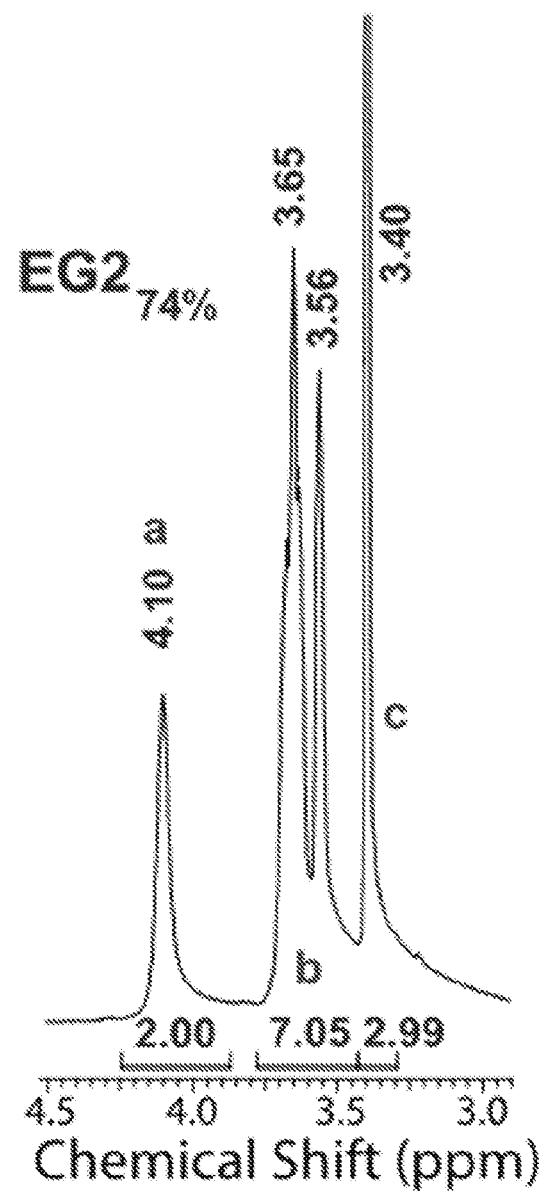
Figure 5F:
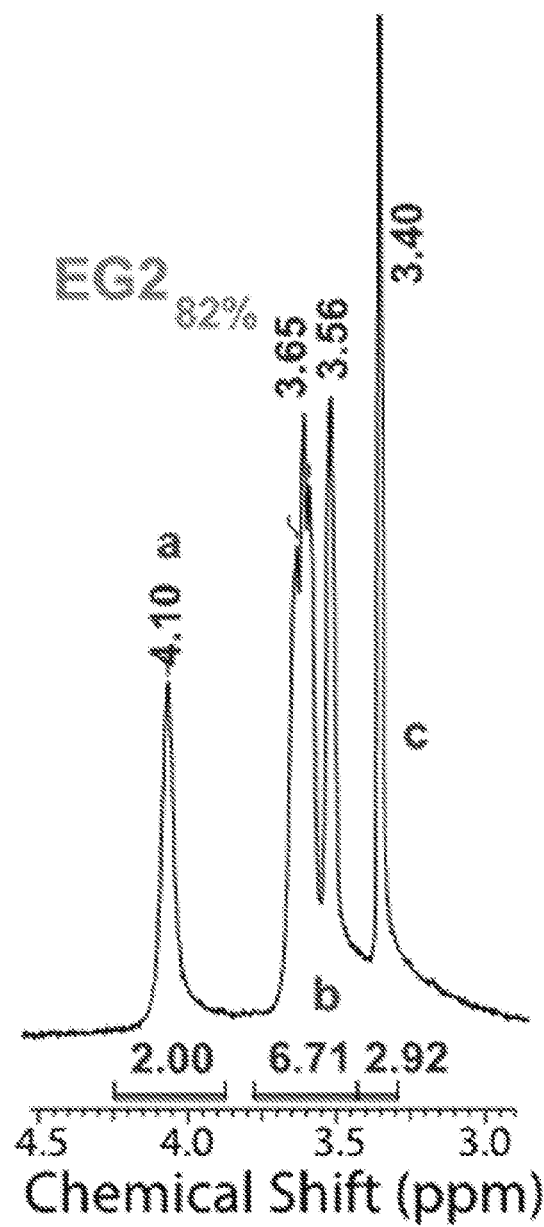
Figure 5G:
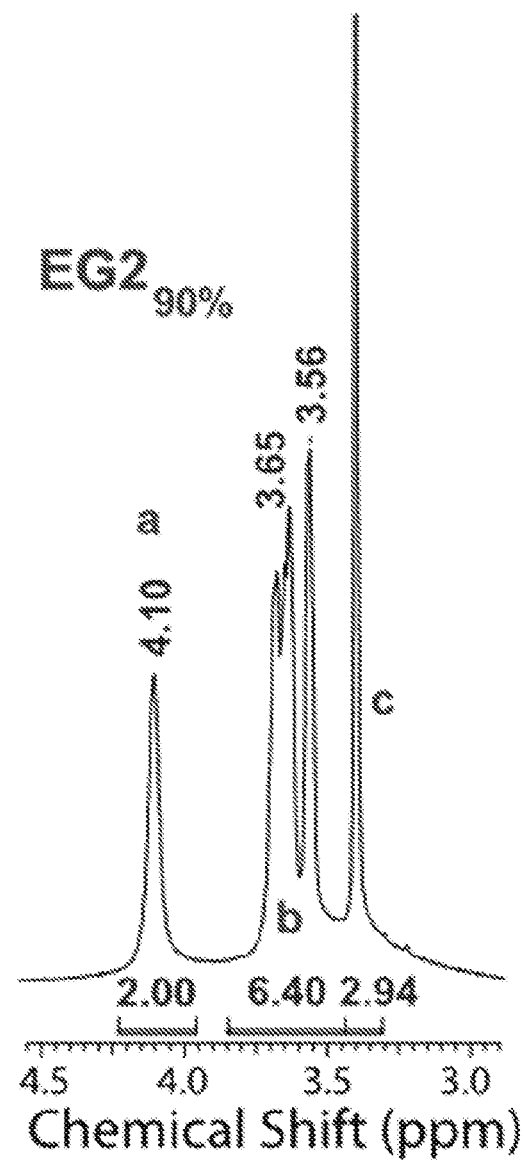
Figure 5H:
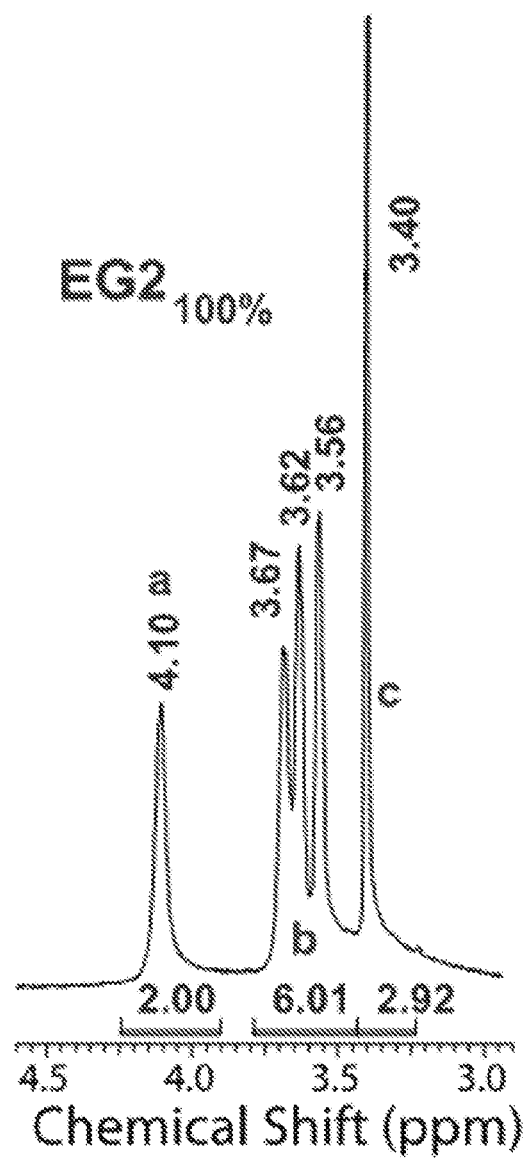

FIG. 5A, FIG. 5B, FIG. 5C, FIG. 5D, FIG. 5E, FIG. 5F, FIG. 5G, and FIG. 5H are NMR spectra of monomer composition of POEGMA library. FIG. 5A shows a schematic of the NMR analysis of the EG side chains. Monomer composition of POEGMAs (EG3$_{100\%}$ (FIG. 5B), EG2$_{58\%}$ (FIG. 5C), EG2$_{60\%}$ (FIG. 5D), EG2$_{74\%}$ (FIG. 5E), EG2$_{82\%}$ (FIG. 5F), EG2$_{90\%}$ (FIG. 5G), and EG2$_{100\%}$ (FIG. 5H)) was defined as 2EG-Long monomer content (%) as identified via hydrogen nuclear magnetic resonance (H-NMR) spectroscopy. 2EG-long monomer content (%) (y) was calculated by applying a linear fit, y=(−25* b)+250, to the integral value that corresponds to average number of H present in the OEG side-chain (b; 3.4-4.4 ppm; 6 H EG2$_{100\%}$; 10 H EG3$_{100\%}$) except chain end-group (c; 3.5-3.3 ppm; 3 H) and methylene protons (a; 4.0-4.4 ppm; 2 H). The linear fit was formed based on the fact that POEGMA that consists of only 2EG-long side chains (EG2$_{100\%}$; y=100%) has 6 H in the OEG side-chain (b) while 10 H present in the OEG side-chain (b) of POEGMA that consists of only 3EG-long side chains (EG2$_{0\%}$ or EG3$_{100\%}$; y=0%)). Deuterated chloroform was used as solvent.

Figure 6:
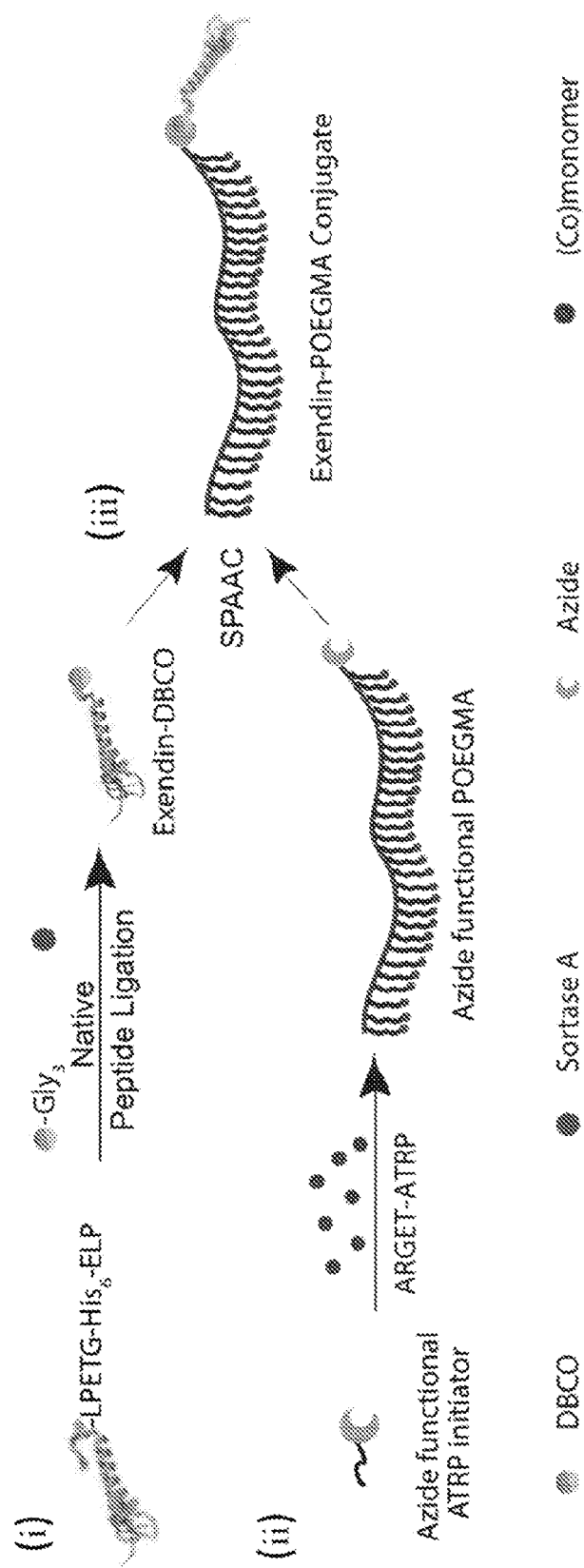

FIG. 6 is a schematic of the overview of site-specific and stoichiometric exendin-POEGMA conjugation approach. (i)

Installation of bio-orthogonal dibenzocyclooctyne (DBCO) group on C terminus of exendin via sortase-A mediated native peptide ligation. Sortase A recognizes LPETG sequence on exendin-LPETG-His$_6$-ELP, where ELP is elastin-like polypeptide, and catalyzes a transpeptidation reaction using triglycine DBCO, yielding exendin-DBCO. (ii) Installation of a bio-orthogonal azide group on POEGMA using an azide functional polymerization initiator in ARGET-ATRP. (iii) Strain-promoted azide-alkyne cycloaddition (SPAAC) to synthesize exendin-POEGMA conjugates.

Figure 7:
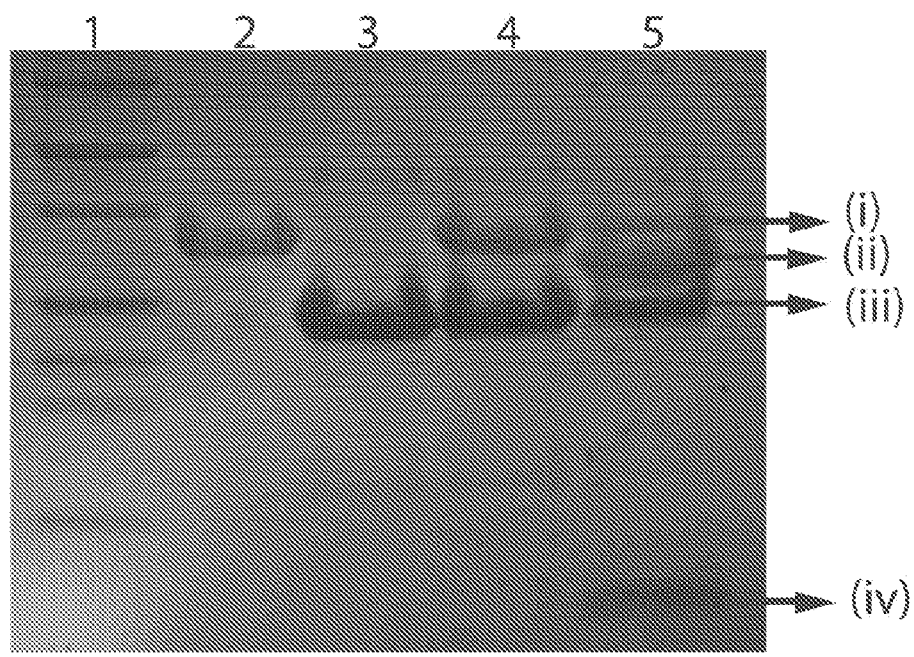

FIG. 7 is SDS PAGE analysis of the expression, purification and characterization of exendin-DBCO with a coomassie-stained SDS-PAGE gel of DBCO attachment on exendin by sortase A. Lane 1: Mw marker; lane 2: exendin-LPETG-His$_6$-ELP, where ELP is elastin-like polypeptide; lane 3: sortase-A; lane 4: reaction mixture immediately after mixing; lane 5: reaction mixture after 18 h of reaction. (i) Unreacted exendin-srt-His$_6$-ELP; (ii) cleaved G-His$_6$-ELP; (iii) His$_6$-sortase A; (iv) exendin-DBCO.

Figure 8A:
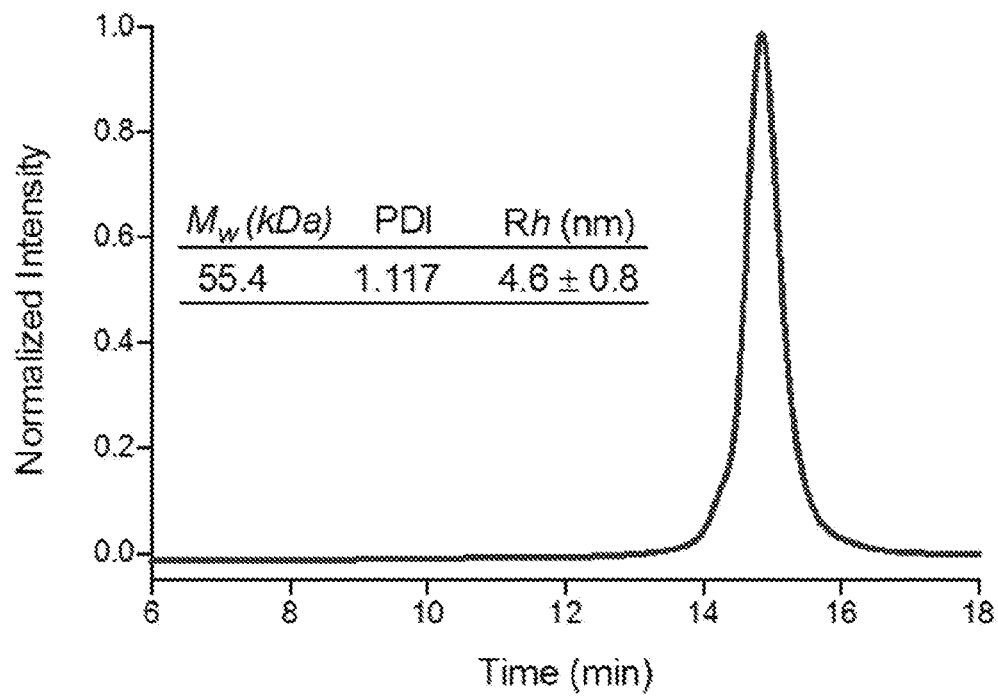
Figure 8B:
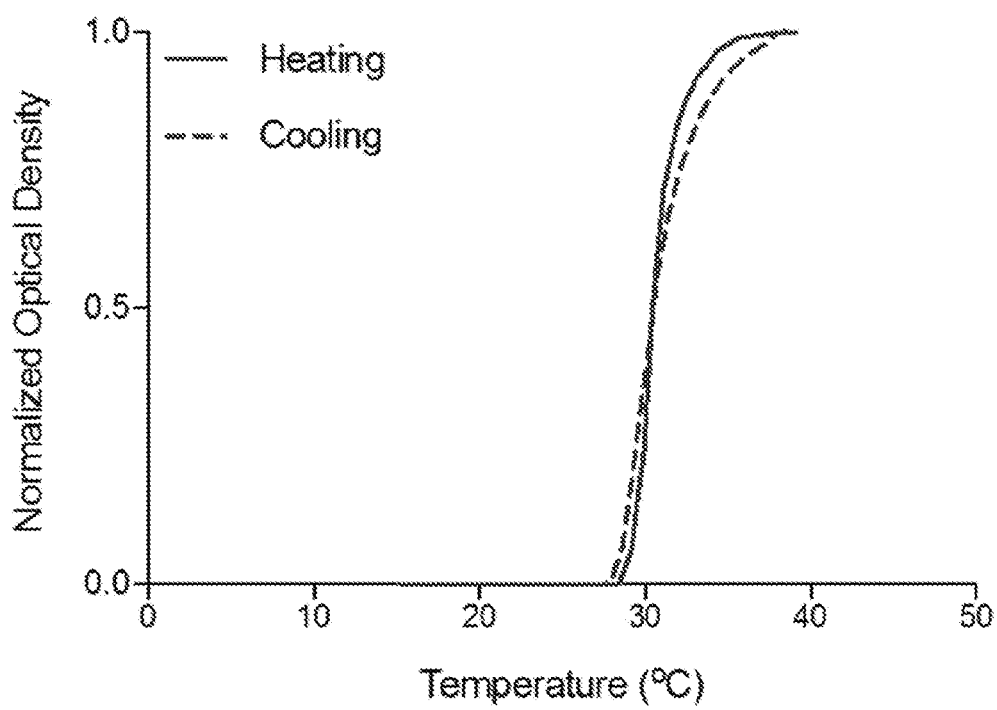
Figure 8C:
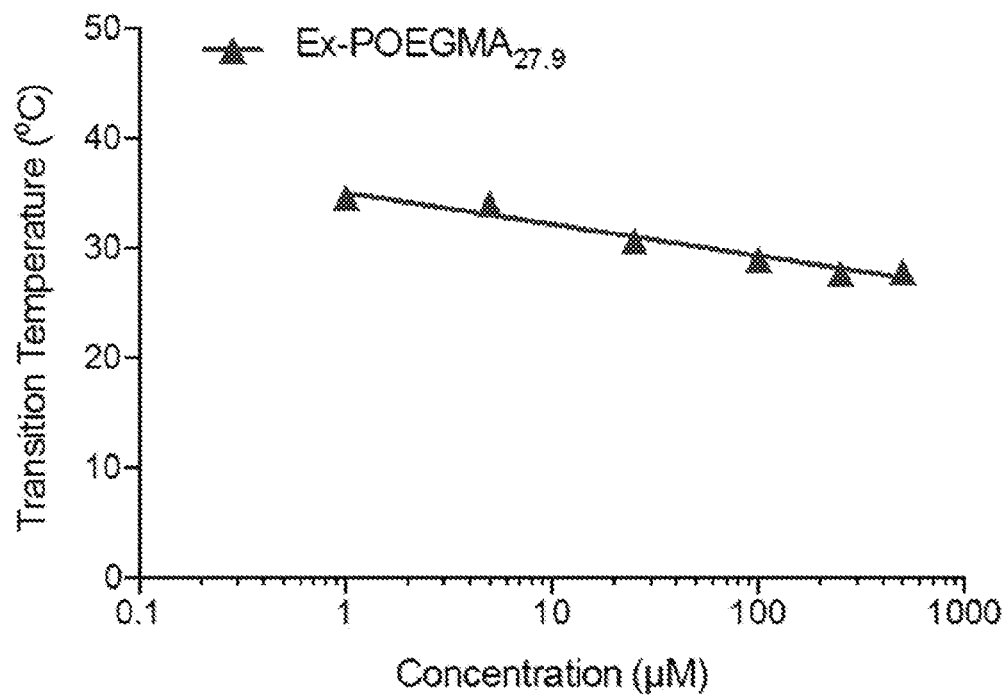
Figure 8D:
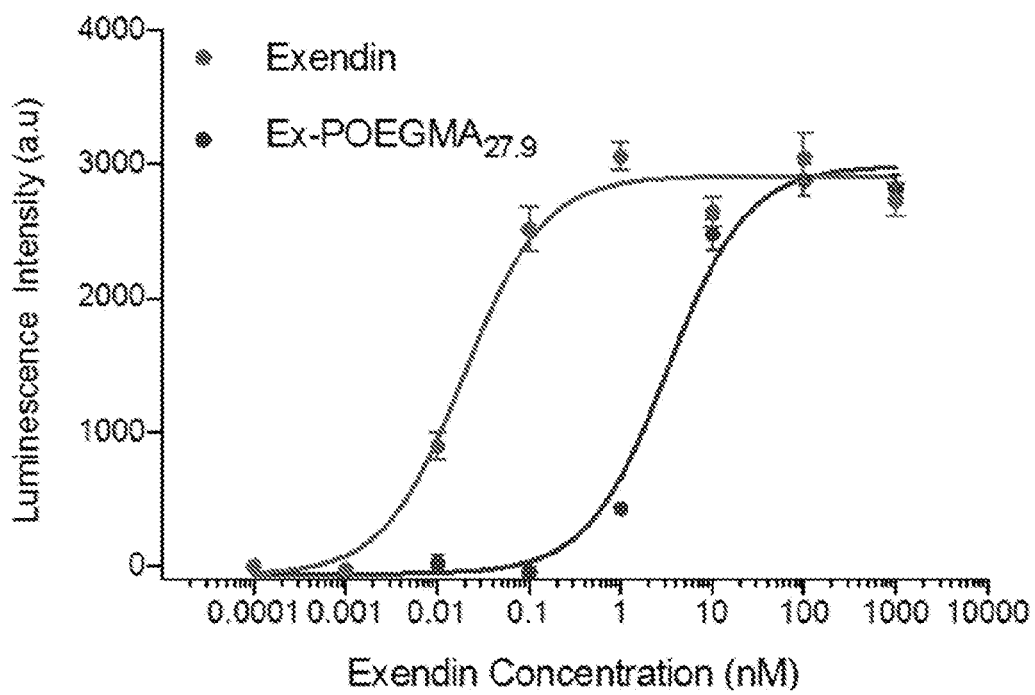

FIG. 8A, FIG. 8B, FIG. 8C, and FIG. 8D show the characterization of injectable and depot-forming Ex-POEGMA$_{27.9}$ conjugate used in dose-response experiment. FIG. 8A shows the SEC-MALS trace with Mw, polydispersity (PDI) and hydrodynamic size in PBS in soluble state. FIG. 8B is a graph in the change in optical density as temperature increased (solid line) and decreased (dashed line) at 25 μM in PBS at pH 7.4. FIG. 8C is a graph of the concentration-dependent $T_t$ change at various concentrations in PBS at pH 7.4. FIG. 8D is a graph of the in vitro activity compared to unconjugated exendin. *Index shows $T_t$ at injection concentration.

FIG. 9 is a summary table of the characterization of exendin variants used in short-term efficacy experiment. *Calculated from the amino acid sequence. †Default value due to the unimolecular nature of the peptide. Mn, Mw and Đ values were determined by SEC-MALS. R$_h$ was measured by dynamic light scattering. The EC$_{50}$ values exendin variants were derived from the cAMP response curves in FIG. 2c. R$_h$ and EC50 values are reported as mean ±SEM, n=10 for Rh and n=6 for EC$_{50}$.

Figure 10A:
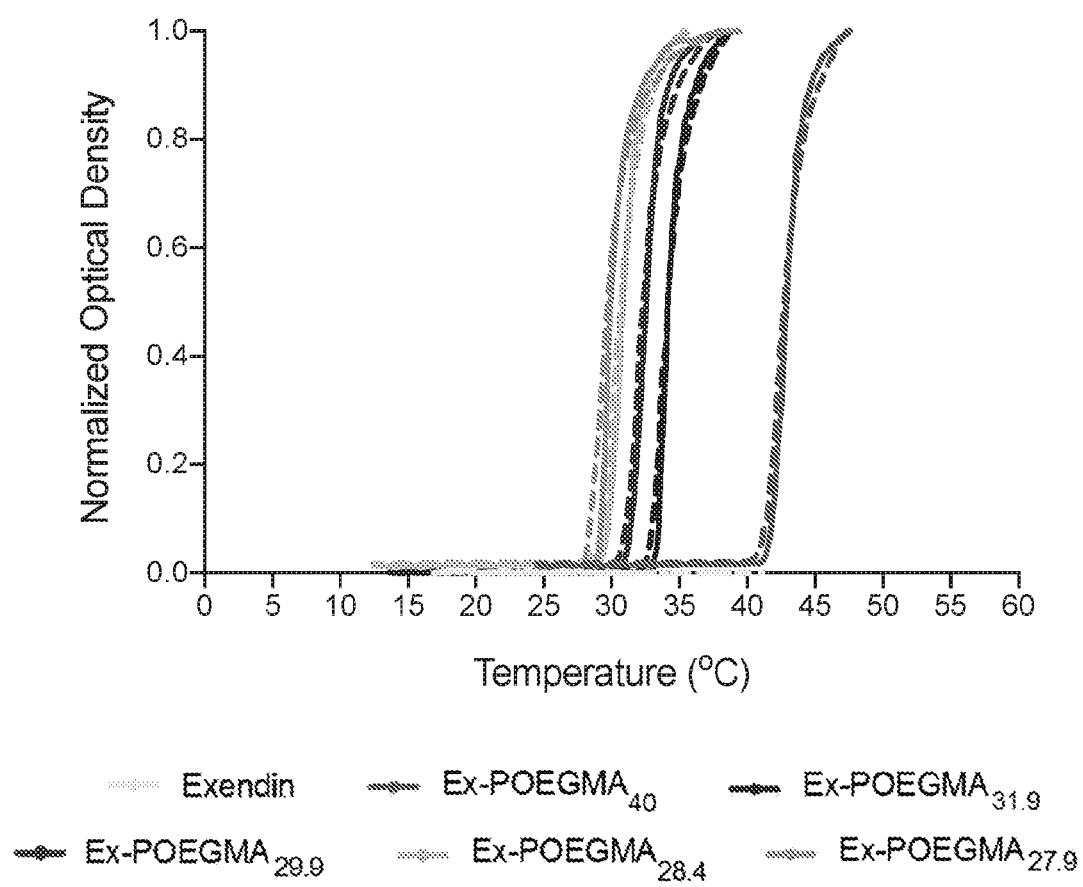
Figure 10B:
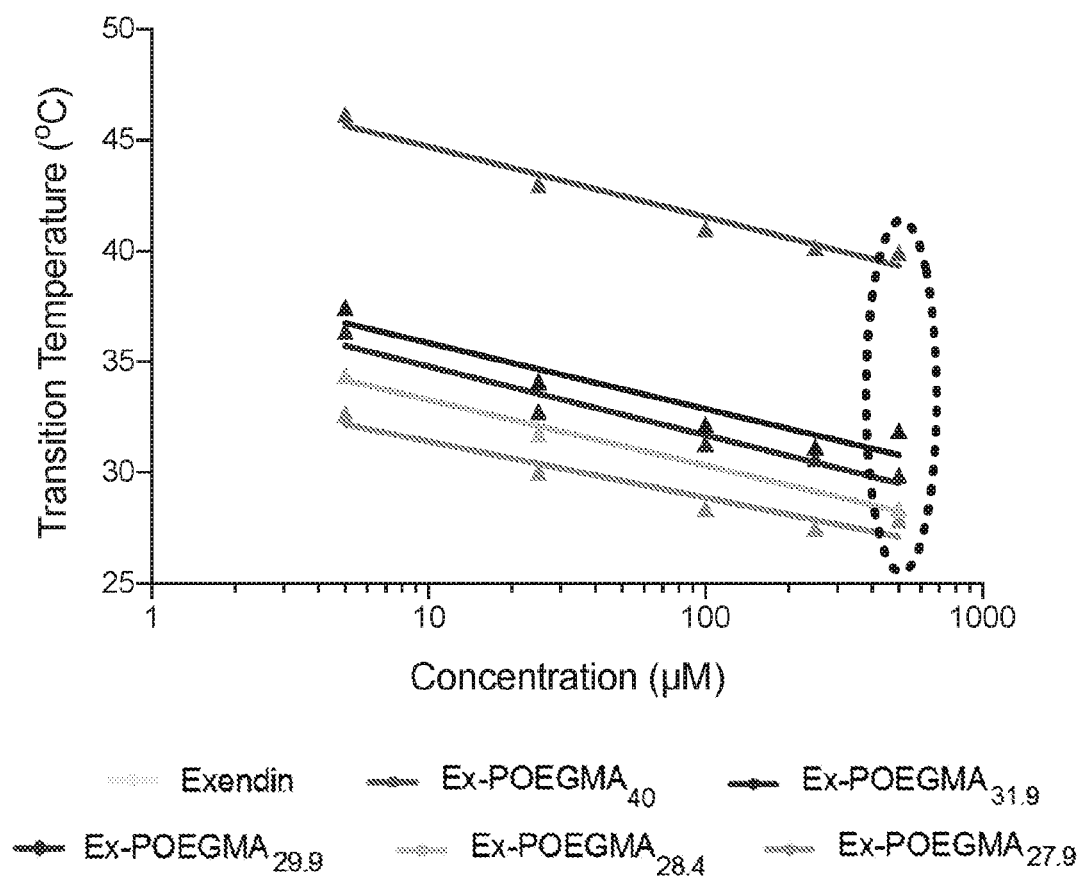
Figure 10C:
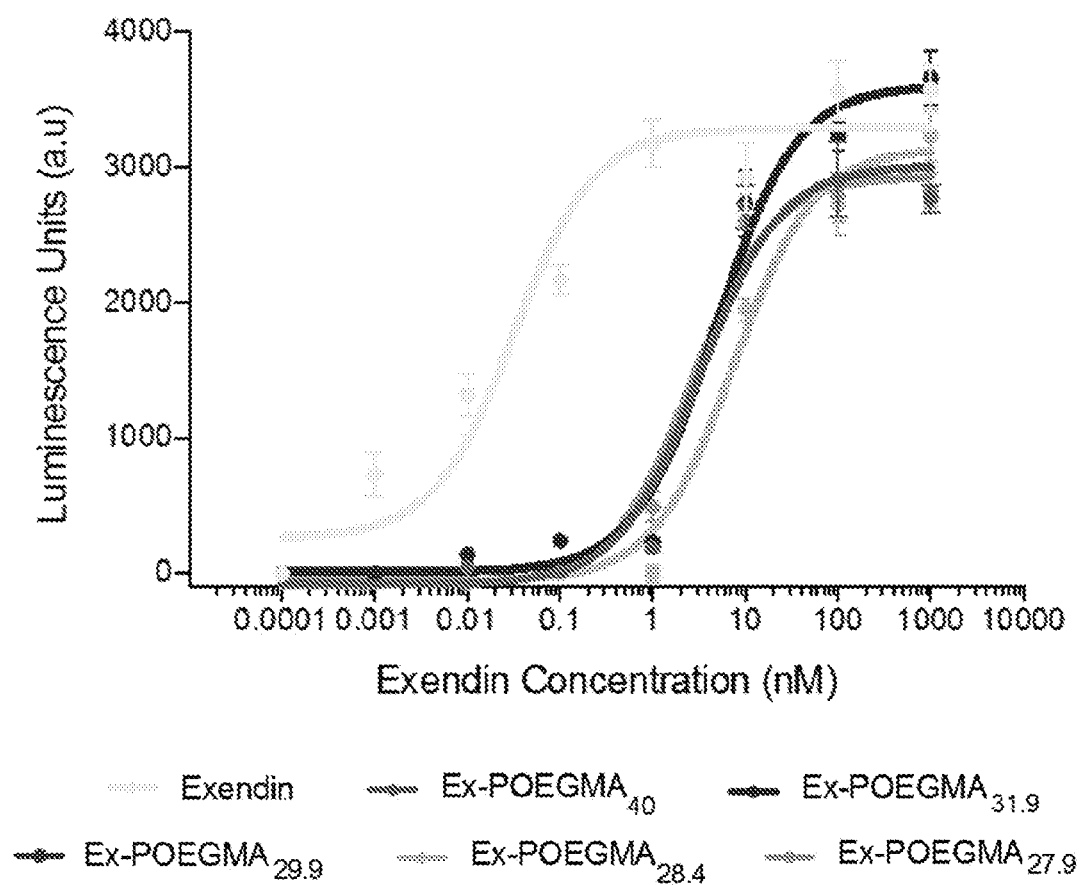
Figure 11A:
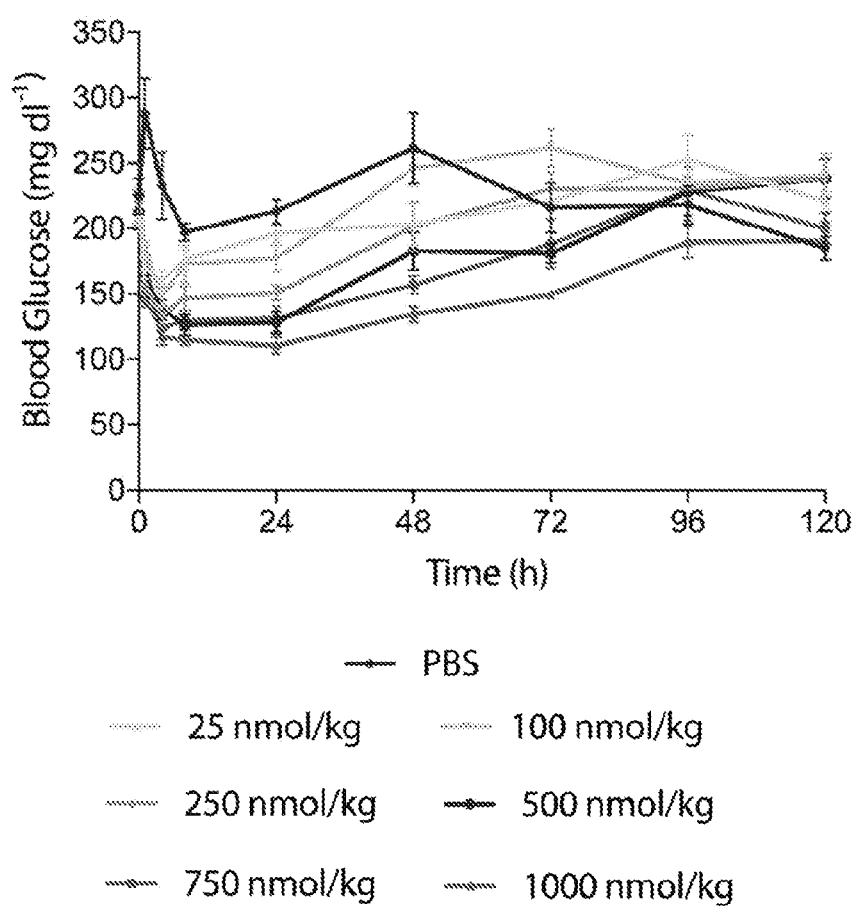
Figure 11B:
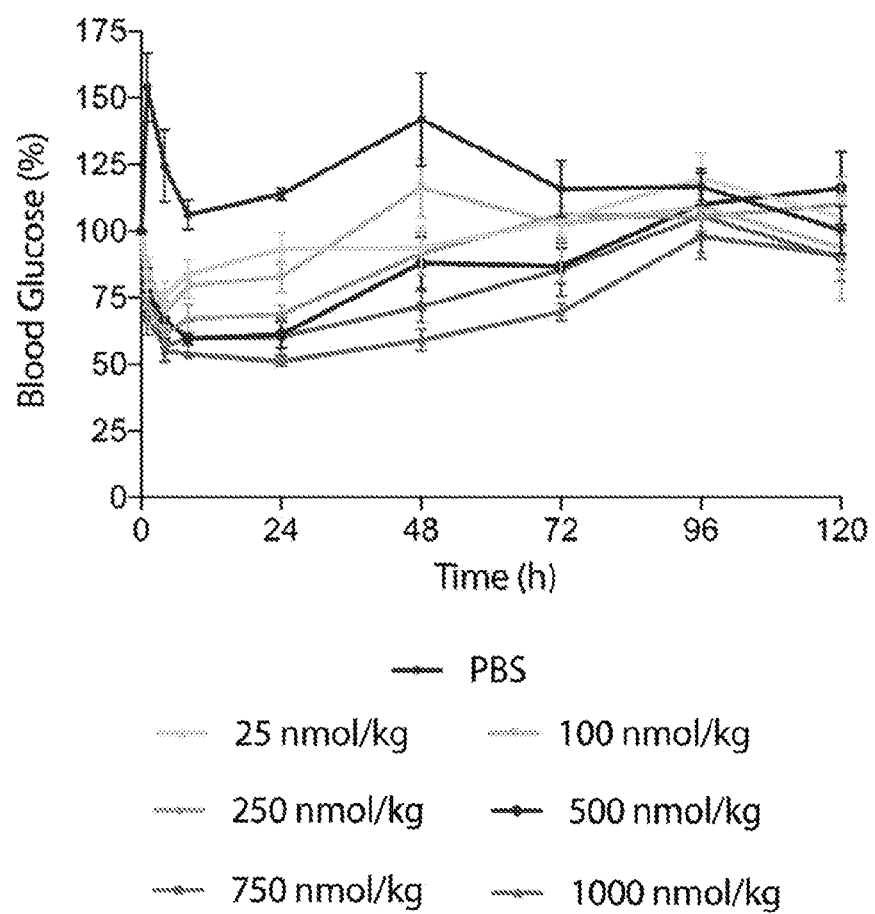
Figure 11C:
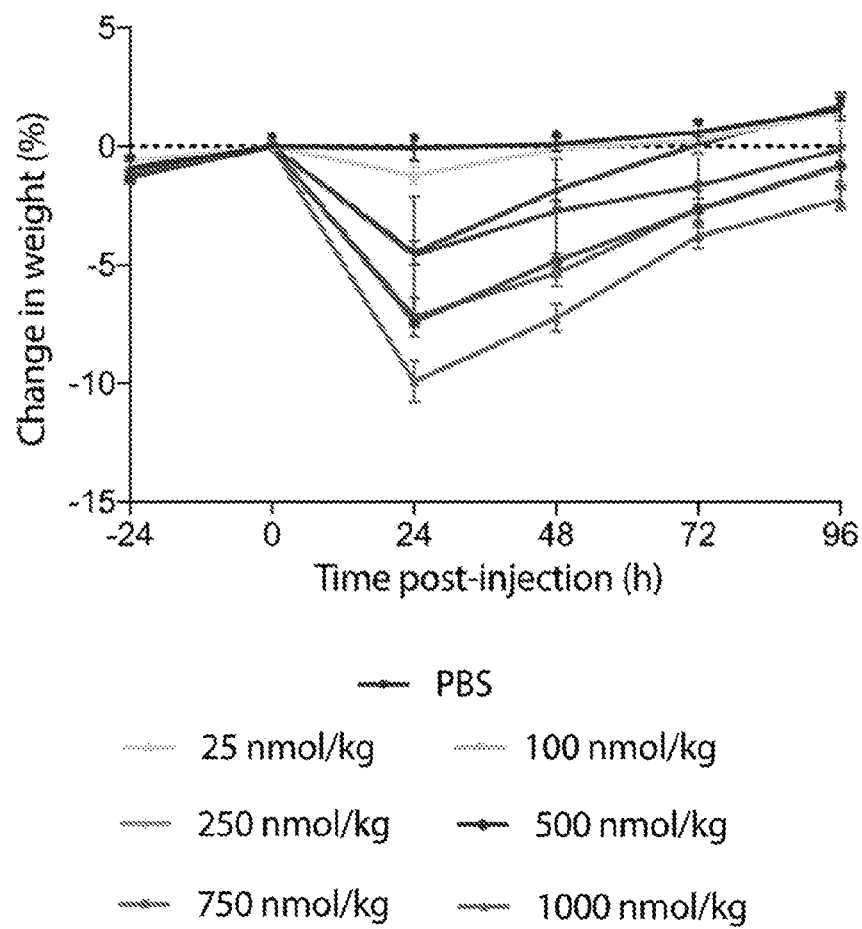
Figure 11D:
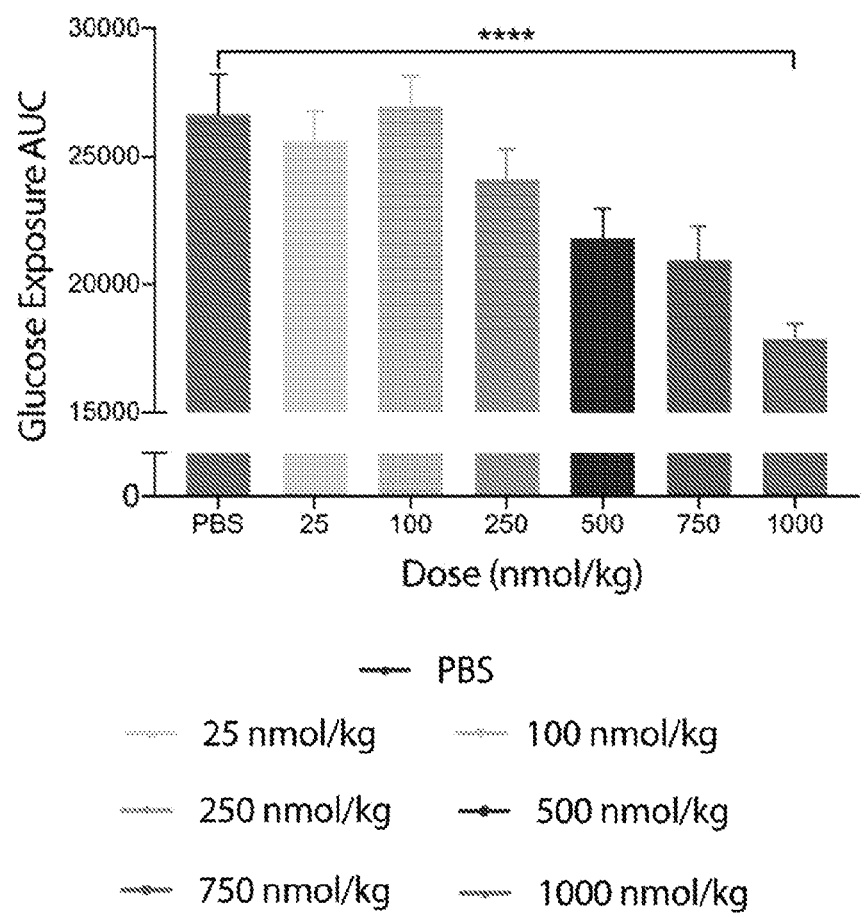

FIG. 10A, FIG. 10B, and FIG. 10C are graphs of the characterization of Ex-POEGMA conjugates at the same molecular weight but varying transition temperatures ($T_t$). FIG. 10A is a graph of the optical density changes of conjugates with constant molecular weight but varying $T_t$ was monitored as temperature increased (solid line) and decreased (dashed line) to demonstrate reversibility of phase behavior at 25 μM in phosphate buffered saline (PBS) at pH 7.4; n=1). The transition temperature was determined at varying concentrations (FIG. 10B) to demonstrate concentration-dependence of $T_t$ in phosphate buffered saline (PBS) at pH 7.4; n=1. FIG. 10C is a graph of the in vitro activity of Ex-POEGMA conjugates in comparison to non-conjugated exendin. *Data represent the mean and standard error of the mean (SEM). *Index shows $T_t$ at injection concentration.

FIG. 11A, FIG. 11B, FIG. 11C, and FIG. 11D are graphs of the dose-response of Exendin-POEGMA$_{27.9}$. Various doses of Ex-POEGMA$_{27.9}$ were tested in vivo. Unnormalized blood glucose (FIG. 11A), blood glucose normalized to t=0 (FIG. 11B), and percent weight change relative to weight at t=0 (FIG. 11C) were monitored after treating seven-week-old DIO mice (n=6) with a single SC injection at given doses of Ex-POEGMA$_{27.9}$ or PBS control. Area under the curve (AUC) of blood glucose was quantified for each subject (FIG. 11D). *Data represent the mean and standard error of the mean (SEM).

Figure 12A:
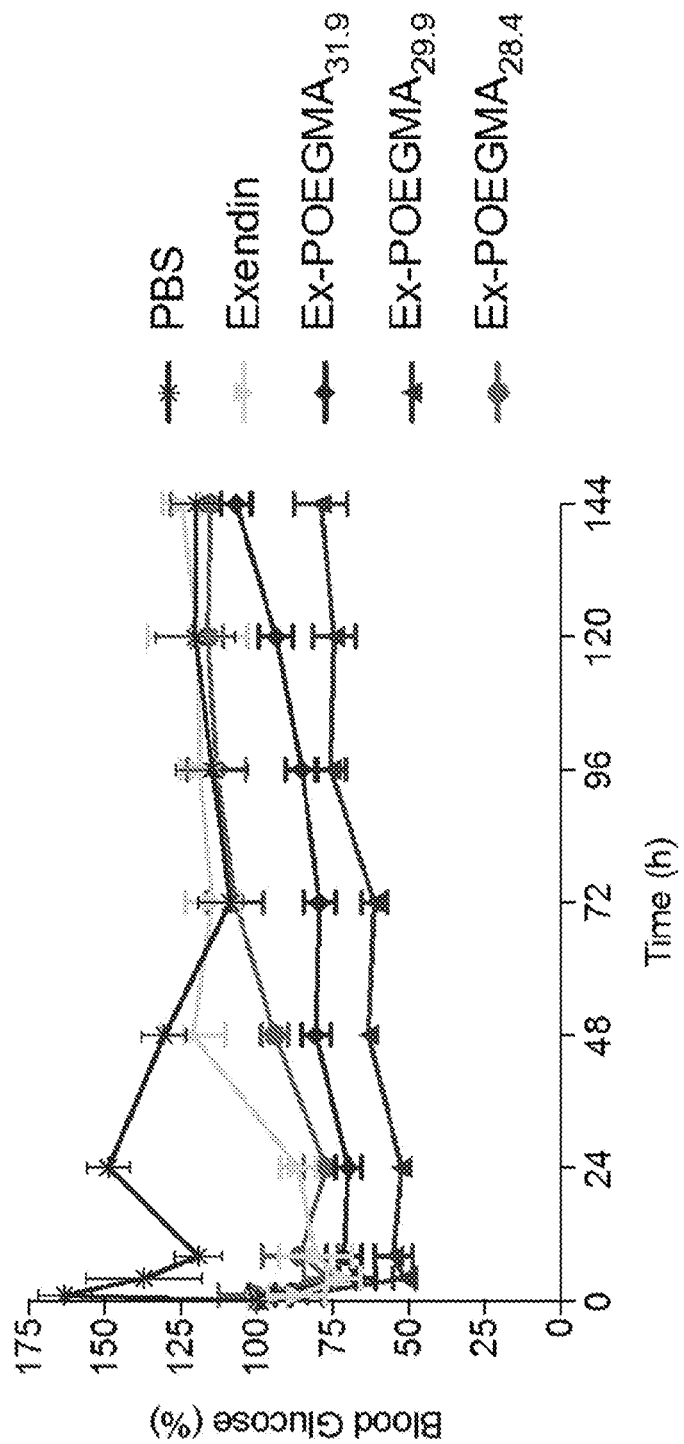
Figure 12B:
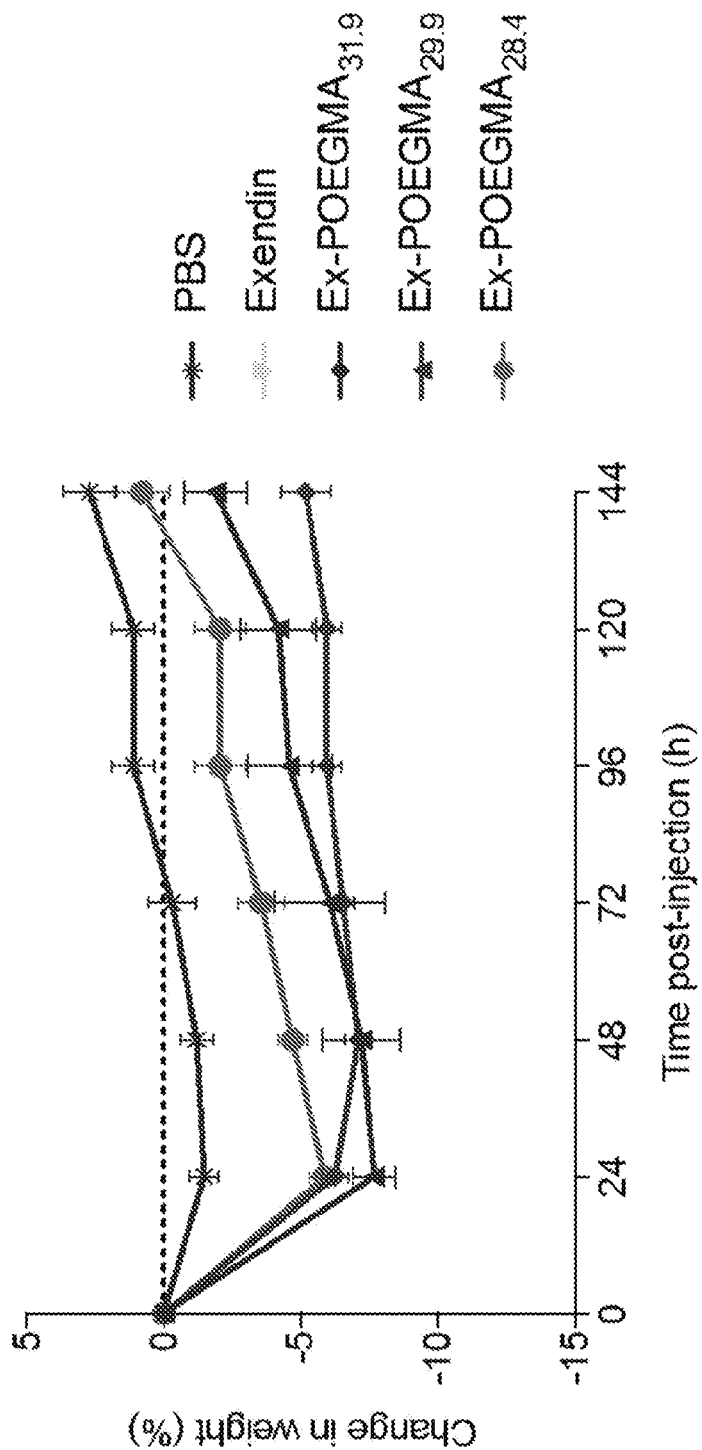
Figure 12C:
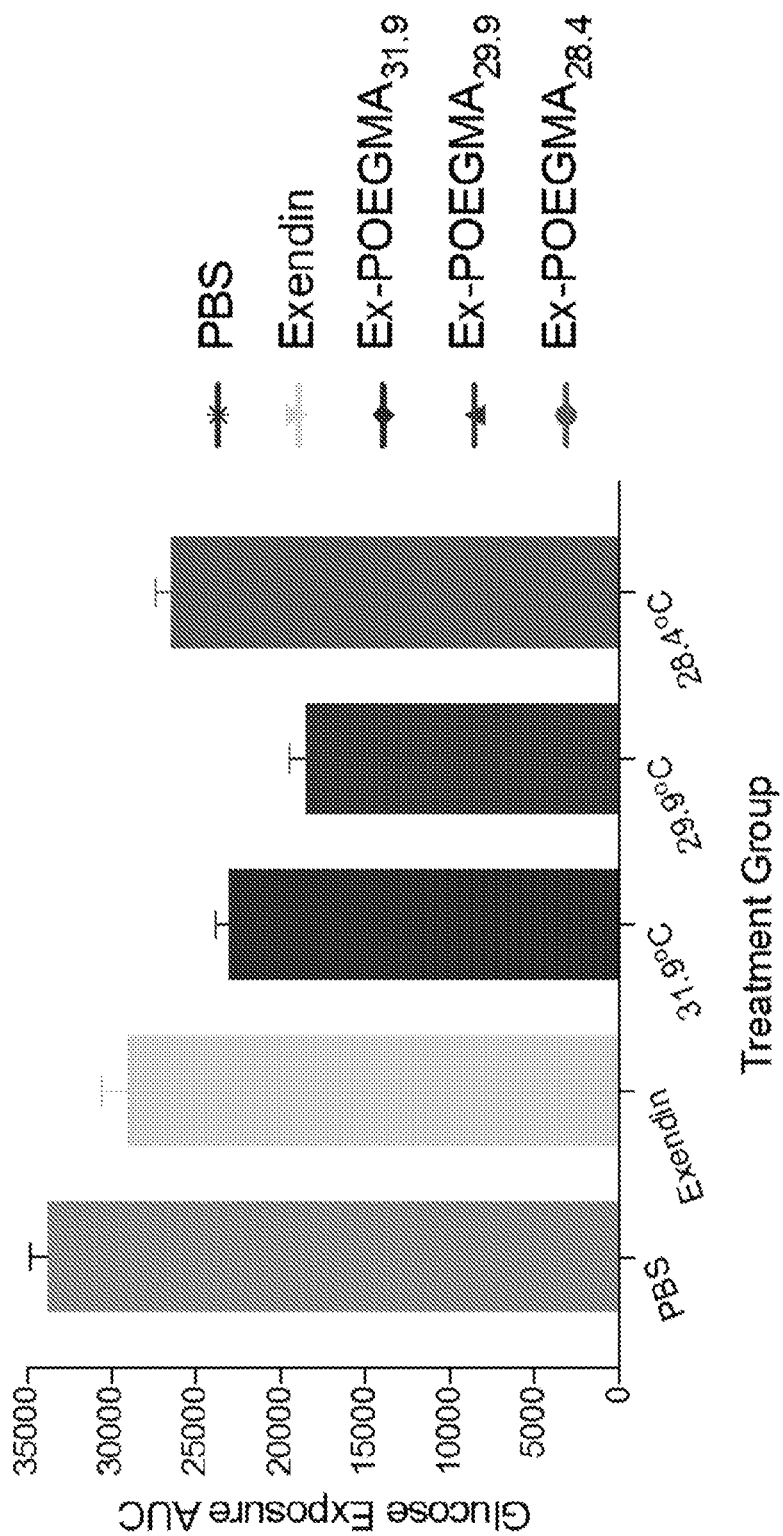

FIG. 12A, FIG. 12B, and FIG. 12C are graphs of the short-term efficacy of Ex-POEGMA depots at indicated $T_t$. Blood glucose normalized to t=0 (FIG. 12A) and percent weight change relative to weight at t=0 (FIG. 12B) were monitored after treating eleven-week-old DIO mice (n=6) with a single SC injection of conjugates, PBS or exendin control. Area under the curve (AUC) of blood glucose was quantified for each subject (FIG. 12C). *Data represent the mean and standard error of the mean (SEM). *Index shows $T_t$ at injection concentration.

DETAILED DESCRIPTION OF THE INVENTION

Disclosed herein is a novel drug delivery system. The delivery system utilizes POEGMA as an injectable depot-based drug delivery platform to improve in vivo efficacy of therapeutics upon their sustained release from subcutaneous depots into bloodstream. A highly tunable amphiphilic structure of POEGMA was engineered such that it undergoes phase transition near body temperature to form depots of therapeutics but remains soluble at room temperature allowing injection. Depot-forming POEGMAs were conjugated to exendin, a potent peptide with a short plasma half-life (~2.4 h) used in the treatment of type 2 diabetes (T2D), and the in vitro and in vivo profiles of the exendin-POEGMA depots were assessed in diabetic mice. Most notably, subcutaneous depots of POEGMA significantly improved in vivo efficacy of exendin by lowering blood glucose for 6 days and providing significant body weight lowering benefits. These findings established depot-forming POEGMAs as a possible next generation stealth polymer conjugate technology superior to immunogenic PEGylation to bring therapeutic biomolecules with intrinsic sub-optimal pharmacokinetics into clinical use.

The innovative stimuli-responsive "PEG-like" stealth drug delivery system offers great advantages and has a wide application area in pharmaceutical industry. First, this stealth drug delivery system allows for efficient delivery of therapeutic conjugates in depot formulation with improved pharmacokinetics necessitating less frequent injections and thus increasing patient compliance. Second, this system offers great versatility in terms of achieving tunable release of therapeutic compounds of interest and thus desired pharmacokinetics owing to its easily tunable amphiphilicity, which allows wide utility in pharmaceutical industry as many drugs have varying therapeutic windows. Third, this system allows for local delivery of therapeutics directly to a region of interest so that sustained release of the compound of interest at the selected region is provided. This feature of the system allows for efficient delivery of therapeutics that have high systemic toxicity such as chemotherapy agents and offers a wide application area since reducing the unwanted side-effects of such treatments has been long-desired. Lastly, this system allows for effective delivery of therapeutics that do not suffer from a harmful interaction with pre-existing anti-PEG antibodies.

The stimuli-responsive "PEG-like" stealth drug delivery system also represents a potential strategy to combat the growing problem of PEG antigenicity, as evidenced by the halted clinical trial of pegnivacogin (PEGylated Factor IXa aptamer, Regado Biosciences) due to the reactivity against pre-existing anti-PEG antibodies, and thus has a wide application in pharmaceutical industry where eliminating PEG antigenicity is desired. Consequently, the stimuli responsive "PEG-like" stealth drug delivery system offers great advantages allowing it to have a wide application area in pharmaceutical industry and has a potential to replace the PEGylation technology.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6,2, 6.3, 6.4, 6,5, 6.6, 6.7, 6.8, 6.9, and 7.0 are explicitly contemplated.

As used herein, the terms "administering," "providing" and "introducing" are used interchangeably herein and refer to the placement of the compositions of the disclosure into a subject by a method or route which results in at least partial localization of the composition to a desired site. The compositions can be administered by any appropriate route which results in delivery to a desired location in the subject.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl" refers to a straight or branched hydrocarbon chain, containing the indicated number of carbon atoms. For example, $C_1$-$C_{12}$ alkyl indicates that the alkyl group may have from 1 to 12 (inclusive) carbon atoms, and $C_1$-$C_4$ alkyl indicates that the alkyl group may have from 1 to 4 (inclusive) carbon atoms. An alkyl group may be optionally substituted. Examples of $C_1$-$C_4$ alkyl groups include methyl, ethyl, n-propyl, isopropyl, n-butyl, sec-butyl and tert-butyl.

The terms "effective amount" or "therapeutically effective amount," as used herein, refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. The dose could be administered in one or more administrations. However, the precise determination of what would be considered an effective dose may be based on factors individual to each patient, including, but not limited to, the patient's age, size, type or extent of disease, stage of the disease, route of administration of the regenerative cells, the type or extent of supplemental therapy used, ongoing disease process and type of treatment desired (e.g., aggressive vs. conventional treatment).

As used herein, "exendin," "EX," and "Ex" are used interchangeably to mean the 39 amino acid polypeptide that acts as a glucagon-like peptide-1 receptor agonist. The polypeptide can be natural or synthetic. For example, exendin may be isolated or purified from recombinant or natural sources, such as bacteria or Gila monster lizard venom, Exendin may also be synthetic, such as the commercial form exenatide.

The term "hydroxyl" or "hydroxy," as used herein, means an —OH group.

A "peptide" or "polypeptide" is a linked sequence of two or more amino acids linked by peptide bonds. The polypeptide can be natural, synthetic, or a modification or combination of natural and synthetic.

"Small molecule," as used herein, refers to any small compound, generally less than 1 kDa, which may regulate or control a biological process. In some embodiments, small molecules bind specific biological macromolecules and act as an effector, altering the activity or function of the target. These compounds can be natural, such as secondary metabolites, or synthetic, such as antiviral drugs. They may have a beneficial effect against a disease, such as drugs or therapeutics.

"Stealth" or "stealth polymer," as used herein, refer to a molecule-polymer conjugate, or to the polymer thereof, that can remain undetected by immune cells in the bloodstream for a prolonged period of time. Stealth molecule-polymer conjugates are at least partially resistant to enzymatic degradation of the conjugate, or to the polypeptide thereof, such as by proteases, and opsonization, which is a common method used by immune system to recognize foreign particles. Accordingly, stealth molecule-polymer conjugates may have one or more of reduced antigenicity, reduced immunogenicity, increased stability, increased half-life, and increased bioavailability relative to other polymers, conjugates, non-stealth polymers, and/or non-stealth conjugates. The ability to delay, reduce, or prevent opsonization, recognition by the immune system, or clearance of a conjugate (or the polypeptide or molecules thereof) from the body may be referred to herein as a stealth property.

A "subject" or "patient" may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

As used herein, the term "transition temperature" or "$T_t$" refers to the temperature at which the material changes from one state to another, for example, soluble to insoluble. For example, below the $T_t$ the conjugate may be highly soluble. Upon heating above the transition temperature, for example, the conjugate may aggregate, forming a separate phase.

As used herein, "treat," "treating," and the like mean a slowing, stopping or reversing of progression of a disease or disorder when provided a composition described herein to an appropriate control subject. The terms also mean a reversing of the progression of such a disease or disorder to a point of eliminating or greatly reducing the cell proliferation. As such, "treating" means an application or administration of the compositions described herein to a subject, where the subject has a disease or a symptom of a disease, where the purpose is to cure, heal, alleviate, relieve, alter, remedy, ameliorate, improve or affect the disease or symptoms of the disease.

2. Thermally Responsive Polymer-Therapeutic Molecule Conjugate

Provided herein are thermally responsive polymer-therapeutic molecule conjugates comprising: a backbone comprising repeating monomer units; a plurality of oligoethylene glycol side chains; and a therapeutic molecule conjugated to the backbone, wherein the conjugate has a transition temperature between 23° C. and 40° C. Each oligoethylene glycol side chain is covalently attached at a first end to the backbone and may comprise two or three monomers of ethylene glycol repeated in tandem.

a) Backbone of Repeating Monomer Units

The thermally responsive polymer-therapeutic molecule conjugates comprise a backbone comprising repeating monomer units. The repeating monomer units may be selected from the group consisting of acrylate, methacrylate, acrylamide, methacrylamide, and combinations thereof. In some embodiments, the monomer unit is acrylate. In some embodiments, the monomer unit is methacrylate.

The backbone may comprise any number of repeating monomer units necessary for a transition temperature between 23° C. and 40° C. The backbone may comprise 100 to 1000 monomer units. The backbone may comprise at least 100, at least 200, at least 300, at least 400, at least 500, at least 600, at least 700, at least 800, or at least 900 monomer units. The backbone may comprise less than 1000, less than 900, less than 800, less than 700, less than 600, less than 500, less than 400, less than 300, or less than 200 monomer units. In some embodiments, the backbone comprises 100 to 600 repeating monomer units. In some embodiments, the backbone comprises 100 to 400 repeating monomer units. In some embodiments, the backbone comprises 200 to 300 repeating monomer units.

The repeating monomer unit may be substituted with at least one functional group. The functional group may be hydroxyl, $C_1$-$C_4$ alkoxy, or $C_1$-$C_4$ alkyl.

Each oligoethylene glycol side chain may comprise two or three monomers of ethylene glycol repeated in tandem. In some embodiments, 100% of the plurality of oligoethylene glycol side chains comprise three monomers of ethylene glycol repeated in tandem. In some embodiments, 100% of the plurality of oligoethylene glycol side chains comprise two monomers of ethylene glycol repeated in tandem.

In some embodiments, between 45% and 100% of the plurality of oligoethylene glycol side chains comprise two monomers of ethylene glycol repeated in tandem. At least 45%, at least 50%, at least 55%, at least 60%, at least 65%, at least 70%, at least 75%, at least 80%, at least 85%, at least 90%, or at least 95% of the plurality of oligoethylene glycol side chain may comprise two monomers of ethylene glycol repeated in tandem. Less than 100%, less than 95%, less than 90%, less than 85%, less than 80%, less than 75%, less than 70%, less than 65%, less than 60%, less than 55%, or less than 50% of the plurality of oligoethylene glycol side chain may comprise two monomers of ethylene glycol repeated in tandem. In some embodiments, between 45% and 80% of the plurality of oligoethylene glycol side chains comprise two monomers of ethylene glycol repeated in tandem.

Each oligoethylene glycol side chain may comprise a capping moiety on a second end. The capping moiety may be hydroxyl or $C_1$-$C_4$ alkyl. In some embodiments, the capping moiety is a $C_1$-$C_4$ alkyl.

b) Therapeutic Molecule

The therapeutic molecule may be selected from a polynucleotide, a peptide, a polypeptide, a carbohydrate, a small molecule, and a combination thereof.

The therapeutic molecule may be a peptide or polypeptide. The polypeptide may be a protein, protein domain, or a segment of a protein. The peptide and/or polypeptide may include, but is not limited to, therapeutic polypeptides such as interferons, insulin, exendin, blood factors, colony stimulating factors, growth hormones, interleukins, growth factors, therapeutic vaccines, calcitonins, tumor necrosis factors (TNF), and enzymes. Specific types of therapeutic proteins include, without limitation, enzymes utilized in enzyme replacement therapy; hormones for promoting growth in animals, or cell growth in cell culture; anticoagulants and active proteinaceous substances used in various applications, for example, in biotechnology or in medical diagnostics.

Specific examples or the peptide and/or polypeptide include, but are not limited to: asparaginase; glutamase; arginase; arginine deaminase; adenosine deaminase; ribonuclease; cytosine deaminase, trypsin; chymotrypsin, papin, betatrophin; epidermal growth factor (EGF), insulin; exendin; insulin-like growth factor (IGF), transforming growth factor (TGF), nerve growth factor (NGF), platelet-derived growth factor (PDGF), bone morphogenic protein (BMP), fibroblast growth factor (FGF) and the like; somatostatin; somatotropin; somatropin; somatrem; calcitonin; parathyroid hormone; colony stimulating factors (CSF); clotting factors; gastrointestinal peptides, such as vasoactive intestinal peptide (VIP), cholecytokinin (CCK), gastrin, secretin, and the like; erythropoietins; vasopressins; octreotide; pancreatic enzymes; dismutases such as superoxide dismutase; thyrotropin releasing hormone (TRH); thyroid stimulating hormone; luteinizing hormone; luteinizing hormone-releasing hormone (LHRH); growth hormone-releasing hormone (GHRH); tissue plasminogen activators; interleukin-1; interleukin-2; interleukin-10-(IL-10); interleukin-15; interleukin-17 (IL-17); interleukin-1 receptor antagonist (IL-1RA); glucagon-like peptide-1 (GLP-1); gastric inhibitor polypeptide (GIP), leptin, ghrelin; granulocyte monocyte colony stimulating factor (GM-CSF); interferon-α; adenosine deaminase; uricase; macrophage activator; chorionic gonadotropin; heparin; atrial natriuretic peptide; hemoglobin; retroviral vectors; relaxin; cyclosporin; oxytocin; and vaccines. In some embodiments, the therapeutic molecule is exendin.

The therapeutic molecule may be a polynucleotide. Examples of polynucleotides include, but are not limited to, polynucleotides and oligonucleotide sequences, including DNA and RNA, which may be double-stranded or single-stranded. Examples of polynucleotides include any natural or synthetic polynucleotides. Examples of polynucleotides include, but are not limited to, antisense oligonucleotides, silencing RNA (siRNAs), and anti-microRNA (anti-miR), long non-coding RNA, ribozymes, and analogs, derivatives or combinations thereof.

The therapeutic molecule may be a carbohydrate. Carbohydrates and their derivatives are clinically used for treatment of various diseases. The carbohydrate may be a polysaccharide or a monosaccharide or derivatives thereof, such as sulfonated compounds. The carbohydrates may be purified from natural sources, or be synthetically produced and include natural or modified synthetic monosaccharides.

The backbone of the thermally responsive polymer may be conjugated to any site anywhere on the molecule. For example, when the molecule comprises a polypeptide, the backbone may be conjugated to the polypeptide at the C-terminus, the N-terminus, or an internal amino acid, or a combination thereof. In some embodiments, the molecule comprises a polypeptide with the backbone conjugated to the C-terminus of the polypeptide.

At least one thermally responsive polymer may be conjugated to the molecule. In some embodiments, the molecule comprises a polypeptide conjugated to at least one thermally responsive polymer.

c) Conjugate Properties

The conjugate may have a transition temperature ($T_t$) between 23° C. and 40° C. In some embodiments, the conjugate has a transition temperature between 23° C. and 37° C. The transition temperature may be about 23° C., about 24° C., about 25° C., about 26° C., about 27° C. about 28° C., about 29° C., about 30° C., about 31° C., about 32° C., about 33° C., about 34° C. about 35° C., about 36° C., or about 37° C.

This phase transition behavior may allow the conjugate to form a gel-like depot upon administration to a subject. The depot will have the highest concentration of drug in the center, at the site of injection, and a decreasing concentration gradient towards the perimeter. Since the transition temperature is concentration dependent, the thermally responsive polypeptide may allow the gel-like depot to gradually resolubilize at the low concentration perimeter of the depot and slowly release the conjugate into the surrounding tissue.

The phase transition behavior may be used to localize the conjugate within a subject thereby improving the biodistribution or bioaccumulation at the cell, tissue, disease site, or organ level in need of the therapeutic molecule. When used therapeutically, this improved targeted delivery of biomolecules to disease sites and may thus provide enhanced diagnostic and therapeutic efficacy of these compounds.

Phase transition behavior may also enable purification of the conjugate using inverse transition cycling. "Inverse transition cycling" refers to a protein purification method for polypeptides having phase transition behavior, and the method may involve the use of the conjugate's reversible phase transition behavior to cycle the solution through soluble and insoluble phases, thereby removing contaminants and eliminating the need for chromatography.

The conjugates may also exhibit desirable properties over non-conjugated therapeutic molecules, or over polymer conjugates formed using methods other than those described herein. For example, conjugates produced as described herein may show improvement in one or more of solubility, stability, pharmacokinetics, or immunogenicity. The conjugates may have one or more of reduced antigenicity, reduced immunogenicity, increased stability, increased half-life, and increased bioavailability relative to non-conjugated therapeutic molecules or conjugates differing from those described herein, such as other forms of PEGylation.

The conjugates may be at least partially resistant to enzymatic degradation of the conjugate, or to the therapeutic molecule thereof, such as by proteases, nucleases, and opsonization, which is a common method used by immune system to recognize foreign particles. The improved stability and pharmacokinetics of the conjugates may manifest as an improvement in the half-life compared with a comparable biomolecule that is not conjugated to a polymer.

d) Method of Making the Conjugate

The thermally responsive polymer may be synthesized and subsequently grafted to the therapeutic molecule to form the conjugate, or alternatively, the thermally responsive polymer may be synthesized on the therapeutic molecule in situ. Methods of making the conjugate may include any of those methods known in the art. For example, the methods may include those detailed in International Patent Application No. PCT/US2010/024385, filed Feb. 17, 2010, published as WO 2010096422, which is incorporated herein by reference.

The thermally responsive polymer and conjugate may be synthesized using free-radical polymerization. In some embodiments, the free-radical polymerization comprises at least one of atom transfer radical polymerization (ATRP), reversible addition-fragmentation chain transfer (RAFT) polymerization, single-electron transfer free radical polymerization (SET-LRP), radical ring-opening polymerization (radical ROP), nitroxide-mediated radical polymerization (NMP), cobalt-mediated radical polymerization, telluride-mediated polymerization, and stibine-mediated polymerization. In some embodiments, the free-radical polymerization comprises Activator-Regenerated Electron Transfer-Atom Transfer Radical Polymerization (ARGET-ATRP).

The thermally responsive polymer and conjugate may be synthesized using at least one method selected from ionic ring-opening polymerization (ionic ROP), ring opening metathesis polymerization, ionic polymerization, condensation polymerization, and coordination polymerization.

The thermally responsive polymer may include chemical moieties that are reactive to specific chemical moieties that may be present or introduced into a therapeutic molecule, thereby allowing site-specific conjugation. The thermally responsive polymer may include nitrophenyl carbonate, succinimidyl carbonate, carboxyl, hydroxyl, azide, maleimide, linear alkyne, and strained alkynes, aldehyde and acetal end groups. The site specific conjugation may include, but is not limited to, specific and controllable biorthogonal reactions including: 1,3-dipolar cycloadditions between azides and cyclooctynes or between nitrones and cyclooctynes, oxime/hydrazone formation from aldehydes and ketones, tetrazine ligations, isocyanide-based click reactions, and quadricyclane ligations. Alternatively, the thermally responsive polymer may include a chemical moiety that can react with a portion of the therapeutic molecule, such as an amino acid side chain in a peptide or polypeptide, or a phosphate group in a polynucleotide.

The thermally responsive polymer may be synthesized in situ. The therapeutic molecule may be contacted with an initiator agent for free-radical polymerization under conditions that permit attachment of the initiator agent to the therapeutic molecule, for example at one or more of the N-terminus or C-terminus of a polypeptide, protein or combination thereof, or at one or more of the 5' or 3' end of a polynucleotide. The initiator agent assists in beginning the polymerization by interacting with the the rapeutic molecule and the monomer unit.

The therapeutic molecule with the attached initiator may be contacted with the monomer units under conditions suitable for polymerization to occur. Initiation sites on the therapeutic molecule can be generated prior to polymerization, or concurrently as polymerization occurs. Successive monomer units may be incorporated in the growing polymer chain by participating in the same type of chemical reactions used to initiate the polymer chain. Alternatively, the monomer units may include a leaving group that can be displaced with a nucleophilic group.

3. Drug Depot

Also provided is a drug depot comprising the thermally responsive polymer-therapeutic molecule conjugate as described herein. Upon injection into a patient, the conjugate may undergo a phase transition to form a drug depot. The depot restricts the release of drug and thus sustains its release over a longer period of time. As the gel-like depot to gradually resolubilizes at the low concentration perimeter of the depot and the conjugate and thus the therapeutic molecule will be released into the surrounding tissue.

4. Methods of Use a) Method of Treating a Disease or Disorder

The present disclosure also provides methods of treating a disease or disorder in a subject. The methods comprise administering an effective amount of the thermally responsive polymer-therapeutic molecule conjugate as detailed herein to the subject. The disease may include, but is not limited to, cancers, metabolic diseases, autoimmune diseases, cardiovascular diseases, respiratory diseases, allergies, and orthopedic disorders.

In some embodiments, the disease may be a disease associated with aberrant biological activity that a therapeutic molecule as described above may ameliorate. For example, in the case of the therapeutic molecule comprising a GLP-1 receptor agonist, exendin, or insulin, the invention provides a method for treating one or more metabolic disorders including type 1 or type 2 diabetes, hyperglycemia, and impaired glucose tolerance. In the case of the therapeutic molecule comprising a blood clotting factor, the inventors provides a method for treating one or more disorders including hemophilia, post-surgical bleeding, anticoagulation-induced bleeding, thrombocytopenia, factor VII deficiency, factor XI deficiency, and intracranial hemorrhage. In some embodiments, the disease or disorder is diabetes.

5. Administration and Dosing

The disclosed conjugates may be incorporated into pharmaceutical compositions suitable for administration to a subject (such as a patient, which may be a human or non-human) well known to those skilled in the pharmaceutical art. The pharmaceutical composition may be prepared for administration to a subject. Such pharmaceutical compositions may be administered in dosages and by techniques well known to those skilled in the medical arts taking into consideration such factors as the age, sex, weight, and condition of the particular subject, and the route of administration.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants may also be present in the composition, according to the judgment of the formulator. The route by which the composition is administered and the form of the composition will dictate the type of carrier to be used.

The conjugates and compositions disclosed herein may be administered prophylactically or therapeutically. In prophylactic administration, the conjugate or composition may be administered in an amount sufficient to induce a response. In therapeutic applications, the conjugate or composition is administered to a subject in need thereof in an amount sufficient to elicit a therapeutic effect. An amount adequate to accomplish this is defined as "therapeutically effective dose." Amounts effective for this use will depend on, e.g., the particular composition of the conjugate regimen administered, the manner of administration, the stage and severity of the disease, the general state of health of the patient, and the judgment of the prescribing physician.

The conjugates or compositions disclosed herein may be administered by methods well known in the art as described in Donnelly et al. (*Ann. Rev. Immunol.* 1997, 15, 617-648); Feigner et al. (U.S. Pat. No. 5,580,859, issued Dec. 3, 1996); Feigner (U.S. Pat. No. 5,703,055, issued Dec. 30, 1.997) and Carson et al. (U.S. Pat. No. 5,679,647, issued Oct. 21, 1997). One skilled in the art would know that the choice of a pharmaceutically acceptable carrier, including a physiologically acceptable compound, depends, for example, on the route of administration.

The conjugates or compositions disclosed herein may conveniently be presented in a single dose or as divided doses administered at appropriate intervals, for example, as two, three, four or more sub-doses per day. The sub-dose itself may be further divided, e.g., into a number of discrete loosely spaced administrations.

As will be readily apparent to one skilled in the art, the useful in vivo dosage to be administered and the particular mode of administration will vary depending upon the age, weight, the severity of the affliction, and mammalian species treated, the particular conjugates employed, and the specific use for which these conjugates are employed. The determination of effective dosage levels, that is the dosage levels necessary to achieve the desired result, can be accomplished by one skilled in the art using routine methods, for example, human clinical trials, in vivo studies and in vitro studies.

Dosage amount(s) and interval(s) may be adjusted individually to provide plasma levels of the therapeutic molecule which are sufficient to maintain the modulating effects, or minimal effective concentration (MEC). The MEC will vary for each therapeutic molecule but can be estimated from in vivo and/or in vitro data. Dosages necessary to achieve the MEC will depend on individual characteristics and route of administration. However, assays well known to those in the art may be used to determine plasma concentrations. Dosage intervals can also be determined using MEC value. Conjugates or compositions should be administered using a regimen which maintains plasma levels above the MEC for 10-90% of the time, preferably between 30-90% and most preferably between 50-90%. In cases of local administration or selective uptake, the effective local concentration of the therapeutic molecule may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the symptoms to be treated and the route of administration. Further, the dose, and perhaps dose frequency, will also vary according to the age, body weight, and response of the individual patient. A program comparable to that discussed above may be used in veterinary medicine.

A therapeutically effective amount of the conjugates or compositions may be administered alone or in combination with a therapeutically effective amount of at least one additional therapeutic agents. In some embodiments, effective combination therapy is achieved with a single composition or pharmacological formulation that includes both agents, or with two distinct compositions or formulations, administered at the same time, wherein one composition includes a compound of this invention, and the other includes the second agent(s). Alternatively, in other embodiments, the therapy precedes or follows the other agent treatment by intervals ranging from minutes to months.

A wide range of second therapies may be used in conjunction with the conjugates or compositions of the present disclosure. The second therapy may be a combination of a second therapeutic agent or may be a second therapy not connected to administration of another agent. Such second therapies include, but are not limited to, surgery, immunotherapy, radiotherapy, or administration of a chemotherapeutic agent.

6. Examples

It will be readily apparent to those skilled in the art that other suitable modifications and adaptations of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

EXAMPLE 1

Materials and Methods

Amide-based azide-jimetional initiator synthesis, purification and characterization. 2-Bromoisobutanoic acid N-hydroxysuccinimide ester (0.0041 mol; 1.09 g) was purged with argon for 30 minutes and dissolved in 8.1 ml anhydrous dichloromethane. In a second reaction flask, 3-azido-1-propanamine (0.0049 mol; 0.52 g) was purged with argon for 30 minutes and dissolved in 7.49 ml anhydrous dichloromethane followed by cooling to 0° C. in an ice bath. 2-Bromoisobutanoic acid N-hydroxysuccinimide ester solution was dropwise added to flask containing 3-azido-1-propanamine under inert atmosphere. The resulting solution was reacted on ice for 30 minutes and left stirring at room temperature for 12 hours. The reaction solution was diluted in dichloromethane and passed through PVDF membrane followed by evaporation under vacuum. The resulting reaction solution was washed with saturated sodium carbonate followed by incubation over magnesium sulfate. The solution was then filtered through a PVDF membrane followed by evaporation under vacuum. The final product was characterized via nuclear magnetic resonance (NMR) spectroscopy using deuterated chloroform as solvent and upstream reference and using trimethylsilyl (TMS) as downstream reference. The final product ($C_7H_{13}BrN_4O$) was also analyzed by reverse-phase high pressure liquid chromatography (RP-HPLC) equipped with a high-resolution mass spectrometer at positive ion mode using a C18 column. The mobile phase consisted of water/acetonitrile/0.3% formic acid with 0-95% acetonitrile gradient.

Characterization of OEGMA monomers. Triethylene glycol methyl ether methacrylate (EG3, Sigma Aldrich, #729841) and diethylene glycol methyl ether methacrylate (EG2, Sigma Aldrich, #447927) monomers were diluted in water/acetonitrile (1:20000) and analyzed by RP-HPLC equipped with a high-resolution mass spectrometer at positive ion mode using a C18 column. The mobile phase consisted of water/acetonitrile/0.3% formic acid. The gradient was 5-95% acetonitrile over 10 min. The monomers were also characterized via NMR spectroscopy using deuterated chloroform as solvent and upstream reference and using TMS as downstream reference.

Activator-Regenerated Electron Transfer-Atom Transkr Radical Polymerization (ARGET-ATRP). EG3 and EG2 monomers were passed through basic alumina column to remove inhibitors. All other materials (tris(2-pyridylmethyl) amine (TPMA), copper (II) bromide (CuBr2), ascorbic acid, methanol and sodium chloride NaCl)) were purchased from Sigma Aldrich and used as received.

In a typical ARGET-ATRP, a schlenk flask containing EG3 (0.94 mmol; 212.82 µl) and EG2 monomers (1.56 mmol; 287.68 µl), amide-based azide-functional initiator (0.2M; 31.25 µl), TPMA: CuBr2 complex (0.8M; 0.1M; 15.63 µl), methanol (1468.75 µl) and 100 mM NaCl solution (2983.87 µl) was sealed and cooled to 0° C. in an ice bath. A separate schlenk flask containing 16 mM ascorbic acid in deionized water was also prepared. Both flasks were purged with argon for 45 minutes on ice. After deoxygenation, ascorbic acid solution was continuously injected to polymerization flask at a rate of 1 µl min-1 using a syringe pump. The polymerization was allowed to proceed for a specified time under inert atmosphere and quenched by exposing to air followed by storing at −20° C. for 1 hour.

Absolute molar mass (Mn and Mw) and polydispersity (Đ) characterization of POEGMA. Absolute number-averaged molar mass (Mn), absolute weight-averaged molar mass (Mw) and polydispersity (Đ) of POEGIVIAs were measured via gel-permeation chromatography-multi-angle light scattering (GPC-MALS). To do so, 2 mg ml$^{-1}$ POEGMA solution in tetrahydrofuran (THF) was prepared followed by filtration through a 0.2.2 µm filter. The sample (50 µl) was then separated on an Agilent 1100 analytical HPLC system equipped with a UV detector operating at 254 nm, DAWN TREOS (Wyatt Technology) light scattering detector and Wyatt Optilab T-rEX (Wyatt Technology) refractive index detectors. The mobile phase consisted of 0.1% LiBr in THF and flow rate was set to 1 ml/min. Absolute number-averaged molar mass (Mn), absolute weight-averaged molar mass (Mw) and polydispersity (Đ) of a particular POEGMA were calculated by ASTRA software (v. 6.0, Wyatt Technology) using refractive index increment (dn/dc) value of that particular POEGMA calculated by ASTRA software at 658 nm. DAWN TREOS light scattering detector was annually calibrated in toluene by Wyatt Technology and normalized with 30 kDa polystyrene (Wyatt Technology) prior to each analysis.

Structural characterization of POEGMA. Structure and monomer composition of POEGMAs were characterized via hydrogen NMR spectroscopy. Briefly, samples were weighed and dissolved in deuterated chloroform containing 0.05% (v/v) TMS at a final concentration of 10 mg ml$^{-1}$. Varian 400 MHz NMR instrument was used to collect at least 32 acquisitions for each sample. Data was analyzed by ACD/NMR software (ACD Labs).

Monomer composition of POEGMAs was defined as 2EG-long monomer content (%) and calculated from the integral value that corresponds to average number of hydrogens (H) present in the OEG side-chain (b; 03.4-4.4 ppm; 6 H for $EG2_{100\%}$ homopolymer; 10 H for $EG3_{100\%}$ homopolymer) except chain end-group (c; 3.5-3,3 ppm; 3 H) and methylene protons (a; 4.0-4.4 ppm; 2 H). To calculate 2EG-long monomer content (%) (y), the integral value of b region (b), was plugged in a linear equation, y=(−25*b)+250. This equation was formed based on the fact that $EG2_{100\%}$, which exclusively consists of EG2 monomers (100% EG2), and $EG3_{100\%}$ polymer, which does not contain any EG2 monomer (0% EG2), have integral values of 6 and 10 H in the b region described above, respectively (FIG. 5A).

Degrees of polymerization (DP) of POEGMA was calculated by subtracting mass of initiator from Mw calculated by GPC-MALS and then dividing the resulting mass to average mass of monomeric unit at the indicated monomer composition calculated by hydrogen NNW spectroscopy.

Hydrodynamic size characterization of POEGMA and Exendin-POEGMA conjugates. Hydrodynamic size of POEGMA. and exendin-POEGMA conjugates was characterized via Dynamic Light Scattering (DLS). Samples were prepared in PBS at a concentration of 25-50 µM and filtered through 100 nm filters (Whatman Anotop 10). The samples were then loaded on a black 384-well-plate and DLS was performed on a temperature controlled DynaPro Plate Reader (Wyatt Technology). 10 repeat measurements of 10 second acquisitions were made for each sample at 15° C. and data was analyzed by applying a regularization fit to the light scattering intensity autocorrelation function for Raleigh spheres using Dynamics 6.12.0.3 software (Wyatt Technology). The laser wavelength and scattering angle of the instrument was 831.95 nm and 90°, respectively.

Phase behavior characterization of POEGMA and Exendin-POEGMA conjugates. Phase behavior of POEGMA and exendin-POEGMA conjugates was characterized via UV-vis spectroscopy. Samples were prepared at indicated concentrations varying between 1-1000 µM in Dulbecco's phosphate buffered saline (DPBS) without calcium and magnesium (Hyclone) followed by filtration through a 1 µm filter. The filtered samples were then loaded on quartz cuvettes and optical density of samples at 600 nm ($OD_{600}$) was monitored as temperature increased and decreased at a rate of 1° C. min-1 using a temperature-controlled. UV-vis spectrophotometer (Cary 300 Bio, Varian Instruments). The phase transition of POEGMA was indicated by a sharp increase or decrease in $OD_{600}$ as temperature increased or decreased, respectively. Transition temperature ($T_t$) was defined as inflection point of $OD_{600}$ when it was plotted as a function of temperature and calculated as the maximum of first derivative using GraphPad Prism 7.0 software.

Protein expression and purification. E. coli cells transfected with plasmids encoding sortase A and exendin were available from a previous study. Both proteins were expressed and purified as previously described with minor changes.

Exendin was expressed as a fusion protein of elastin-like polypeptide (ELP) with a sortase A recognition sequence (LPETG amino acids; srt) and polyhistidine tag ($His_6$) inserted in between, exendin-srt-$His_6$-ELP (ESE). Cells harboring ESE gene inserted plasmid were cultured in 2XYT media (16 g L$^{-1}$ Tryptone, 10 g L$^{-1}$ yeast extract and 5.0 g L$^{-1}$ NaCl) supplemented with 45 µg ml$^{-1}$ kanamycin at 25° C. until $OD_{600}$ reaches to 0.6. When $OD_{600}$ is 0.6, temperature was set to 16° C. and isopropyl β-D-1-thiogalactopyranoside (IPTG, AMRESCO) was added to final concentration of 0.75 mM to induce expression of the fusion protein. Cells were harvested after overnight culture by centrifugation at 700 g for 15 minutes at 4° C. followed by resuspension in PBS. Resuspended cells were then lysed by sonication on a Misonex Ultrasonic Liquid Processor (Qsonica, LLC). The sonicator was set to 85 amplitude and was operated for 10 s after followed by a 40 s off-cycle for a total of 15 minutes. After cell lysis, nucleic acids were precipitated by adding polyethyleneimine (PEI) to 1% vol (Acros Chemicals) followed by centrifugation at 21000 g for 15 minutes at 4° C. In the purification of ESE, nonchromatographic inverse transition cycling (ITC) method was used as ELP imparts temperature- and salt-responsive phase transition behavior to the fusion protein. The supernatant was equilibrated with room temperature and phase transition of ELP tag was triggered by adding 0.1 M ammonium sulfate, and phase-transitioned fusion protein was recovered by centrifugation at 21000 g for 15 minutes at room temperature (hot spin). The supernatant was removed, and the fusion protein was dissolved in cold PBS followed by centrifugation at 21000 g for 15 minutes at 4° C. to remove any insoluble material (cold spin). The hot and cold spins were repeated two more times to obtain >99% purity, verified by sodium dodecyl sulfate-polyacrylamide gel electrophoresis (SDS-PAGE). In the final hot spin, the fusion was resolubilized in sortase buffer (50 mM Tris, 150 mM NaCl, 10 mM CaCl2, pH 7.5). ESE yield was determined to be 15 mg L$^{-1}$ using bicinchoninic acid (BCA) assay (Pierce, Thermo Scientific).

The cells harboring gene encoding sortase-A with an N terminal polyhistidine tag ($His_6$) were cultured in 2XYT media supplemented with 100 µg ml$^{-1}$ ampicillin at 37° C.

until OD$_{600}$ reaches to 0.6. When OD$_{600}$ is 0.6, IPTG was added to final concentration of 0.1 mM to induce protein expression. Cells were harvested after overnight culture by centrifugation at 700 g for 15 minutes at 4° C. followed by resuspension in PBS. Resuspended cells were then lysed by sonication on a Misonex Ultrasonic Liquid Processer (Qsonica, LLC). The sonicator was set to 85 amplitude and was operated for 10 s after followed by a 40 s off-cycle for a total of 15 minutes. After cell lysis, nucleic acids were precipitated by adding polyethyleneimine (PEI) to 1% vol (Acros Chemicals) followed by centrifugation at 21000 g for 15 minutes at 4° C. The resulting solution consisting of were then loaded on HisPur Cobalt Resin (Pierce, Thermo Scientific) and sortase-A was purified according to the manufacturer's protocols. Sortase-A purity and yield were determined to be >95% by SDS-PAGE and 186 mg L$^{-1}$ by absorbance measurement at 280 nm, respectively.

Site-specific and stoichiometric synthesis and purification of exendin-DBCO. A bio-orthogonal dibenzocyclooctyne (DBCO) group was installed on the C-terminus of exendin via sortase A-mediated native peptide ligation mechanism, yielding exendin-DBCO. Briefly, ESE (100 μM) and sortase A (50 μM) was reacted in the presence of DBCO-Gly$_3$ (5 mM; Click Chemistry Tools) in sortase buffer at room temperature for 16 hours. The resulting reaction solution was purified via reverse immobilized metal affinity chromatography (IMAC). Briefly, the solution was loaded to His-Trap HP (GE Healthcare) columns on an AKTA Purifier (GE Healthcare) equipped with a photodiode array operating at 220 and 280 nm. Exendin-DBCO was collected in flow through as it was the only species not bearing a His$_6$ moiety thus not interacting with the resin. Exendin-DBCO was concentrated using Centricon 70 (Milipore Sigma) concentrators with 3000 Da cut-off followed by dialysis into cold water overnight to remove unreacted DBCO-Gly$_3$ and lyophilization. Stoichiometric (1:1) and site-specific attachment of DBCO handle to the C-terminus of exendin was confirmed by Matrix-Assisted Laser Desorption/Ionization-Time-of-Flight mass spectroscopy (MALDI-TOF-MS) and tryptic digestion followed by MS, respectively.

Exendin-POEGMA conjugate synthesis and purification. Azide functional POEGMA and exendin-DBCO was dissolved in PBS at 1:1.05 ratio and reacted overnight at 4° C. Conjugation was confirmed via SDS-PAGE.

Purification of depot-forming exendin-POEGMA conjugates was simply achieved by triggering phase transition behavior imparted by POEGMA. Briefly, conjugation mixtures were equilibrated with room temperature and phase transition was triggered by adding 0.1 M ammonium sulfate. The phase-transitioned fusion conjugate was recovered by centrifugation at 21000 g for 15 minutes at room temperature. The supernatant containing small amount of free exendin-DBCO was removed, and the conjugate was dissolved in cold PBS. The last two steps were typically repeated two more times to obtain conjugates with purity >99%, verified by SDS-PAGE and HPLC. In the final step, the fusion was resolubilized in ultra-pure water and lyophilized.

Soluble exendin-POEGMA conjugates were purified via a single round of size exclusion chromatography. Conjugates were purified using an AKTA purifier equipped with a photodiode array detector operating at 220 and 280 nm and a HiLoad 16/600 Superdex 75 pg at 4oC using water as mobile phase. Purified conjugates were concentrated using amicon concentrators (Milipore Sigma) with 3000 Da cut-off and lyophilized.

Physical characterization of exendin-POEGMA conjugates. Exendin-POEGMA conjugates were characterized in terms of their Mn, Mw and Đ by SEC-MALS. To do so, conjugates at 0.5 mg ml$^{-1}$ were dissolved in 10 mM phosphate buffer at pH 7.4 followed by filtration through a 100 nm filter. Filtered conjugates were then separated on an Agilent 1260 analytical HPLC system equipped with a KW803 protein column (Shodex) and a DAWN HELEOS II (Wyatt Technology) light scattering detector in addition to a UV detector operating at 280 nm and an Optilab T-rEX (Wyatt Technology) refractive index detector serving as upstream and downstream concentration detectors, respectively. The mobile phase was 30 vol % methanol in 10 mM phosphate buffer at pH 7.4 and flow rate was 0.5 ml min$^{-1}$.

Mn, Mw and Đ of a particular exendin-POEGMA conjugate were calculated by ASTRA 7.00 software (Wyatt Technology) using build-in protein conjugate method. The method requires to enter dn/dc values and 280 nm UV-extinction coefficients of exendin-DBCO and that particular POEGMA used in the synthesis of the conjugate, dn/dc values were measured in the given mobile phase using build-in dn/dc calculation method of ASTRA and confirmed by injecting known concentrations of samples directly into Optilab T-rEX detector. 280 nm UV extinction coefficient of exendin-DBCO was calculated by ExPASY ProtPram tool upon entering its sequence, while that of POEGMAs was calculated by ASTRA software using its build-in methods.

DAWN HELEOS II light scattering detector was annually calibrated in toluene by Wyatt Technology and normalized with 2 mg ml$^{-1}$ bovine serum albumin (Pierce, Thermo Scientific) using the given mobile phase prior to each analysis.

In vitro activity of exenciin variants. In vitro activity of exendin-POEGMA conjugates was tested in terms of their ability to activate a G-protein-coupled receptor, namely glucagon-like peptide 1 receptor (GLP1R), whose intracellular signaling cascade is mediated by cyclic adenosine monophosphate (cAMP). Intracellular cAMP release upon GLP1R activation by exendin variants was quantified in Human Embryonic Kidney 293 (HEK293) cells, which were recombinantly engineered to express GLP1R as well as cAMP responsive element (CRE) fused to luciferase as reporter, abbreviated as HEK293/CRE-Luc/GLP1R.

HEK293/CRE-Luc/GLP1R cells were cultured in high glucose DMEM (Gibco) supplemented with 10% fetal bovine serum, 400 μg ml$^{-1}$ G418 (Thermo Fisher) and 200 μg ml$^{-1}$ G418 (Invitrogen). Cells were subcultured at least once prior to assay at approximately 80% confluency. One day prior to performing the assay, cells were seeded without antibiotics in phenol-free DMEM (Gibco) on 96-well plates at 25,000 cell per well in 90 μl media, and incubated at 37° C. under 5% CO2 atmosphere overnight. Exendin-POEGMA conjugates (20 μM in PBS) were incubated with dipeptidyl peptidase IV (DPP-IV, Prospec Bio) to expose active N-terminus for 16 h at room temperature. DPPIV amount was set to 2.5 mass % of exendin present in the conjugates. On the day of the assay, exendin stock (Santa Cruz Biotechnology) was dissolved to a final concentration of 20 μM in PBS, and logarithmic serial dilutions were made for each exendin variant in PBS in the range of 0-10-6 μM. 10 μl of each dilution were then separately transferred to at least 5 wells per dilution, yielding exendin variants in the concentration range of 0-1,000 nM. The plates were then incubated at 37° C. for 5 hours followed by equilibration with room temperature for 1 hour. Intracellular luciferase levels were measured upon treatment of cells with 100 μl Bright-Glo™ reagent (Promega) followed by incubation for 2 minutes and reading luciferase signal using Victor plate reader (Perkin Elmer). Data was analyzed by subtracting the mean signal derived from PBS-treated control wells from that from treated with exendin variants at various doses. The dose response and effective half-maximal dose (EC50) of each exendin variant were determined by fitting a four-parameter logistic nonlinear regression model using GraphPad Prism 7 software.

Animal studies and endotoxin purification. All in vivo studies were conducted under protocols approved by Duke Institutional Animal Care and Use Committee (IACUC) with six-week old male C57BL/6J mice (stock no. 000664) purchased from Jackson Laboratories. On the day of arrival, mice were placed on 60 kcal % fat diet (#D12492, Research Diets Inc.) and kept on the diet for at least 10 days to induce diabetic phenotype. Previous literature studies have established C57BL/6J mice kept on 60 kcal % fat diet for one week as an adequate diet-induced obesity (DIO) type-2 diabetes model as they exhibit elevated blood glucose, compromised insulin response and high insulin levels. Mice were group-housed (3 mice per cage) under controlled photoperiod with 12 h light and 12 h dark cycles and acclimated to the facility for at least 10 days prior to start of experiments. Mice had ad libitum access to water and food unless otherwise noted. Treatment groups were randomized.

All exendin-variants were endotoxin purified and sterilized prior to injection by using high capacity endotoxin removal spin columns (Pierce, Thermo Scientific) and sterile 0.22 μm Acrodisc filter with Mustang E membrane (Pall Corporation). Endotoxin amount was tested using Charles River Endosafe nexgen-PTS instrument and Endosafe cartridges and confirmed to be below 5 EU per kg mouse body weight as suggested by USP (United States Pharmacopeia).

Pharmacodynamics. Pharmacodynamics of exendin variants were determined by monitoring blood glucose and body weight of fed mice following a single subcutaneous (S.C.) injection. On day 0, initial body weight and blood glucose were measured. One day prior to injection, the tail was sterilized with alcohol absorbed pads and wiped dry. A tiny nick was made using a lancet, the first drop of blood (~1-2 μl) was wiped off and the second drop (~1-2 μl) was used to measure blood glucose using a glucometer (AlphaTrack, Abbott). On the day of injection, body weight and fed blood glucose levels were measured (t=0) and exendin variants kept on ice or equivalent volume of PBS were subcutaneously administered to mice. Immediately after injection, mice were placed in their cages to have ad libitum access to water and food and fed blood glucose levels were measured at 1-, 4-, and 8-h time points and every 24 h thereafter until no significant effect was observed. Body weight was also tracked daily as exendin provides weight-lowering benefits.

In the dose-response experiment, six-week old male C57BL/6J mice (n=6) maintained on 60 kcal % fat diet for 10 days were administered with PBS (−control) and an exendin-POEGMA conjugate at 500 μM with $T_t$ of 27.9° C. at 1000, 750, 500, 250, 100 and 25 nmol kg$^{-1}$ doses. Injection volume: body weight ratio was kept constant among doses by constituting lower doses with free POEGMA. $T_t$ difference among doses was confirmed to be less than 1° C.

In $T_t$ optimization experiments, six-week old male C57BL/6J mice (n=6) maintained on 60 kcal % fat diet for 5 weeks were administered with exendin-POEGMA conjugates, exendin (+control) and PBS (−control) at 1000 nmol kg$^{-1}$.

Blood glucose data was plotted as a function of time as raw values and/or normalized values. Normalization was achieved by dividing the raw values by average glucose level measured immediately before injection to correct transient variations in blood glucose and reflect per cent change in blood glucose as previously described in literature. Area under the curve (AUC) was quantified for each subject and plotted to compare glycemic regulation across groups as previously described in literature.

Statistical Analyses. Animals were randomized. All data was presented as mean ± standard error of the mean (SEM) unless otherwise noted. Blood glucose and body weight data were analyzed using two-way analysis of variance (ANOVA) and a test was considered significant if the P value is <0.05 (*P<0.05; P<0.01; *P<0.001; **** P<0.0001; ns: P>0.05). Comparisons between or among groups/time points were made by unpaired parametric two-tailed t-test or post-hoc Dunnett's multiple comparison test, respectively. Glucose exposure AUCs were computed using trapezoid rule and compared using Tukey's or Bonferroni's multiple comparison tests. All statistical analyses were performed using GraphPad Prism 7.0.

EXAMPLE 2

Synthesis and Characterization of POEGMA Library

Figure 1:
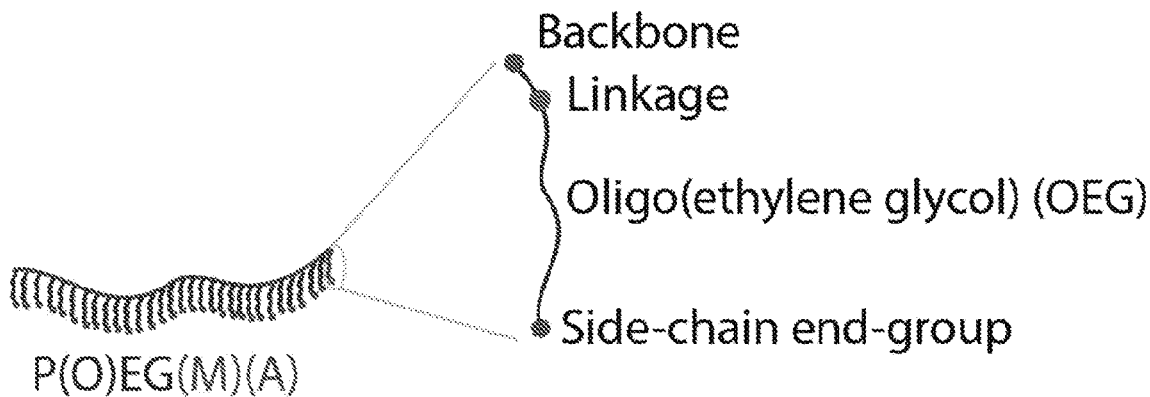
FIG. 1 is a schematic of the structure of POEGMA.

A next generation PEG-like amphiphilic stealth polymer, poly[oligo(ethylene glycol) methyl ether methacrylate] (POEGMA), conjugate technology was previously developed in which the immunogenic and hydrophilic long ethylene glycol sequences found in PEG are distributed along a hydrophobic poly(methacrylate) backbone as oligomeric ethylene glycol (EG) side-chains (FIG. 1). POEGMA with an average of nine EGs as side-Chains conferred the same pharmacokinetic (PK) advantages of traditional PEGylation technology and eliminated the reactivity towards patient-derived anti-PEGs upon further shortening the OEG side-chain length down to three without compromising in vivo efficacy and PK advantages. In addition, reactivity towards anti-PEGs was overcome by utilizing POEGMA in which epitope sites are sufficiently shortened by presenting only 3EG-long side-chains along a hydrophobic backbone.

Figure 2:
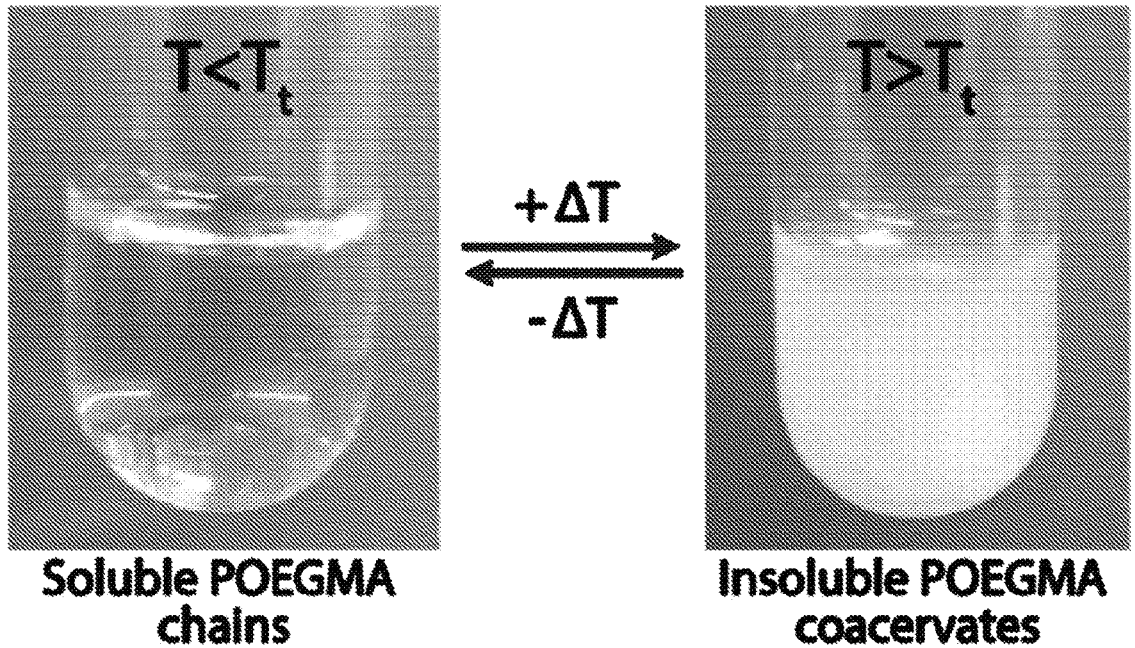
FIG. 2 are images of the reversible and thermo-responsive phase behavior of POEGMA.

As shown herein, further shortening OEG side-chain length down to two or combinations of two and three decreased overall hydrophilicity of POEGMA resulting in favored polymer-polymer interactions and phase transition from soluble chains to insoluble coacervates with increased temperatures. In addition to the eliminated anti-PEG reactivity further shortening of OEG side-chain also affected water interactions of POEGMA. as OEG moieties favor polymer-water interactions by making hydrogen bonds, while hydrophobic backbone and OEG chain end-groups favor polymer-polymer interactions. When polymer-water interactions dominate, POEGMA forms homogenous solutions. Therefore, as temperature increases, hydrogen bonding of OEG side chains become weaker and hydrophobic interactions among POEGMA chains dominate at a temperature defined as lower critical solution temperature (LCST). At its LCST, the POEGMA phase-separated and formed insoluble coacervates indicated by a sharp increase in optical density (FIG. 2). This phase transition can he reversed without significant hysteresis upon cooling or diluting the solution. As shown herein, this reversible temperature-responsive phase behavior of POEGMA can be tuned below or near body temperature to deliver therapeutics in depot formulation by engineering its hydrophobicity (EG side-chain length, backbone and/or chain end-group chemistry), architecture, sequence of side-chain segments, concentration, and molecular weight.

Characterization of triethylene glycol methyl ether methacrylate (EG3) and diethylene glycol methyl ether methacrylate (EG2) monomers: Polydisperse EG monomers typically provide limited control over the structure and properties of POEGMAs resulting in poly disperse polymers that exhibit non-uniform physical and in vivo profile. To achieve uniformity in polymer and bioconjugates, the structure of EG2 and EG3 monomers were analyzed via nuclear magnetic resonance (NMR) spectroscopy and high-resolution mass spectrophotometry (MS) and confirmed to consist of only 2 EG- and 3 EG-long chains, respectively.

Characterization of azide functional amide-based polymerization initiator: Commercially available ester-based polymerization initiators may be susceptible to hydrolytic cleavage and attacks by esterase enzymes upon in vivo administration, which may result in early cleavage of biomolecule from polymer moiety. To prevent this, an amide-based polymerization initiator bearing an azide moiety was synthesized, which was resistant to hydrolytic cleavage and esterase activity. Its structure was confirmed via NMR spectroscopy and high-resolution MS.

Synthesis and structural characterization of POEGMA library: Well-defined and azide functional POEGMAs were synthesized using activator-regenerated by electron transfer-atom transfer radical polymerization (ARGET-ATRP). The resulting POEGMAs with 3EG-long side chains, $EG3_{100\%}$, phase-transitioned above body temperature allowing only soluble state drug delivery, whereas more hydrophobic POEGMA with 2EG-long side-chains, $EG2_{100}\%$, phase-transitioned at room temperature preventing it from being injected. To tune transition temperature of POEGMA to near body temperature, average OEG side-chain length was varied by copolymerizing 2EG- and 3EG-long monomers at various ratios in monomer feed. POEGMAs at various molecular weight (Mw) and degrees of polymerization (DP) were synthesized, where 58, 66, 74, 82 and 90% of monomer chains were 2EG-long, yielding $EG2_{58\%}$, $EG2_{66\%}$, $EG2_{74\%}$, $EG2_{82\%}$ and $EG2_{90\%}$, respectively (FIGS. 3A-3C). The copolymers were monodisperse (polydispersity index (PDI) <1.2), at the expected Mw, structure and monomer composition, and azide end-functional. Summary of the characterization data is in FIG. 4.

Monomer composition of copolymers was defined as 2EG-long monomer content (%) and determined via Nuclear Magnetic Resonance (NMR) spectroscopy. 2EG-long monomer content (%) was calculated from the integral value that corresponds to average number of hydrogens (H) present in the OEG side-chain (FIG. 5; b; 3.4-4.4 ppm; 6 H $EG2_{100\%}$; 10 H $EG3_{100\%}$) except chain end-group (FIG. 5; c; 3.5-3.3 ppm; 3 H) and methylene protons (FIG. 5; a; 4.0-4.4 ppm; 2 H) in NMR spectrum. No significant monomer composition drift was observed under the applied conditions.

Rh of copolymers was determined via Dynamic Light Scattering at 15° C., where all copolymers were soluble. Even though, no statistically significant monomer composition-dependence was observed (P>0.05), we have found that DP and Mw had a significant effect on Rh of POEGMA copolymers. Rh increased with increasing DP and Mw as expected (FIG. 4).

EXAMPLE 3

Synthesis and Characterization of Exendin-POEGMA Conjugates

The first aim was to utilize POEGMA as an injectable depot-based drug delivery platform to improve in vivo efficacy of therapeutics upon their sustained release from subcutaneous depots into bloodstream. Depot-forming POEGMAs were conjugated to exendin, a potent peptide with a short plasma half-life (~2.4 h) used in the treatment of type 2 diabetes (T2D). Most peptide and protein biomolecule therapeutics, similar to exendin, are potent, selective, well-tolerated and have therefore become an important class of drugs despite their significant limitations in clinical use such as sub-optimal pharmacokinetics, poor stability, low solubility and immunogenicity. Exendin was used to exemplify the benefits of the POEGMA conjugates described herein.

Conventional conjugation methods typically provide limited control over the conjugation site and stoichiometry resulting in a heterogeneous mixture of conjugates that exhibit non-uniform physical and in vivo profile. To achieve uniformity in bioconjugate synthesis, bio-orthogonal click chemistry was utilized, which exploited the fast and side reaction-free nature of reactions involving functional groups that are orthogonal to those that exist in nature. First, a bio-orthogonal dibenzocylooctyne (DBCO) group was attached on the C-terminus of exendin via sortase A-mediated native peptide ligation mechanism (FIG. 6 and FIG. 7), yielding exendin-DBCO. The C-terminus of exendin was chosen because it could tolerate being modified without complete loss of activity. DBCO was utilized because it could readily react with azide groups present on POEGMAs via strain-promoted azide-alkyne cycloaddition (SPAAC). Site-specificity and stoichiometry (1:1) of exendin-DBCO were confirmed by Matrix-Assisted Laser Desorption/Ionization-Time-of-Flight mass spectroscopy (MALDI-TOF-MS) and tryptic digestion followed by MS, respectively (data not shown).

Exendin-DBCO was next conjugated to azide-functional POEGMAs with an EG2% of 76.5, 69.5, 60.5 and 48.6, yielding depot-forming exendin-POEGMA conjugates with $T_t$ of 27.9° C., 28.4° C., 29.9° C. and 31.9° C., Ex-$POEGMA_{27.9}$, Ex-$POEGMA_{28.4}$, Ex-$POEGMA_{29.9}$ and Ex-$POEGMA_{31.9}$, respectively. $T_t$ of depot-forming POEGMAs used in conjugate synthesis was engineered such that the conjugates remain soluble in a syringe at room temperature, but transitioned to an insoluble coacervates when injected, triggered by the increase from ambient to body temperature, at the injection concentration of 500 µM. A non-depot-forming control phase-transitioning well above body temperature, Ex-$POEGMA_{40}$ ($T_t$: 40° C.), was synthesized using POEGMA consisting of only 3EG-long monomers.

Exendin-POEGMA conjugates were well defined, monodisperse, and at the expected $M_w$ (FIG. 8A, FIG. 9). They had a slightly larger Rh and higher $T_t$ than their parent molecules (FIG. 8A, FIG. 9). Their phase behavior was monomer composition-dependent and reversible with no significant hysteresis (FIG. 8Band FIG. 10A). The conjugates also showed concentration-dependence (FIG. 8C and FIG. 10B) indicating that they could be released from depot into bloodstream in response to the concentration gradient at the boundary layer of depot. Finally, soluble and depot-forming exendin-POEGMA conjugates were tested in terms of their ability to activate GLP1R in an in vitro cell-based assay using exendin and PBS as positive and negative controls, respectively (FIG. 8D and FIG. 10C). Both soluble and depot-forming conjugates had significantly lower half-maximal effective concentration ($EC_{50}$) than exendin (0.04±0.01 nM) due to steric hindrance imparted by POEGMA. Exendin-DBCO also had lower $EC_{50}$(0.56±0.09 nM) than exendin due to C-terminus modification with DBCO (data not shown).

EXAMPLE 4

Dose-Response of Exendin-POEGMA Conjugates

A dose-response experiment was performed to determine optimal dose of exendin-POEGMA conjugates. 7-week old male diet induced obese (DIO) C57BL/6J mice, which were kept on 60 kcal% fat diet to induce diabetic phenotype, were used. Mice treated with an exendin-POEGMA conjugate with $T_t$ of 27.9° C. (Ex-POEGMA$_{27.9}$) at 1000, 750, 500, 250, 100 and 25 nmol kg body weight$^{-1}$ doses and PBS (−control) (n=6). Blood glucose was tracked throughout the injection day and every 24 h thereafter until no significant effect was observed. Body weight was tracked daily. Glucose exposure was calculated by integrating blood glucose over time (120 h), yielding area under the curve (AUC). Ex-POEGMA$_{27.9}$ lowered blood glucose in a dose-dependent manner (FIGS. 11A-11B) for up to 3 days and provided body weight lowering benefits (FIG. 11C) for 4 days (P<0.05). The optimal dose was verified to be 1000 nmol kg$^{-1}$ as it provided lowest glucose exposure (FIG. 11D), which accounted for both magnitude and duration of blood glucose control.

EXAMPLE 5

Dose-Response of Exendin-POEGMA Conjugates

It was hypothesized that exendin-POEGMA conjugates with $T_t$ below SC temperature of mice (~32° C.) would form stable depots allowing for sustained release of exendin upon concentration gradient at the boundary layer of depot. To test this hypothesis, exendin-POEGMA conjugates with variable $T_t$, 28.4° C., 29.9° C. and 31.9° C., but near-constant MW of ~55 kDa, were synthesized. This $M_w$ was chosen because it was reported to be the optimal POEGMA $M_w$ in literature. Mice were treated with the conjugates, equivalent dose of exendin (+control) and equivalent injection volume of PBS (−control) (n=6). Blood glucose was tracked throughout the injection day and every 24 h thereafter until no significant effect was observed (FIG. 12A). Body weight was tracked daily (FIG. 12B). Glucose exposure was calculated by integrating blood glucose over time (144 h), yielding area under the curve (AUC).

Mice treated with exendin and exendin-POEGMA conjugates had lower blood glucose levels compared to PBS-treated group. Exendin did not provide long-term blood glucose control due to its short half-life. The most hydrophobic conjugate (Ex-POEGMA$_{28.4}$) among those tested released only a small amount of drug resulting in only modest blood glucose control and change in body weight. The most hydrophilic conjugate among those tested, Ex-POEGMA$_{31.9}$, lowered blood glucose levels only for 5 days (FIGS. 12A-12B) possibly due to not being able to form a stable enough depot at SC temperature, which was equal to its transition temperature, and its faster absorption than Ex-POEGMA$_{29.9}$ owing to its more hydrophilic structure. Ex-POEGMA$_{30}$ conjugate outperformed others (FIG. 12C) by lowering blood glucose and providing body weight-lowering benefits for 6 days (FIGS. 12A-12B), possibly due to forming a stable enough depot at SC while releasing a desirable amount of drug to bloodstream.

POEGMA improved in vivo efficacy of exendin significantly by lowering blood glucose for 6 day as opposed to few hours with free peptide. As described herein, a stealth polymer conjugate technology superior to immunogenic PEGylation in which therapeutics can only be delivered in soluble-state, was identified. POEGMA allowed for sustained release or systemic delivery of therapeutics either in depot or soluble formulation, respectively, and eliminate reactivity towards anti-PEGs.

Phase behavior of POEGMA could be tuned to near body temperature upon engineering its hydrophobicity by varying its monomer content. Phase behavior of POEGMA was found to be a strong function of concentration indicating that drug release from the subcutaneous depot can be achieved in response to the concentration gradient at the boundary layer of the depot, which was crucial for the release of drug into bloodstream at constant body temperature. Second, non-trivial synthesis of site-specific, stoichiometric and depot-forming exendin-POEGMA conjugates was achieved, which lowered blood glucose for 6 days and provided body weight lowering benefits. POEGMA conjugates of exendin with a $T_t$ just below subcutaneous temperature optimized the magnitude and duration of exendin release from the depot into the bloodstream. The amount of therapeutic biomolecule in bloodstream could be tuned to desired level by tuning structure of POEGMA.

It is understood that the foregoing detailed description and accompanying examples are merely illustrative and are not to be taken as limitations upon the scope of the disclosure, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the disclosure, may be made without departing from the spirit and scope thereof.

For reasons of completeness, various aspects of the invention are set out in the following numbered clauses:

Clause 1. A thermally responsive polymer-therapeutic molecule conjugate comprising: a backbone comprising repeating monomer units selected from the group consisting of acrylate, methacrylate, acrylamide, methacrylamide, and combinations thereof; a plurality of oligoethylene glycol side chains; and a therapeutic molecule conjugated to the backbone; wherein a first end each oligoethylene glycol side chain is covalently attached to the backbone and each oligoethylene glycol side chain comprises two or three monomers of ethylene glycol repeated in tandem, and wherein the conjugate has a transition temperature between 23° C. and 40° C.

Clause 2. The conjugate of clause 1, wherein the backbone comprises 100 to 1000 repeating monomer units.

Clause 3. The conjugate of clause 1 or clause 2, wherein the backbone comprises 100 to 600 repeating monomer units.

Clause 4. The conjugate of any of clauses 1-3, wherein the backbone comprises 100 to 400 repeating monomer units.

Clause 5. The conjugate of any of clauses 1-4, wherein the backbone comprises 200 to 300 repeating monomer units.

Clause 6. The conjugate of clause 1, wherein the monomer unit is substituted with at least one functional group.

Clause 7. The conjugate of clause 6, wherein the nctional group is a hydroxyl, $C_1$-$C_4$ alkoxy, or $C_1$-$C_4$ alkyl Clause 8. The conjugate of any of clauses 1-7, wherein between 45% and 100% of the plurality of oligoethylene glycol side chains comprise two monomers of ethylene glycol repeated in tandem.

Clause 9. The conjugate of any of clauses 1-8, wherein between 45% and 80% of the plurality of oligoethylene glycol side chains comprise two monomers of ethylene glycol repeated in tandem.

Clause 10. The conjugate of any of clauses 1-9, wherein each oligoethylene glycol side chain comprises a capping moiety on a second end.

Clause 11. The conjugate of clause 10, wherein the capping moiety is hydroxyl or $C_1$-$C_4$ alkyl.

Clause 12. The conjugate of any of clauses 1-11, wherein the therapeutic molecule is selected from the group consisting of a polynucleotide, a peptide, a polypeptide, a carbohydrate, a small molecule, and a combination thereof.

Clause 13. The conjugate of any of clauses 1-12, wherein the therapeutic molecule is a polypeptide.

Clause 14. The conjugate of clause 13, wherein the backbone is conjugated to the polypeptide at a site selected from the C-terminus, the N-terminus, and an internal amino acid of the polypeptide.

Clause 15. The conjugate of any of clauses 1-14, wherein the therapeutic molecule is exendin.

Clause 16. The conjugate of any of clauses 1-15, wherein the conjugate has a transition temperature between 23° C. and 37° C.

Clause 17. A drug depot comprising the thermally responsive polymer-therapeutic molecule conjugate of any of clauses 1-16.

Clause 18. A method of treating a disease or disorder in a subject in need thereof comprising administering a therapeutically effective amount of the thermally responsive polymer-therapeutic molecule conjugate of any of clauses 1-16.

Clause 19. The method of clause 18, wherein the thermally responsive polymer-therapeutic molecule conjugate forms a drug depot when administered.

Clause 20. The method of clause 18 or clause 19, wherein the disease or disorder is diabetes.

What is claimed is:

1. A thermally responsive polymer-therapeutic molecule conjugate comprising:
   a backbone comprising 100 to 600 repeating monomer units selected from the group consisting of acrylate, methacrylate, acrylamide, methacrylamide, and combinations thereof;
   a plurality of oligoethylene glycol side chains; and
   a therapeutic molecule conjugated to the backbone;
   wherein each oligoethylene glycol side chain is covalently attached at a first end to the backbone and each oligoethylene glycol side chain comprises two or three monomers of ethylene glycol repeated in tandem,
   wherein between 45% and 85% of the plurality of oligoethylene glycol side chains comprise two monomers of ethylene glycol repeated in tandem, and
   wherein the conjugate has a transition temperature between 23° C. and 40° C.

2. The conjugate of claim 1, wherein the backbone comprises 100 to 400 repeating monomer units.

3. The conjugate of claim 1, wherein the backbone comprises 200 to 300 repeating monomer units.

4. The conjugate of claim 1, wherein the monomer unit is substituted with at least one functional group.

5. The conjugate of claim 4, wherein the functional group is a hydroxyl, $C_1$-$C_4$ alkoxy, or $C_1$-$C_4$ alkyl.

6. The conjugate of claim 1, wherein between 45% and 80% of the plurality of oligoethylene glycol side chains comprise two monomers of ethylene glycol repeated in tandem.

7. The conjugate of claim 1, wherein each oligoethylene glycol side chain comprises a capping moiety on a second end.

8. The conjugate of claim 7, wherein the capping moiety is hydroxyl or $C_1$-$C_4$ alkyl.

9. The conjugate of claim 1, wherein the therapeutic molecule is selected from the group consisting of a polynucleotide, a peptide, a polypeptide, a carbohydrate, a small molecule, and a combination thereof.

10. The conjugate of claim 1, wherein the therapeutic molecule is a polypeptide.

11. The conjugate of claim 10, wherein the backbone is conjugated to the polypeptide at a site selected from the C-terminus, the N-terminus, and an internal amino acid of the polypeptide.

12. The conjugate of claim 1, wherein the therapeutic molecule is exendin.

13. The conjugate of claim 1, wherein the conjugate has a transition temperature between 23° C. and 37° C.

14. A drug depot comprising the thermally responsive polymer-therapeutic molecule conjugate of claim 1.

15. A method of treating a disease or disorder in a subject in need thereof comprising administering a therapeutically effective amount of the thermally responsive polymer-therapeutic molecule conjugate of claim 1.

16. The method of claim 15, wherein the thermally responsive polymer-therapeutic molecule conjugate forms a drug depot when administered.

17. The method of claim 15, wherein the disease or disorder is diabetes.

18. The conjugate of claim 1, wherein the conjugate has a transition temperature between 26° C. and 37° C.

* * * * *